(12) United States Patent
DiPoto et al.

(10) Patent No.: US 7,655,012 B2
(45) Date of Patent: Feb. 2, 2010

(54) METHODS AND APPARATUSES FOR MINIMALLY INVASIVE REPLACEMENT OF INTERVERTEBRAL DISCS

(75) Inventors: Gene DiPoto, Upton, MA (US); Alan E. Shluzas, Millis, MA (US); Victor Rossin, Cambridge, MA (US); Stephen Anderson, Holliston, MA (US); Daniel Baker, Seattle, WA (US)

(73) Assignee: Zimmer Spine, Inc. MN (US)

( * ) Notice: Subject to any disclaimer, the term of this patent is extended or adjusted under 35 U.S.C. 154(b) by 627 days.

(21) Appl. No.: 10/842,651

(22) Filed: May 10, 2004

(65) Prior Publication Data

US 2005/0075644 A1    Apr. 7, 2005

Related U.S. Application Data

(60) Provisional application No. 60/508,784, filed on Oct. 2, 2003.

(51) Int. Cl.
*A61B 17/60* (2006.01)

(52) U.S. Cl. .................. 606/99; 606/279; 600/201; 623/17.11

(58) Field of Classification Search ................ 604/104, 604/106; 606/108, 99, 90, 198, 95, 79, 84–85, 606/279; 600/219, 220, 222, 201; 623/17.11–17.16
See application file for complete search history.

(56) References Cited

U.S. PATENT DOCUMENTS

| | | | |
|---|---|---|---|
| 2,876,777 A * | 3/1959 | Kees, Jr. ................. 606/84 |
| 3,044,461 A * | 7/1962 | Murdock ................ 600/208 |
| 3,486,505 A * | 12/1969 | Morrison ................ 606/90 |
| 3,789,852 A | 2/1974 | Kim et al. |
| 3,875,595 A | 4/1975 | Froning |
| 4,309,777 A | 1/1982 | Patil |
| 4,545,374 A | 10/1985 | Jacobson |
| 4,601,713 A | 7/1986 | Fuqua |
| 4,716,901 A | 1/1988 | Jackson et al. |
| 4,817,587 A * | 4/1989 | Janese ................ 600/210 |
| 4,819,620 A | 4/1989 | Okutsu |
| 4,827,928 A * | 5/1989 | Collis, Jr. ............... 606/79 |
| 4,863,133 A | 9/1989 | Bonnell |
| 4,911,718 A | 3/1990 | Lee et al. |
| 4,921,478 A | 5/1990 | Solano et al. |
| 4,932,969 A | 6/1990 | Frey et al. |
| 4,984,564 A | 1/1991 | Yuen |
| 5,020,519 A | 6/1991 | Hayes et al. |

(Continued)

FOREIGN PATENT DOCUMENTS

| | | |
|---|---|---|
| EP | 0 528 562 A2 | 2/1993 |
| EP | 0 807 415 A3 | 8/1998 |
| EP | 0 980 677 A1 | 2/2000 |
| EP | 1 251 767 A2 | 10/2002 |
| EP | 1 305 077 A1 | 5/2003 |

(Continued)

*Primary Examiner*—Thomas C Barrett
*Assistant Examiner*—James L. Swiger
(74) *Attorney, Agent, or Firm*—Crompton, Seager & Tufte, LLC.

(57) ABSTRACT

In one embodiment, an access device is inserted through an incision in skin of a patient. The access device is expanded from a first configuration to a second configuration, the second configuration having an enlarged cross-sectional area at a distal portion of said access device such that the distal portion extends across at least a portion of the interbody space. A prosthetic spinal disc implant is then delivered through the access device.

26 Claims, 52 Drawing Sheets

U.S. PATENT DOCUMENTS

| | | | |
|---|---|---|---|
| 5,025,778 | A | 6/1991 | Silverstein et al. |
| 5,131,382 | A | 7/1992 | Meyer |
| 5,139,499 | A | 8/1992 | Small et al. |
| 5,139,511 | A | 8/1992 | Gill et al. |
| 5,163,949 | A | 11/1992 | Bonutti |
| 5,171,279 | A | 12/1992 | Mathews |
| 5,190,561 | A * | 3/1993 | Graber .................. 606/127 |
| 5,195,541 | A | 3/1993 | Obenchain |
| 5,197,971 | A | 3/1993 | Bonutti |
| 5,224,680 | A | 7/1993 | Greenstein et al. |
| 5,287,845 | A | 2/1994 | Faul et al. |
| 5,295,994 | A | 3/1994 | Bonutti |
| 5,312,417 | A | 5/1994 | Wilk |
| 5,314,477 | A | 5/1994 | Marnay |
| 5,345,927 | A | 9/1994 | Bonutti |
| 5,354,302 | A | 10/1994 | Ko |
| 5,370,647 | A | 12/1994 | Graber et al. |
| 5,370,697 | A | 12/1994 | Baumgartner |
| 5,385,606 | A | 1/1995 | Kowanko |
| 5,395,317 | A | 3/1995 | Kambin |
| 5,401,269 | A | 3/1995 | Buttner-Janz et al. |
| 5,439,464 | A | 8/1995 | Shapiro |
| 5,454,365 | A | 10/1995 | Bonutti |
| 5,472,426 | A | 12/1995 | Bonati et al. |
| 5,484,437 | A | 1/1996 | Michelson |
| 5,489,307 | A | 2/1996 | Kuslich et al. |
| 5,520,607 | A | 5/1996 | Frassica et al. |
| 5,556,431 | A | 9/1996 | Büttner-Janz |
| 5,562,736 | A | 10/1996 | Ray et al. |
| 5,562,738 | A | 10/1996 | Boyd et al. |
| 5,571,072 | A | 11/1996 | Kronner |
| 5,575,754 | A | 11/1996 | Konomura |
| 5,601,690 | A | 2/1997 | Gauld et al. |
| 5,667,520 | A | 9/1997 | Bonutti |
| 5,674,295 | A | 10/1997 | Ray et al. |
| 5,676,701 | A | 10/1997 | Yuan et al. |
| 5,690,606 | A | 11/1997 | Slotman |
| 5,702,450 | A | 12/1997 | Bisserie |
| 5,702,454 | A | 12/1997 | Baumgartner |
| 5,707,359 | A | 1/1998 | Bufalini |
| 5,720,751 | A | 2/1998 | Jackson |
| 5,782,831 | A | 7/1998 | Sherman et al. |
| 5,782,832 | A | 7/1998 | Larsen et al. |
| 5,792,044 | A | 8/1998 | Foley et al. |
| 5,795,289 | A | 8/1998 | Wyttenbach |
| 5,800,549 | A | 9/1998 | Bao et al. |
| 5,824,093 | A | 10/1998 | Ray et al. |
| 5,827,319 | A | 10/1998 | Carlson et al. |
| 5,827,328 | A | 10/1998 | Buttermann |
| 5,902,231 | A | 5/1999 | Foley et al. |
| 5,910,141 | A | 6/1999 | Morrison et al. |
| 5,954,635 | A | 9/1999 | Foley et al. |
| 5,961,499 | A | 10/1999 | Bonutti et al. |
| 5,968,098 | A * | 10/1999 | Winslow ............... 623/17.11 |
| 5,997,508 | A | 12/1999 | Lunn et al. |
| 6,022,376 | A | 2/2000 | Assell et al. |
| 6,039,763 | A | 3/2000 | Shelokov |
| 6,053,907 | A | 4/2000 | Zirps |
| 6,063,121 | A | 5/2000 | Xavier et al. |
| 6,110,210 | A | 8/2000 | Norton et al. |
| 6,120,437 | A | 9/2000 | Yoon et al. |
| 6,132,465 | A | 10/2000 | Ray et al. |
| 6,146,422 | A | 11/2000 | Lawson et al. |
| 6,156,067 | A | 12/2000 | Bryan et al. |
| 6,162,236 | A | 12/2000 | Osada |
| 6,171,299 | B1 | 1/2001 | Bonutti |
| 6,187,000 | B1 * | 2/2001 | Davison et al. ............. 606/1 |
| 6,193,715 | B1 | 2/2001 | Wrublewski et al. |
| 6,206,826 | B1 * | 3/2001 | Mathews et al. ........... 600/210 |
| 6,240,926 | B1 | 6/2001 | Chin Gan et al. |
| 6,251,111 | B1 | 6/2001 | Barker et al. |
| 6,270,793 | B1 | 8/2001 | Van Dyke et al. |
| 6,274,155 | B1 | 8/2001 | Van Dyke et al. |
| 6,306,170 | B2 | 10/2001 | Ray |
| 6,312,443 | B1 | 11/2001 | Stone |
| 6,315,797 | B1 | 11/2001 | Middleton |
| 6,338,730 | B1 | 1/2002 | Bonutti et al. |
| 6,348,071 | B1 | 2/2002 | Steffee et al. |
| 6,358,226 | B1 | 3/2002 | Ryan |
| 6,358,266 | B1 | 3/2002 | Bonutti |
| 6,361,488 | B1 | 3/2002 | Davison et al. |
| 6,368,350 | B1 | 4/2002 | Erickson et al. |
| 6,371,968 | B1 | 4/2002 | Kogasaka et al. |
| 6,371,984 | B1 | 4/2002 | Van Dyke et al. |
| 6,375,862 | B1 | 4/2002 | Umeda et al. |
| 6,383,195 | B1 | 5/2002 | Richard |
| 6,419,706 | B1 | 7/2002 | Graf |
| 6,440,168 | B1 | 8/2002 | Cauthen |
| 6,478,800 | B1 * | 11/2002 | Fraser et al. ................ 606/99 |
| 6,494,893 | B2 | 12/2002 | Dubrul et al. |
| 6,497,654 | B1 | 12/2002 | Leonard et al. |
| 6,524,320 | B2 | 2/2003 | DiPoto |
| 6,530,880 | B2 | 3/2003 | Pagliuca |
| 6,530,926 | B1 | 3/2003 | Davison |
| 6,540,753 | B2 * | 4/2003 | Cohen ................... 606/99 |
| 6,540,785 | B1 * | 4/2003 | Gill et al. ............... 623/17.14 |
| 6,562,192 | B1 | 5/2003 | Hamilton et al. |
| 6,564,078 | B1 | 5/2003 | Marino et al. |
| 6,572,653 | B1 | 6/2003 | Simonson |
| 6,579,321 | B1 | 6/2003 | Gordon et al. |
| 6,582,466 | B1 | 6/2003 | Gauchet |
| 6,589,225 | B2 | 7/2003 | Orth et al. |
| 6,592,624 | B1 * | 7/2003 | Fraser et al. ............ 623/17.16 |
| 6,599,291 | B1 * | 7/2003 | Foley et al. ................. 606/79 |
| 6,610,094 | B2 | 8/2003 | Husson |
| 6,620,129 | B2 | 9/2003 | Stecker et al. |
| 6,645,127 | B1 | 11/2003 | Pestes |
| 6,648,888 | B1 | 11/2003 | Shluzas |
| 6,652,553 | B2 | 11/2003 | Davison et al. |
| 6,679,886 | B2 * | 1/2004 | Weikel et al. ................ 606/79 |
| 6,783,746 | B1 | 8/2004 | Zhang et al. |
| 6,811,558 | B2 | 11/2004 | Davison et al. |
| 6,837,889 | B2 | 1/2005 | Shluzas |
| 6,969,404 | B2 | 11/2005 | Ferree |
| 7,001,431 | B2 | 2/2006 | Bao et al. |
| 7,004,947 | B2 | 2/2006 | Shluzas et al. |
| 7,025,787 | B2 | 4/2006 | Bryan et al. |
| 7,066,937 | B2 | 6/2006 | Shluzas |
| 7,179,225 | B2 | 2/2007 | Shluzas et al. |
| 7,226,451 | B2 | 6/2007 | Shluzas et al. |
| 2001/0011170 | A1 | 8/2001 | Davison et al. |
| 2002/0025942 | A1 | 2/2002 | Ingram et al. |
| 2002/0049498 | A1 | 4/2002 | Yuksel et al. |
| 2002/0082701 | A1 | 6/2002 | Zdeblick et al. |
| 2002/0138078 | A1 * | 9/2002 | Chappuis .................. 606/85 |
| 2003/0014068 | A1 | 1/2003 | Bonutti et al. |
| 2003/0040656 | A1 | 2/2003 | Pagliuca et al. |
| 2003/0069643 | A1 | 4/2003 | Ralph et al. |
| 2003/0073998 | A1 | 4/2003 | Pagliuca et al. |
| 2003/0074076 | A1 | 4/2003 | Ferree et al. |
| 2003/0078667 | A1 | 4/2003 | Manasas et al. |
| 2003/0135217 | A1 * | 7/2003 | Buttermann et al. .......... 606/79 |
| 2003/0139648 | A1 | 7/2003 | Foley et al. |
| 2003/0153927 | A1 | 8/2003 | DiPoto et al. |
| 2003/0191371 | A1 | 10/2003 | Smith et al. |
| 2003/0195405 | A1 | 10/2003 | Marino et al. |
| 2003/0195493 | A1 | 10/2003 | Davison et al. |
| 2003/0195549 | A1 | 10/2003 | Davison et al. |
| 2003/0195550 | A1 | 10/2003 | Davison et al. |
| 2003/0195551 | A1 | 10/2003 | Davison et al. |
| 2003/0199871 | A1 | 10/2003 | Foley et al. |
| 2003/0199885 | A1 | 10/2003 | Davison et al. |
| 2003/0216748 | A1 * | 11/2003 | Gitis et al. ................. 606/108 |
| 2004/0059339 | A1 | 3/2004 | Roehm, III et al. |

| | | | |
|---|---|---|---|
| 2004/0078051 A1 | 4/2004 | Davison et al. | |
| 2004/0093002 A1 | 5/2004 | Davison et al. | |
| 2004/0098012 A1 | 5/2004 | Davison et al. | |
| 2004/0230100 A1 | 11/2004 | Shluzas | |
| 2005/0245942 A1 | 11/2005 | DiPoto | |
| 2005/0251192 A1 | 11/2005 | Shluzas et al. | |
| 2005/0273132 A1 | 12/2005 | Shluzas et al. | |
| 2006/0041313 A1 | 2/2006 | Allard et al. | |
| 2006/0069404 A1 | 3/2006 | Shluzas et al. | |
| 2006/0085011 A1 | 4/2006 | Filippi et al. | |
| 2006/0085077 A1 | 4/2006 | Cook et al. | |
| 2006/0106462 A1 * | 5/2006 | Tsou ....................... 623/17.16 | |

FOREIGN PATENT DOCUMENTS

| | | |
|---|---|---|
| FR | 2 701 379 | 6/1994 |
| JP | 2000-83960 A2 | 3/2000 |
| JP | 2001-149376 A2 | 6/2001 |
| WO | WO 92/21292 A2 | 2/1993 |
| WO | WO 93/14801 A1 | 8/1993 |
| WO | WO 94/03114 A1 | 2/1994 |
| WO | WO 95/10218 A1 | 4/1995 |
| WO | WO 95/32663 A1 | 12/1995 |
| WO | WO 01/54560 A3 | 8/2001 |
| WO | WO 02/09801 A1 | 2/2002 |
| WO | WO 02/078767 A2 | 10/2002 |
| WO | WO 03/007783 A2 | 1/2003 |
| WO | 03068083 | 8/2003 |
| WO | 2004021899 | 3/2004 |
| WO | 2004022108 | 3/2004 |
| WO | 2004103188 | 12/2004 |
| WO | 2005018466 | 3/2005 |
| WO | 2005032358 | 4/2005 |
| WO | 2005046492 | 5/2005 |
| WO | 2005096968 | 10/2005 |

* cited by examiner

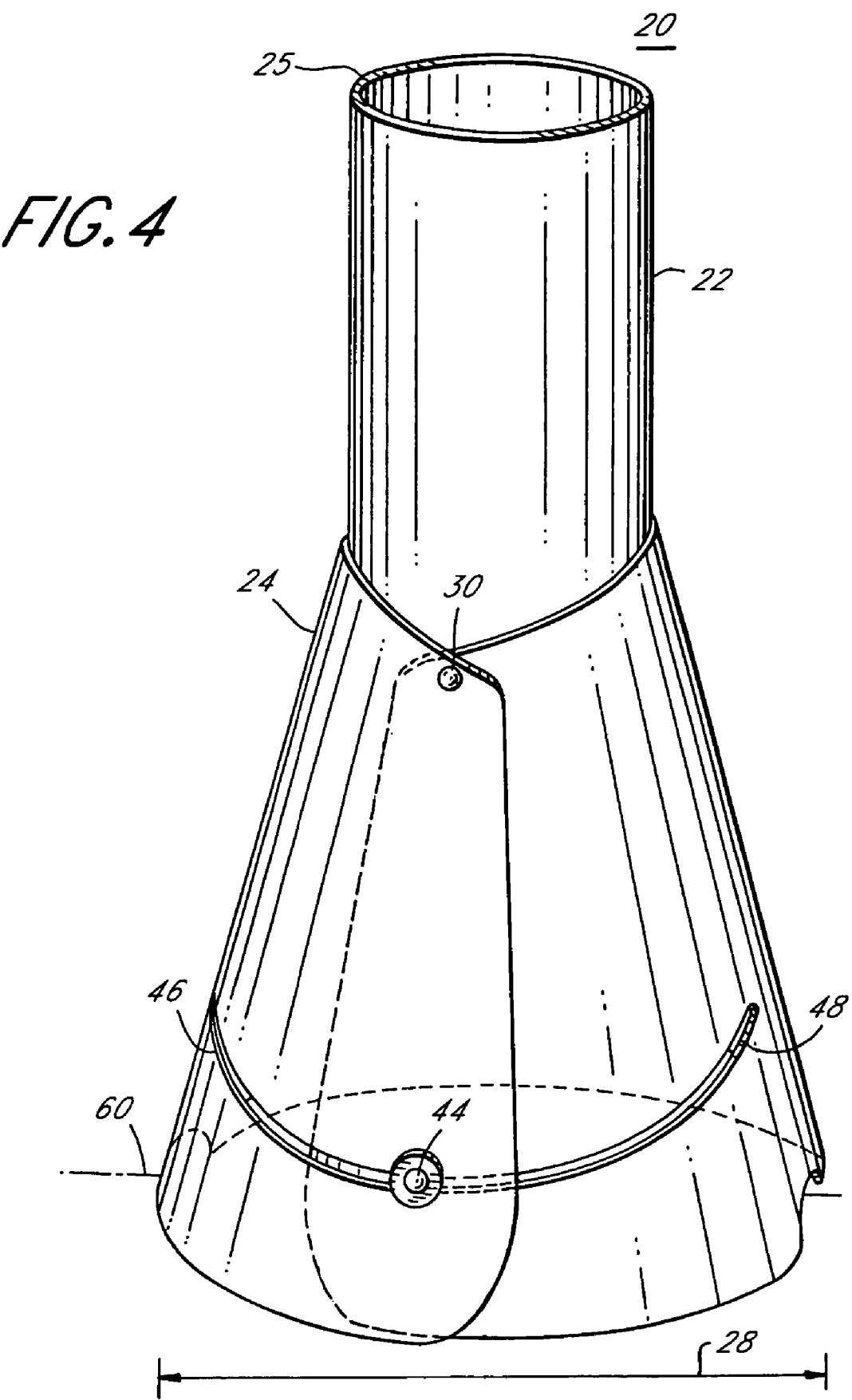

FIG. 13
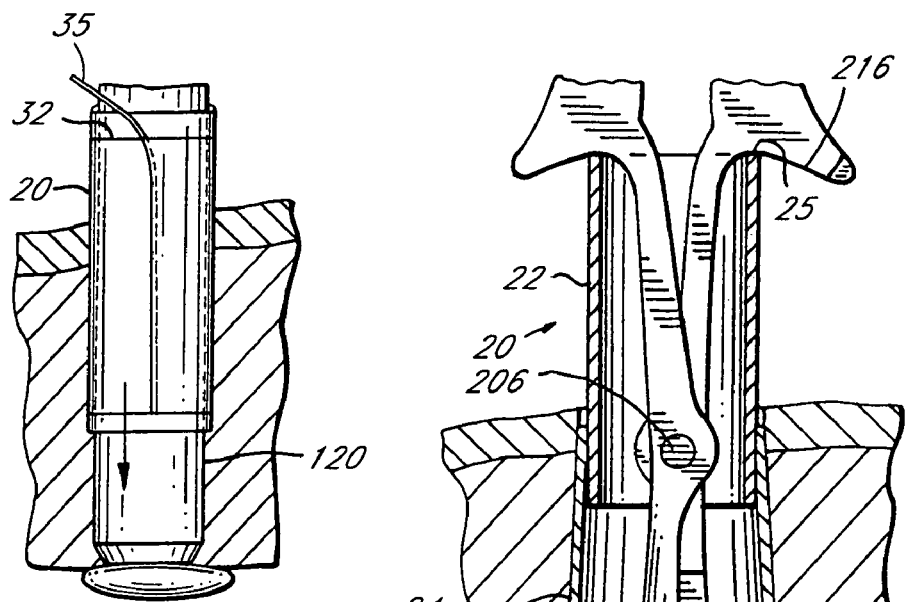
FIG. 16
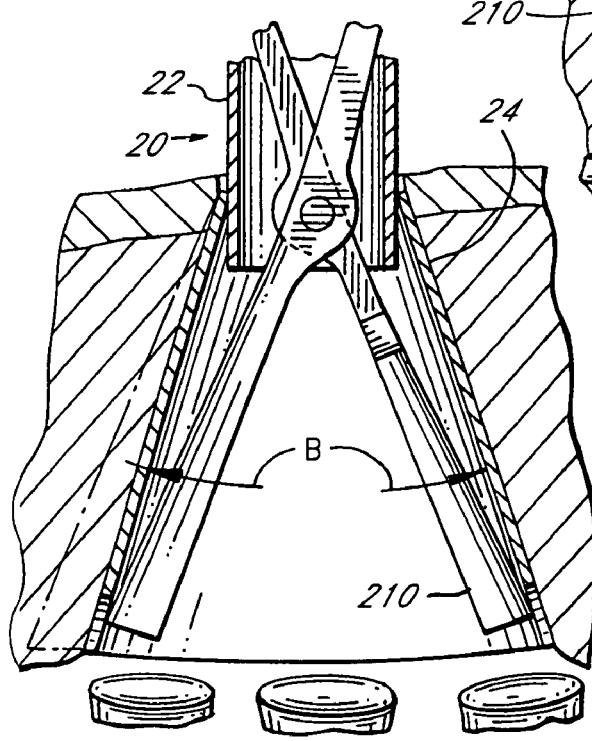
FIG. 17

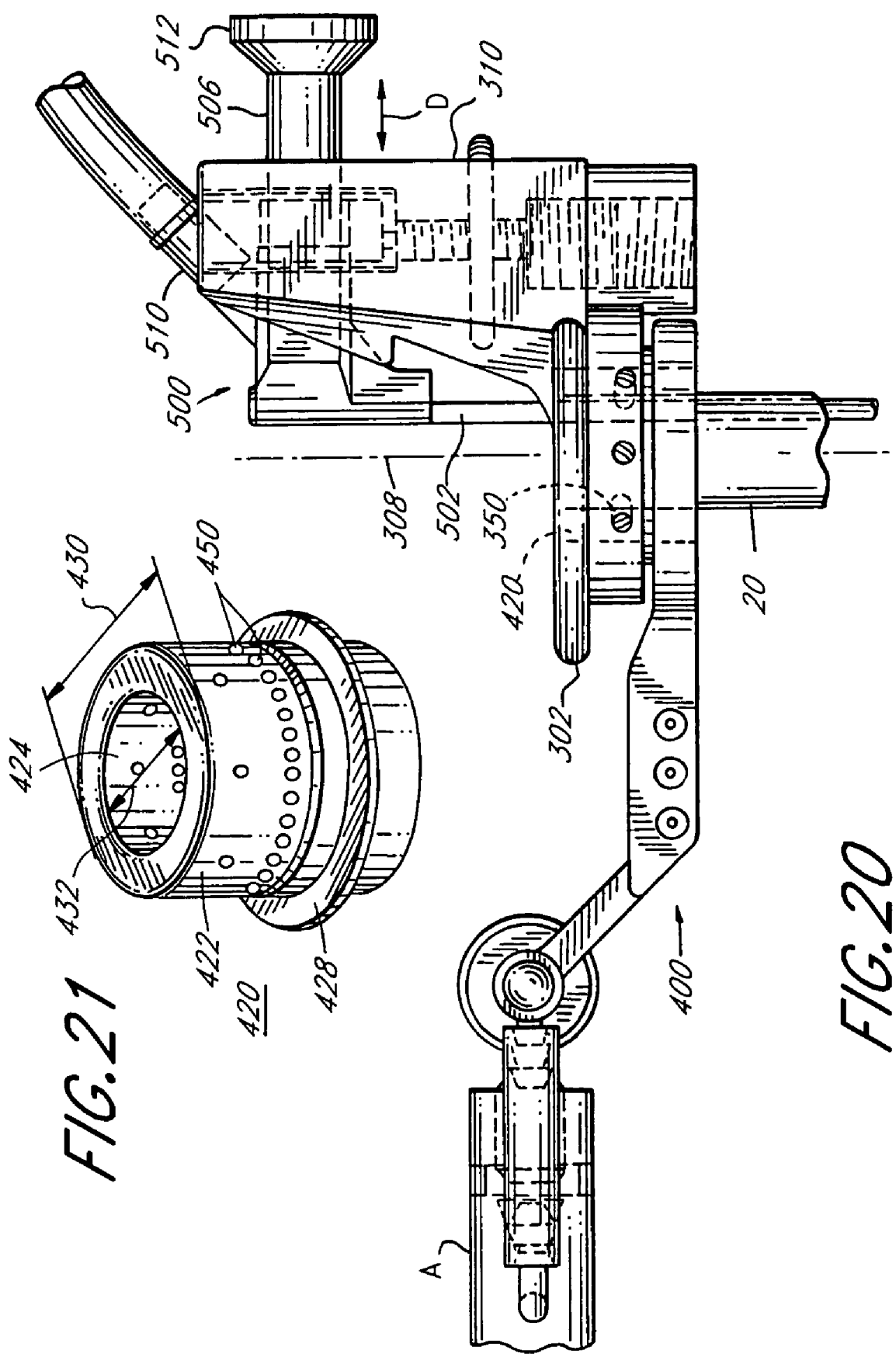

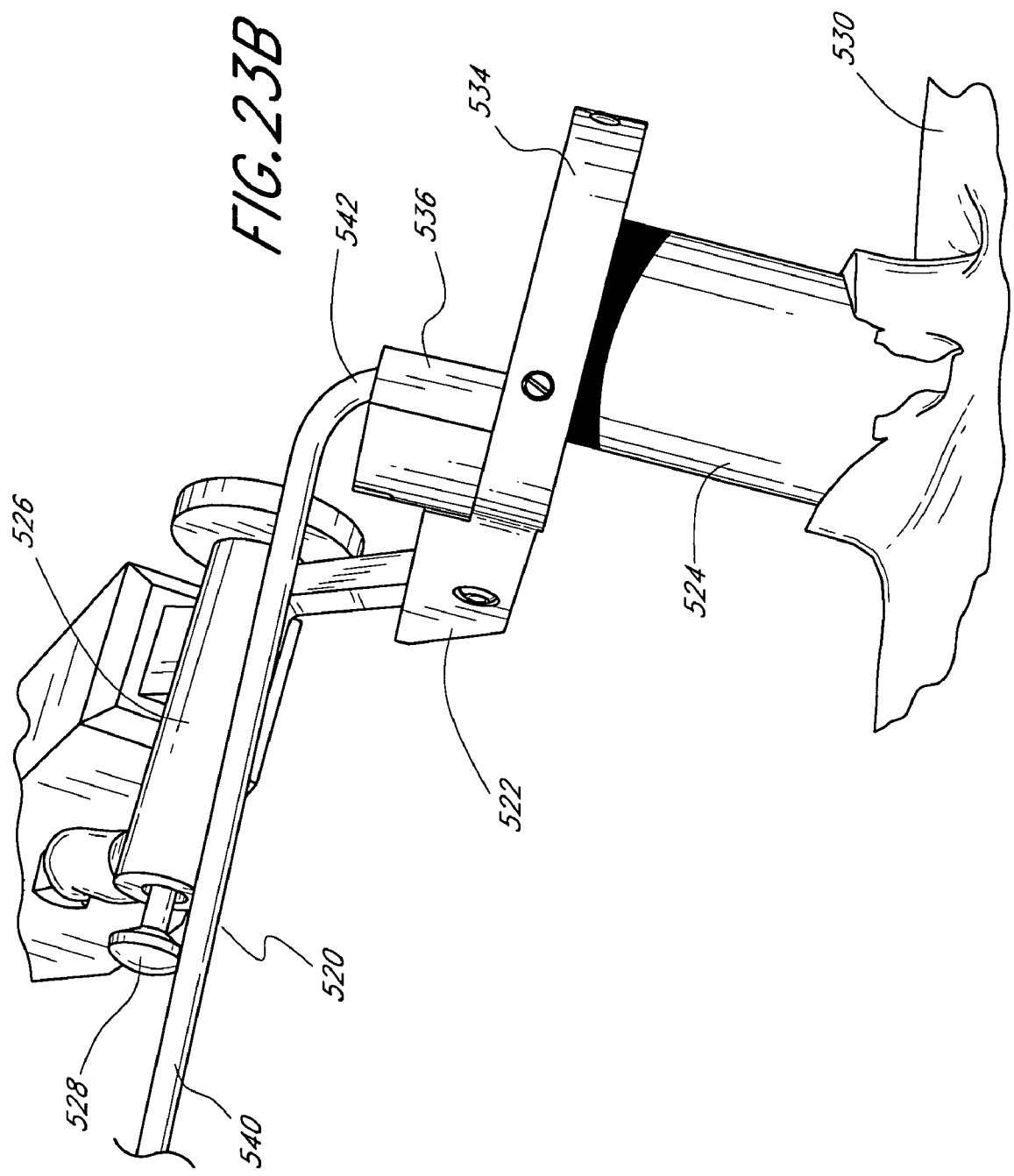

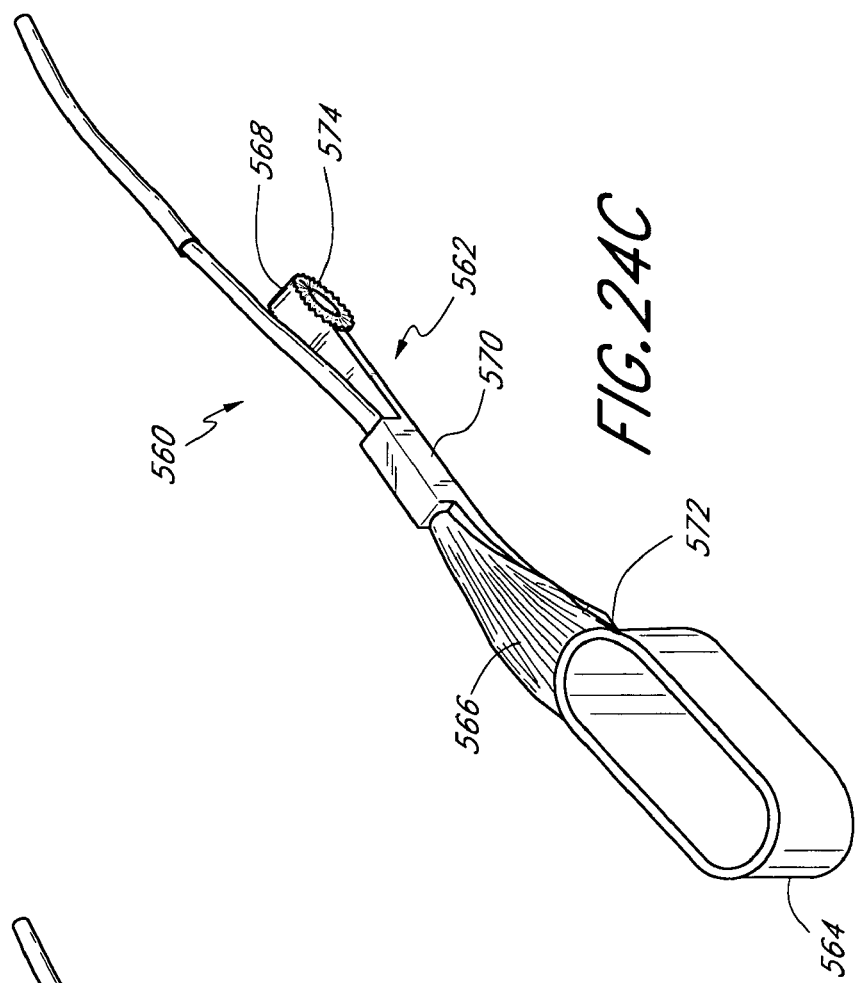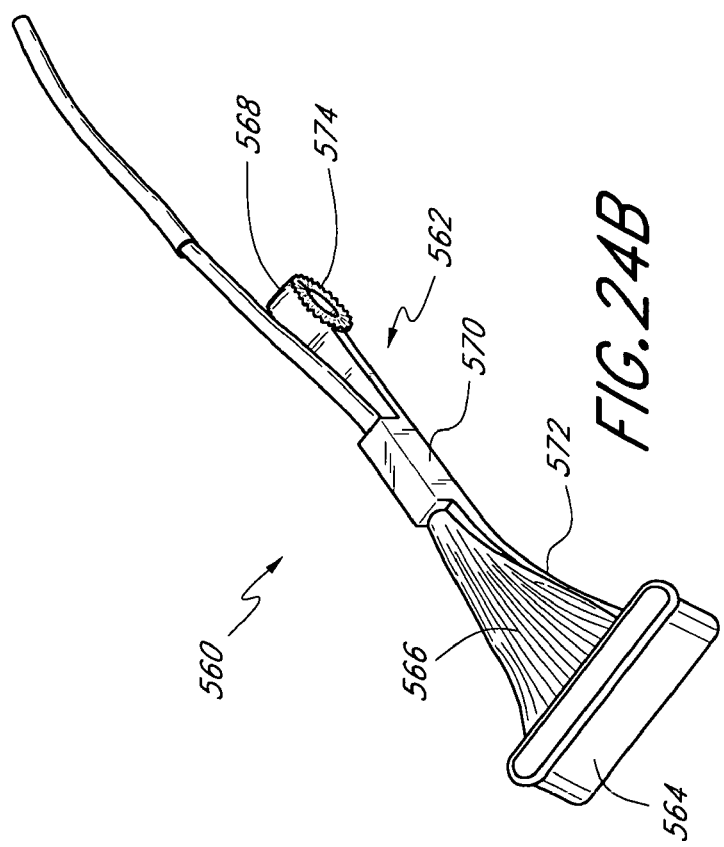

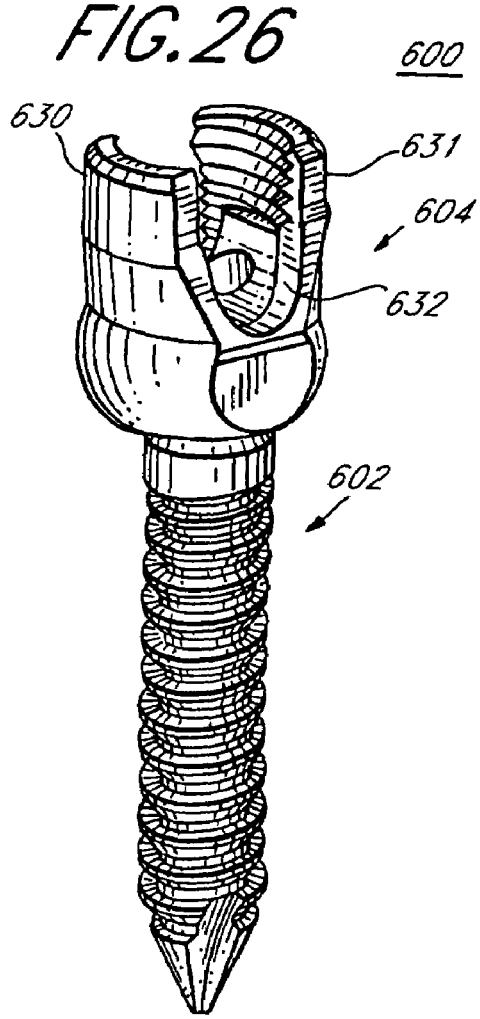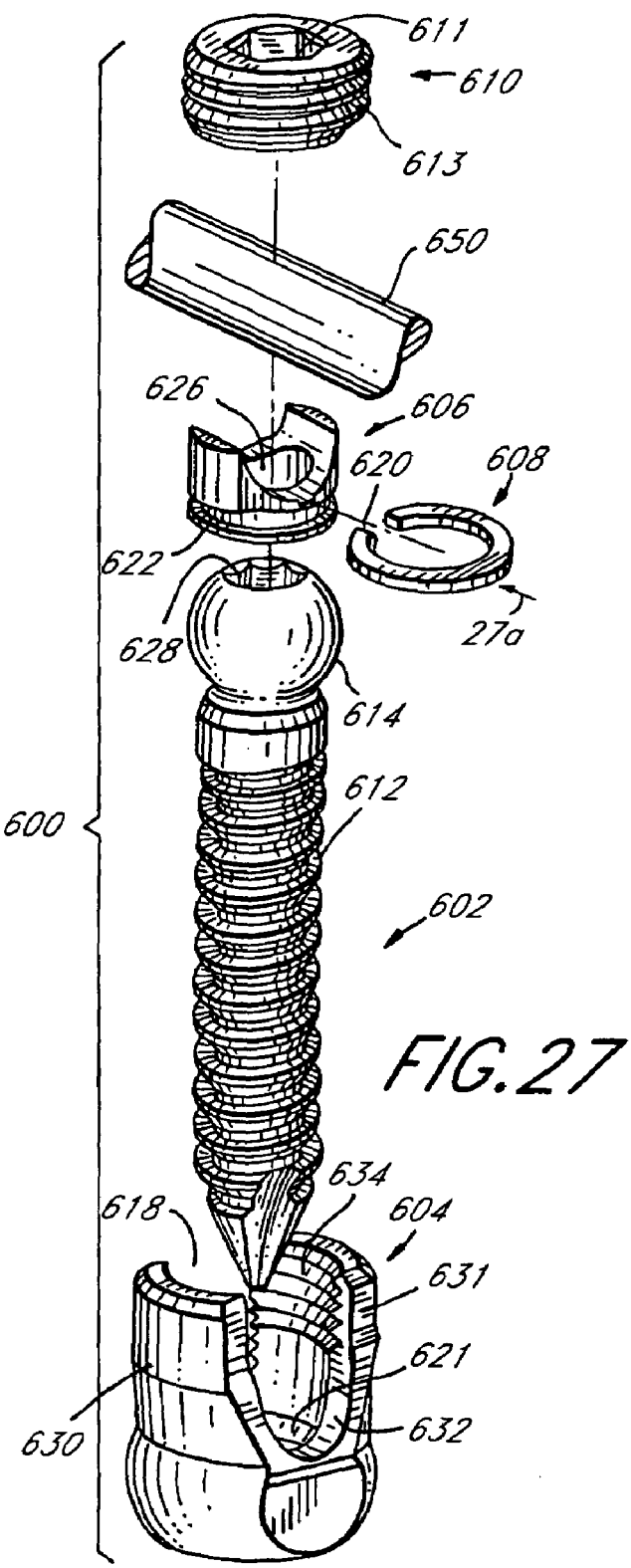

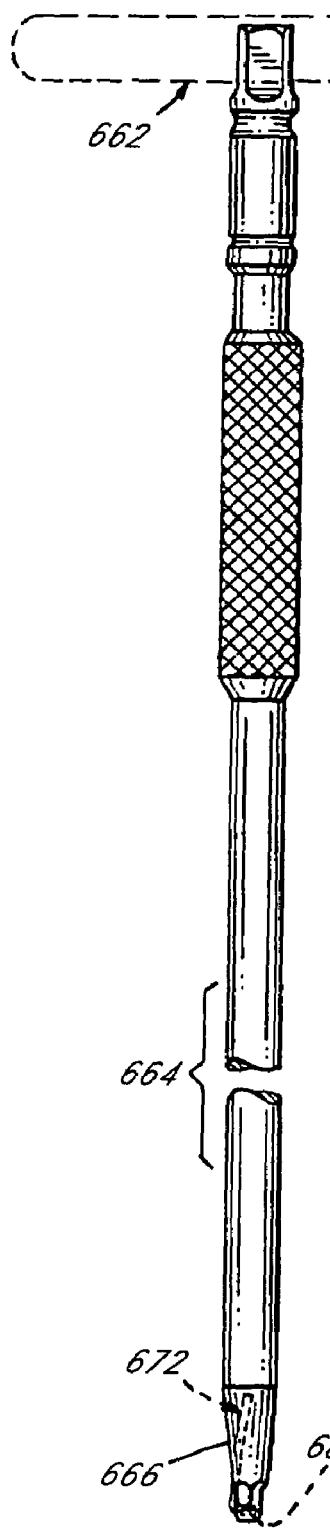
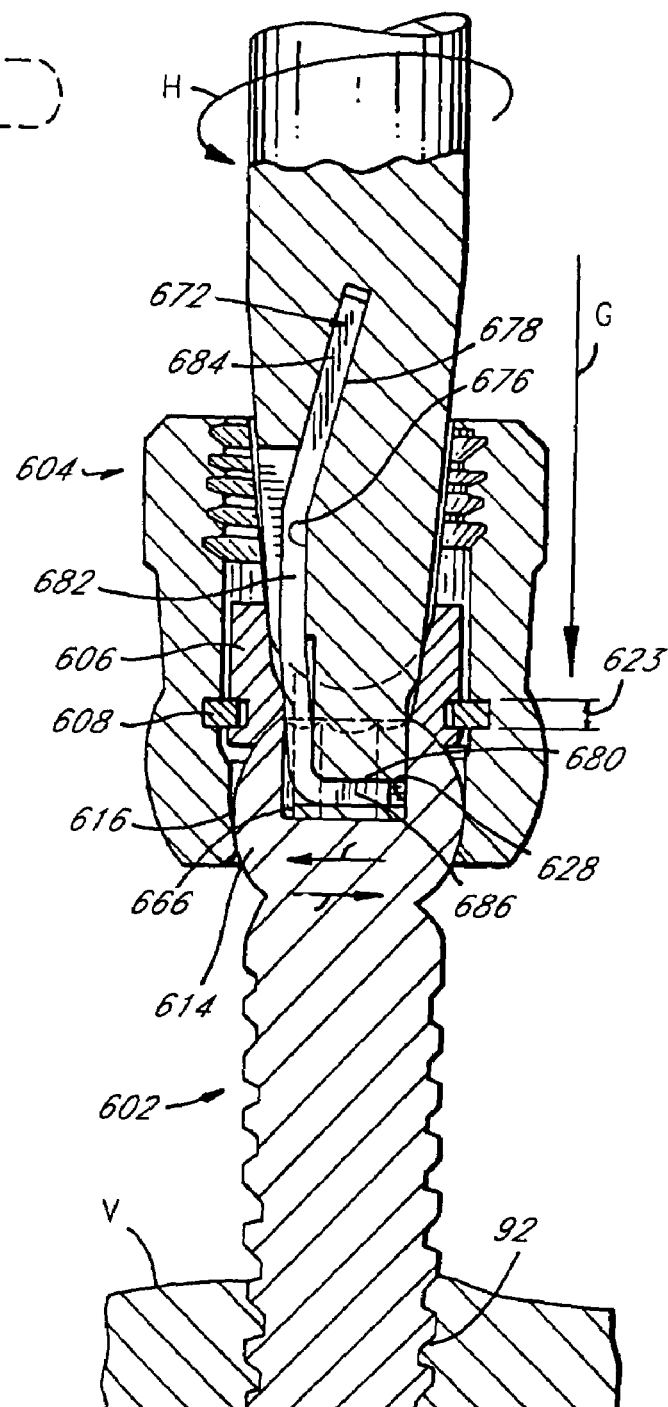

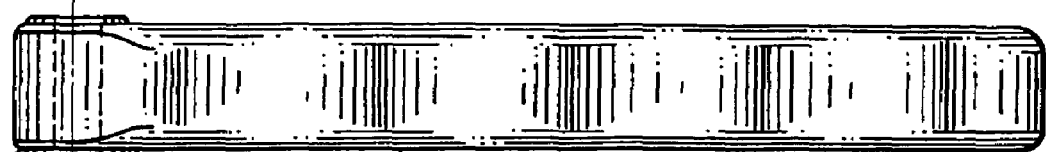
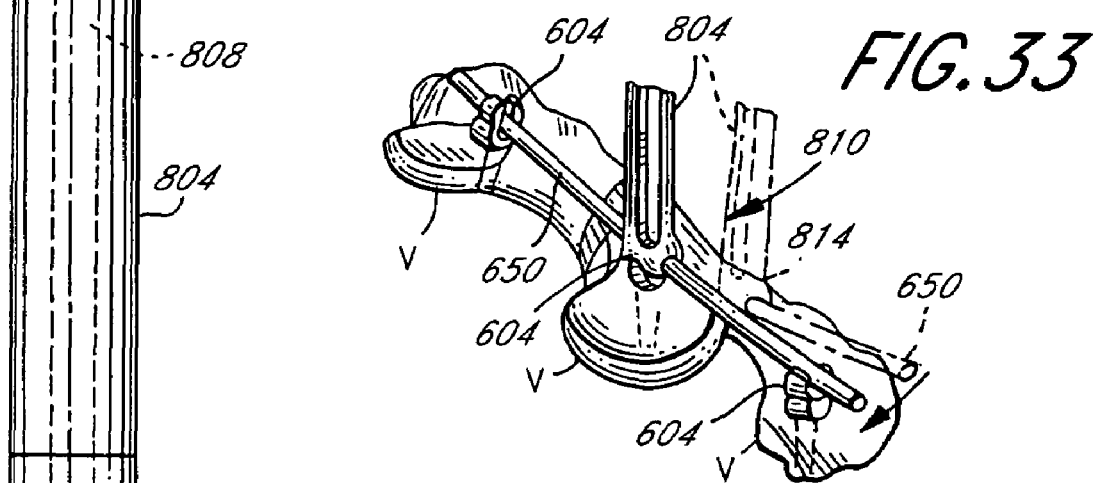
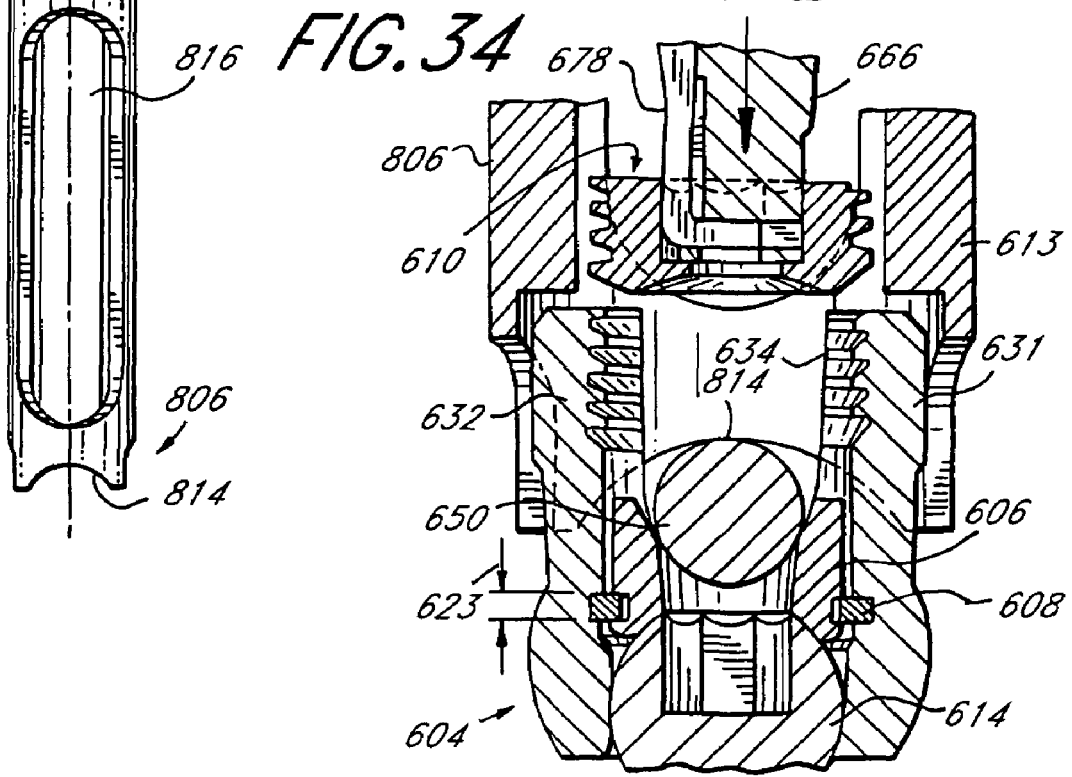

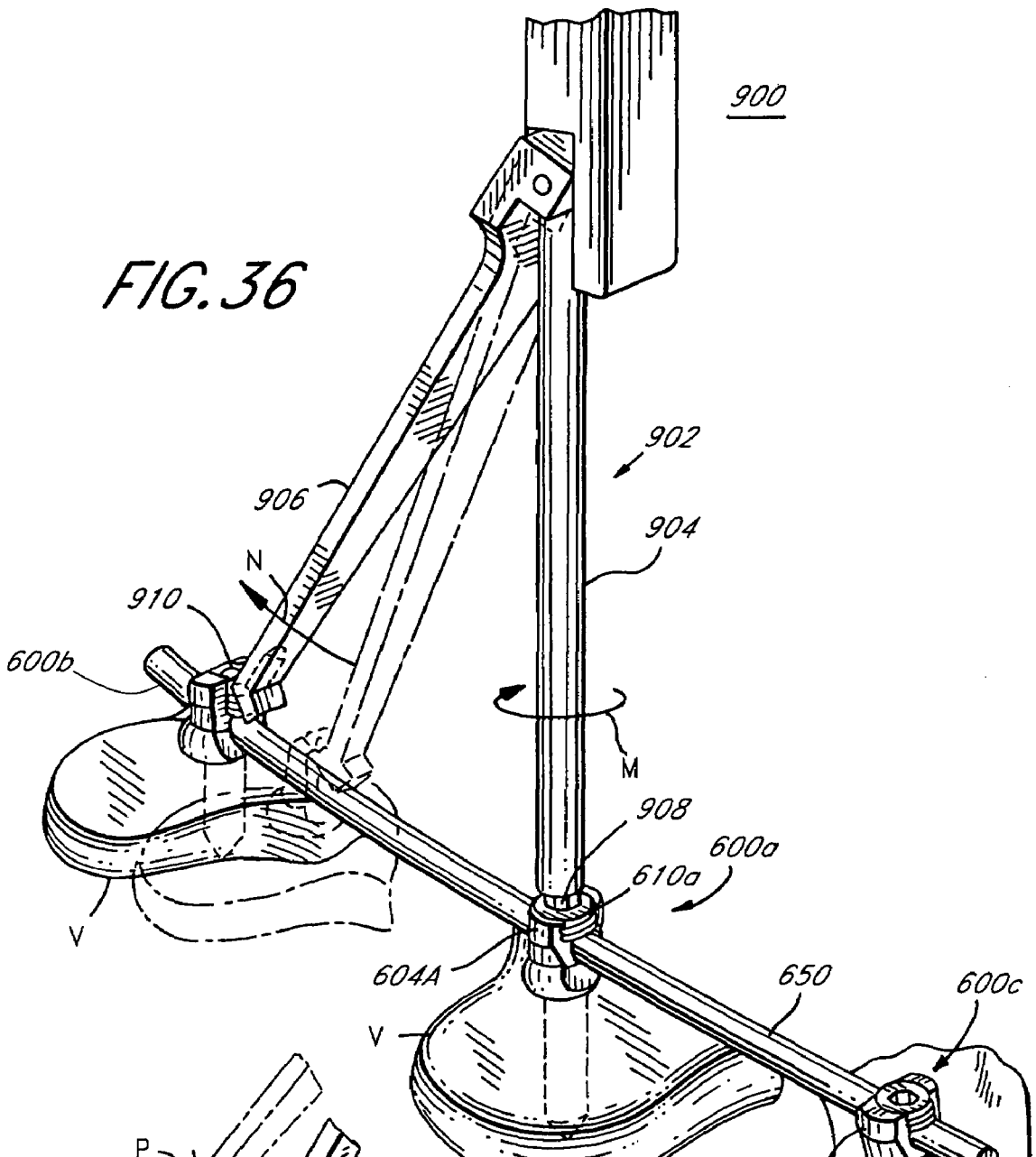
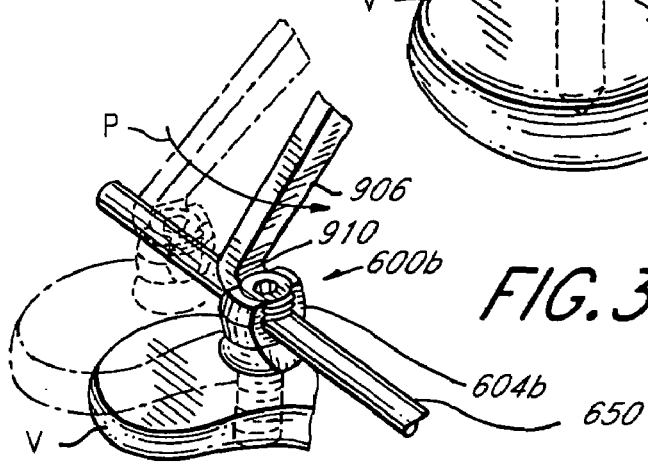

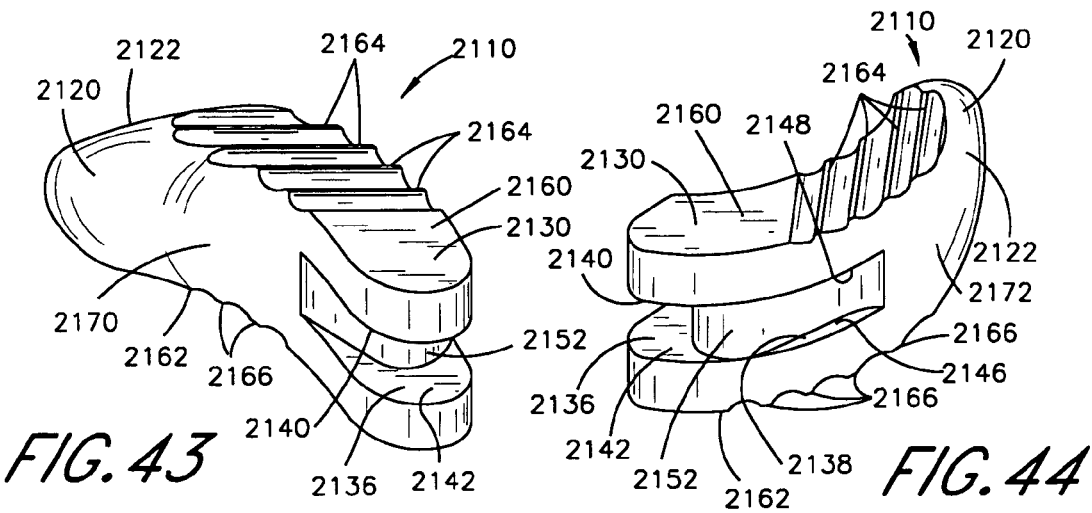
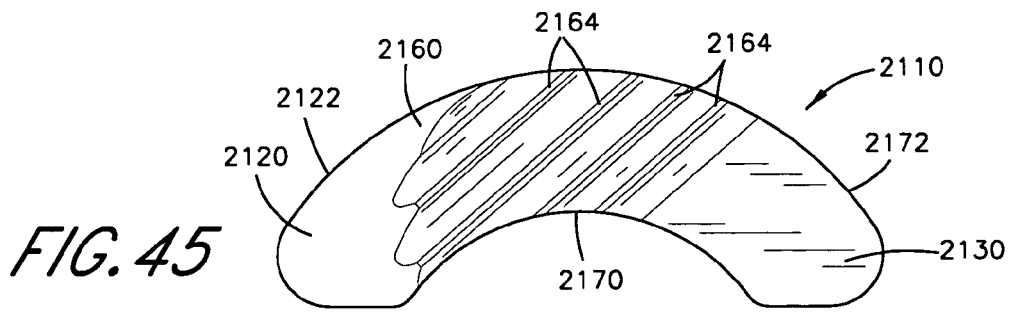
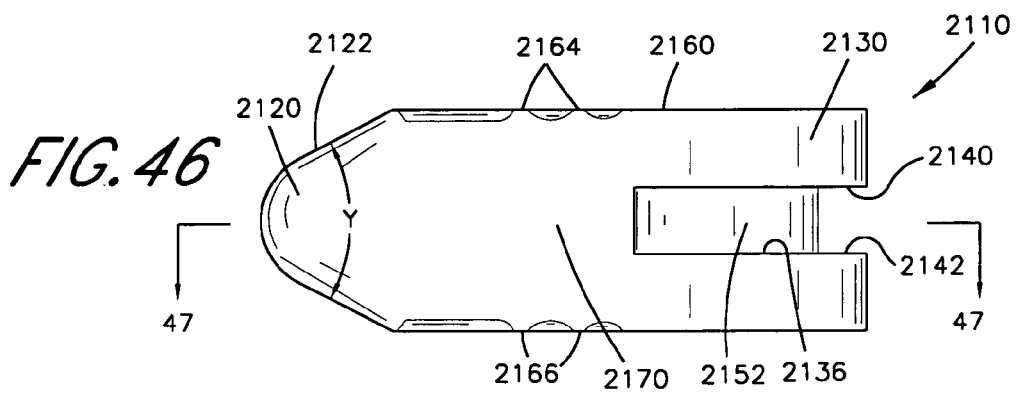
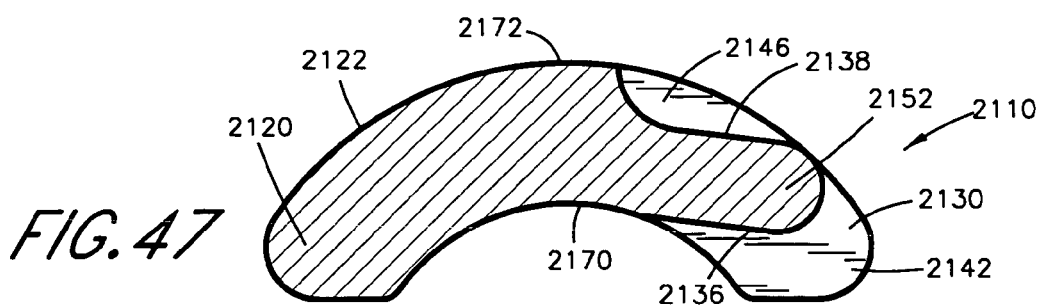

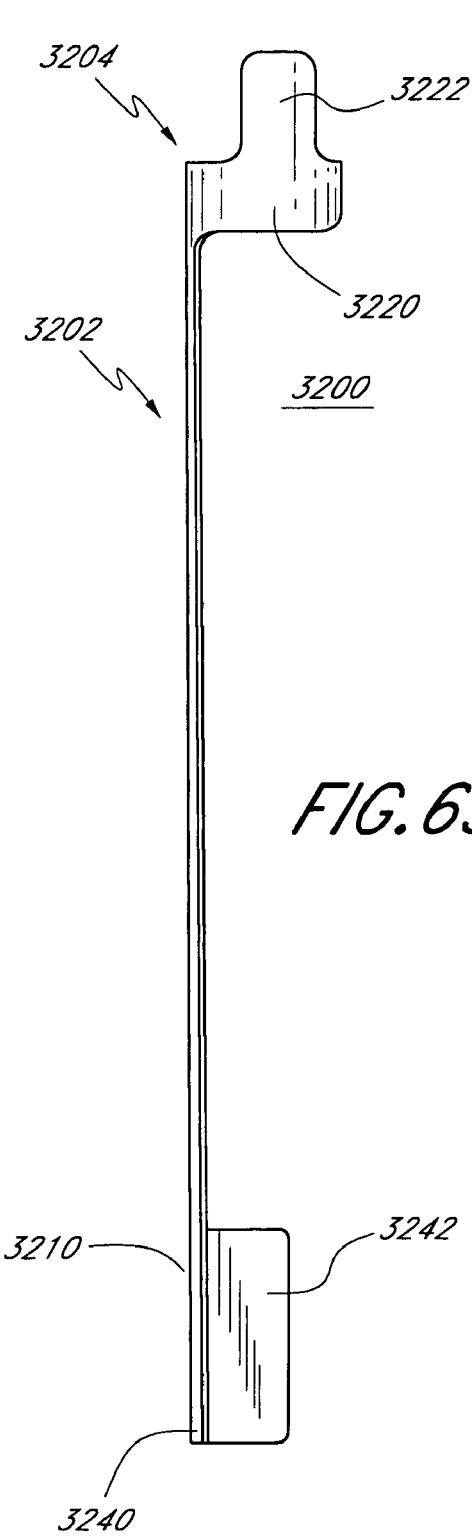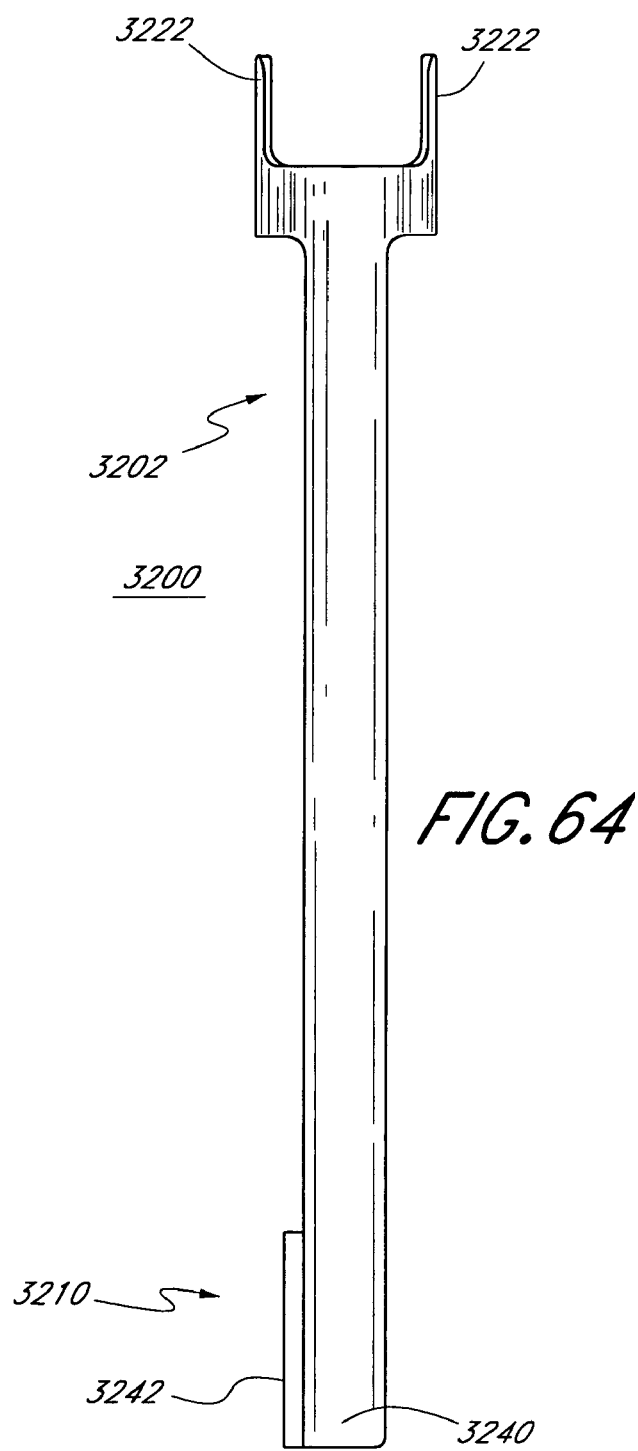
FIG. 63
FIG. 64

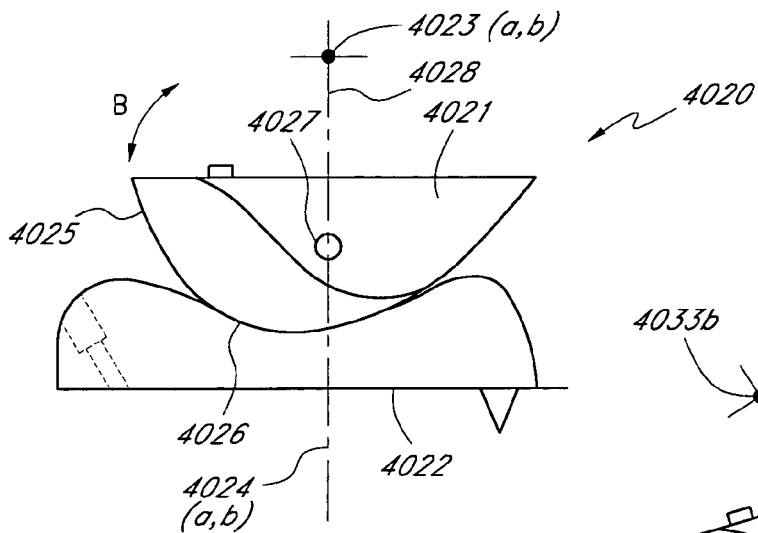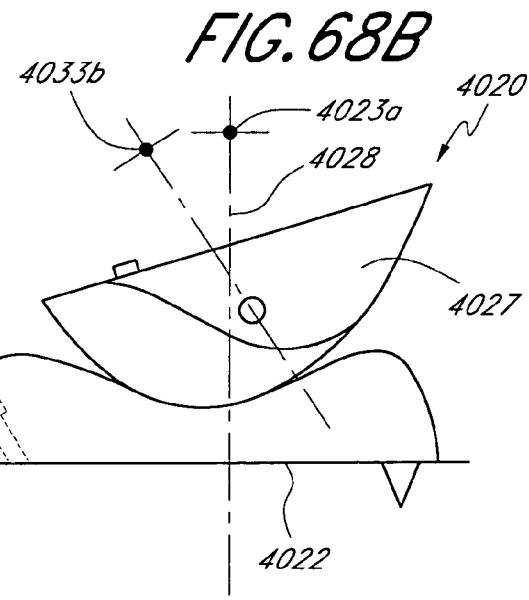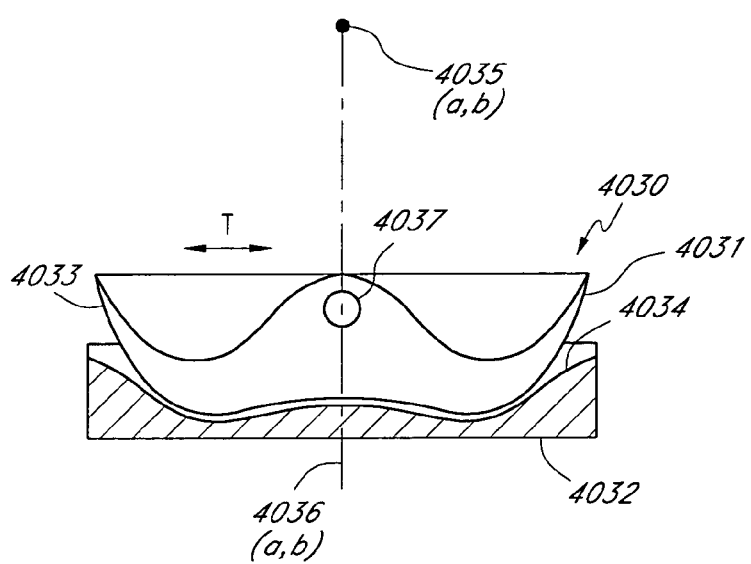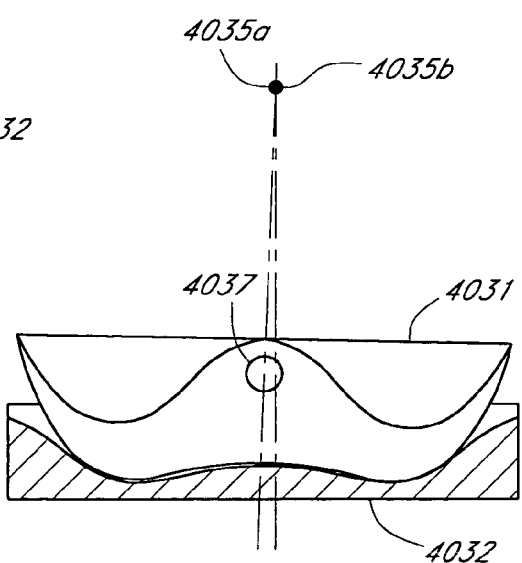
FIG. 68A
FIG. 68B
FIG. 69A
FIG. 69B

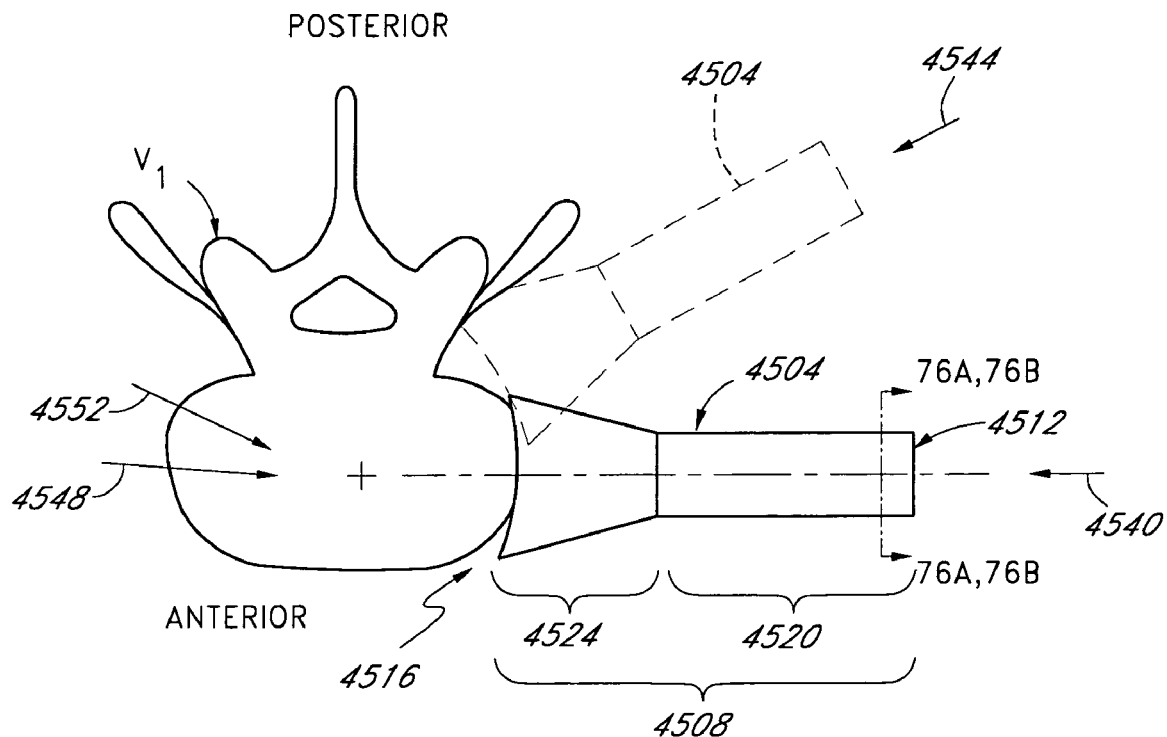
FIG. 76
FIG. 76A
FIG. 76B

METHODS AND APPARATUSES FOR MINIMALLY INVASIVE REPLACEMENT OF INTERVERTEBRAL DISCS

RELATED APPLICATIONS

This application claims priority under 35 U.S.C. §119(e) to U.S. Provisional Application No. 60/508,784, filed on Oct. 2, 2003, the entirety of which is hereby incorporated by reference.

BACKGROUND OF THE INVENTION

1. Field of the Invention

This application relates to minimally invasive surgical procedures, and more particularly to replacing an intervertebral disc of a patient with a prosthetic device.

2. Description of the Related Art

Chronic back pain can have any of a number of causes or a combination of causes. For example, acute damage to and/or progressive degeneration of a disc, which is located in the interbody space defined between adjacent vertebrae, can lead to pain as the load-bearing and flexibility providing functions of the disc are no longer effectively performed. A number of treatments have been proposed for this condition. Fusion is a procedure whereby a graft intended to promote bone growth within the interbody space replaces some or all of the material in the interbody space. The bone growth causes the adjacent vertebrae to be joined together, after which the two vertebrae essentially become one and flexibility is eliminated. Fixation is another common treatment which involves attaching a structural assembly across two adjacent vertebrae to physically join the vertebrae together to prevent relative motion of the two vertebrae with respect to each other. While these approaches can reduce the pain associated with disc conditions, the substantial reduction or complete elimination of flexibility at the problem disc can lead to greater stress on adjacent discs and other spine problems.

Traditionally, these and other spine treatments have been performed by way of open surgery. In open surgery, the surgeon typically makes one ore more large incisions and cuts and/or strips muscle tissue surrounding the spine in order to access the vertebrae. Because the amount of tissue exposed is so great, care must be taken not to injure nerve tissue in the area. Consequently, these traditional surgical procedures carry high risks of scarring, pain, significant blood loss, and extended recovery times.

Apparatuses for performing minimally invasive techniques have been proposed to reduce the trauma of spine surgery by reducing the size of the incision and the degree of muscle stripping in order to access the vertebrae. One such apparatus provides a constant diameter cannula which is made narrow in order to provide a small entry profile. As a result, the cannula provides minimal space for the physician to observe the body structures and manipulate surgical instruments in order to perform the required procedures. A narrow cannula is typically too small to perform most spine procedures. Accordingly, several cannula are required to perform even the simplest procedure.

SUMMARY OF THE INVENTION

In one embodiment, an access device is inserted through an incision in skin of a patient. The access device is expanded from a first configuration to a second configuration, the second configuration having an enlarged cross-sectional area at a distal portion of said access device such that the distal portion extends across at least a portion of the interbody space. A prosthetic spinal disc implant is then delivered through the access device.

BRIEF DESCRIPTION OF THE DRAWINGS

Further objects, features and advantages of the invention will become apparent from the following detailed description taken in conjunction with the accompanying figures showing illustrative embodiments of the invention, in which:

FIG. 4 is a perspective view of the access device of FIG. 2 in a second enlarged configuration.

FIG. 13 is a sectional view illustrating one stage of one application for treating the spine of a patient.

FIG. 16 is a sectional view of the expander apparatus of FIGS. 14-15 inserted into the access device of FIG. 2, which has been inserted into a patient.

FIG. 17 is a sectional view of the expander apparatus of FIGS. 14-15 inserted into the access device of FIG. 2 and expanded to the expanded configuration to retract tissue.

FIG. 20 is a side view of the endoscope mount platform of FIG. 18 illustrated with one embodiment of an indexing arm and one embodiment of an endoscope.

FIG. 21 is a perspective view of one embodiment of an indexing collar of the endoscope mount platform FIG. 18.

FIG. 23B is a side perspective view of the access system of FIG. 23A.

FIG. 24B is a perspective view of another embodiment of a lighting element.

FIG. 24C is a perspective view of another embodiment of a lighting element.

FIG. 26 is a perspective view of one embodiment of a fastener.

FIG. 27 is an exploded perspective view of the fastener of FIG. 26.

FIG. 27A is an enlarged side view of one embodiment of a biasing member illustrated in FIG. 27 taken from the perspective of the arrow 27A.

FIG. 28 is a perspective view of one embodiment of a surgical instrument.

FIG. 29 is an enlarged sectional view of the fastener of FIGS. 26-27 coupled with the surgical instrument of FIG. 28, illustrating one stage of one application for treating the spine of a patient.

FIG. 32 is a side view of one embodiment of another surgical instrument.

FIG. 33 is a perspective view similar to FIG. 31 illustrating the apparatuses of FIGS. 26 and 32, in one stage of one application for treating the spine of a patient.

FIG. 34 is an enlarged sectional view of the apparatus of FIGS. 26 and 32, illustrating one stage of one application for treating the spine of a patient.

FIG. 36 is an enlarged view in partial section illustrating one stage of one application for treating the spine of a patient.

FIG. 37 is a partial view of illustrating one stage of one application for treating the spine of a patient.

FIG. 43 is a perspective view of another embodiment of a spinal implant constructed according to another embodiment showing a first side surface of the spinal implant.

FIG. 44 is a perspective view of the spinal implant of FIG. 43 showing a second side surface of the spinal implant.

FIG. 45 is a plan view of the spinal implant of FIG. 43 showing an upper surface of the spinal implant.

FIG. 46 is a side view of the spinal implant of FIG. 43 showing the first side surface.

FIG. 47 is a cross-sectional view of the spinal implant taken along the line 47-47 in FIG. 46.

FIG. 63 is a side view, similar to FIG. 52, of another apparatus.

FIG. 64 is a front view, similar to FIG. 55, of the embodiment of FIG. 63.

FIGS. 68A and 68B are side elevation views of the spinal implant illustrated by FIGS. 66A-67C wherein the first and second portions are depicted in two different stages of articulation.

FIGS. 69A and 69B are partial cross-sectional rear elevation views of the implant illustrated in FIGS. 66A-67C wherein the first and second portions are depicted in two different stages of articulation.

FIG. 76 is a schematic view of one surface of a vertebra that defines one end of an interbody space and one embodiment of an access device configured to provide access to the interbody space.

FIG. 76A is a cross-section view of a proximal portion of one embodiment of the access device of FIG. 76.

FIG. 76B is a cross-section view of a proximal portion of another embodiment of the access device of FIG. 76.

Figure 1:
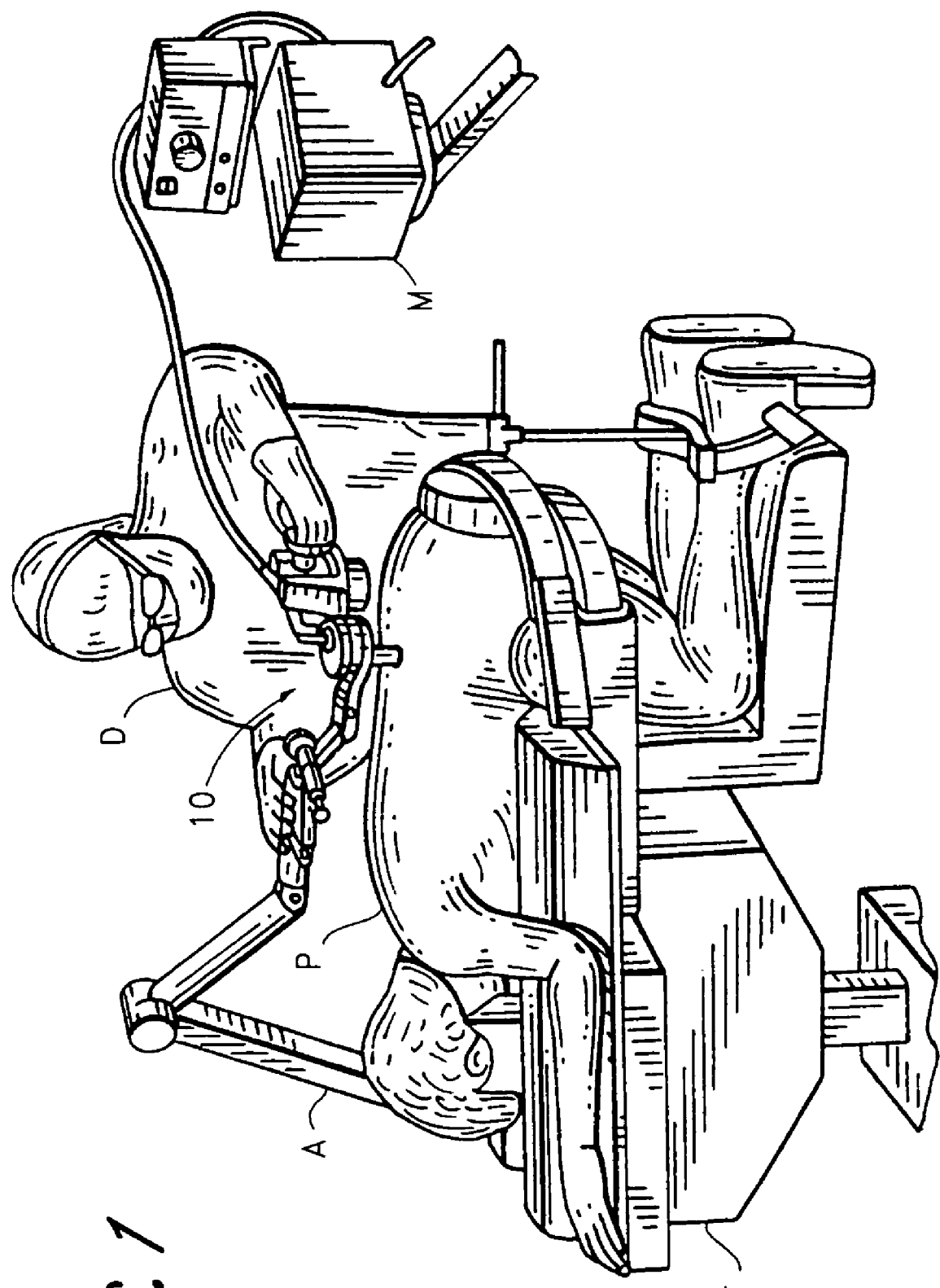
FIG. 1 is a perspective view of one embodiment of a surgical system and one application for treating the spine of a patient.
Figure 2:
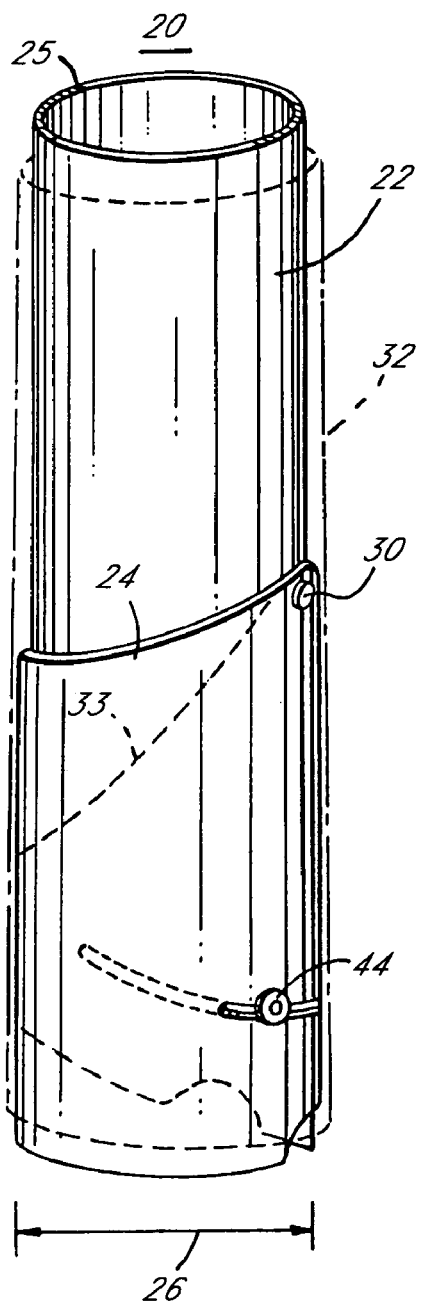
FIG. 2 is a perspective view of one embodiment of an access device in a reduced profile configuration.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF THE PREFERRED EMBODIMENTS

As should be understood in view of the following detailed description, this application is primarily directed to apparatuses and methods providing access to and for treating the spine of a patient. The apparatuses described below provide access to surgical locations at or near the spine and provide a variety of tools useful treating the spine. In particular, various embodiments described hereinbelow include access devices that are particularly well adapted to be coupled with one or more viewing elements. In some embodiments, access devices are provided that are configured to receive one or more viewing elements at discrete locations about a passage defined by the access device. The apparatuses described herein enable a surgeon to perform a wide variety of methods of treatment as described herein.

I. Systems for Performing Procedures at a Surgical Location

Various embodiments of apparatuses and procedures described herein will be discussed in terms of minimally invasive procedures and apparatuses, e.g., of endoscopic apparatuses and procedures. However, various embodiments may find use in conventional, open, and mini-open procedures. As used herein, the term "proximal," as is traditional, refers to the end portion of an apparatus that is closest to the operator, while the term "distal" refers to the end portion that is farthest from the operator.

FIG. 1 shows one embodiment of a surgical system 10 that can be used to perform a variety of methods or procedures. In one embodiment, as discussed more fully below, the patient P is placed in the prone position on operating table T, taking care that the abdomen is not compressed and physiological lordosis is preserved. The physician D is able to access the surgical site and perform the surgical procedure with the components of the system 10, which will be described in greater detail herein. The system 10 may be supported, in part, by a mechanical support arm A, such as the type generally disclosed in U.S. Pat. No. 4,863,133, which is hereby incorporated by reference herein in its entirety. One mechanical arm of this type is manufactured by Leonard Medical, Inc., 1464 Holcomb Road, Huntington Valley, Pa., 19006. The mechanical support arm A is sometimes referred to as a "flex arm." As discussed in greater detail below, the mechanical support arm A is coupled with at least one of an access device and a viewing element.

The term "access device" is used in its ordinary sense to mean a device that can provide access and is a broad term and it includes structures having an elongated dimension and defining a passage, e.g., a cannula or a conduit. The access device is configured to be inserted through the skin of the patient to provide access during a surgical procedure to a surgical location within a patient, e.g., a spinal location. The term "surgical location" is used in its ordinary sense (i.e. a location where a surgical procedure is performed) and is a broad term and it includes locations subject to or affected by a surgery. The term "spinal location" is used in its ordinary sense (i.e. a location at or near a spine) and is a broad term and it includes locations adjacent to or associated with a spine that may be sites for surgical spinal procedures. The access device also can retract tissue to provide greater access to the surgical location. The term "retractor" is used in its ordinary sense to mean a device that can displace tissue and is a broad term and it includes structures having an elongated dimension and defining a passage, e.g., a cannula or a conduit, to retract tissue.

Visualization of the surgical site may be achieved in any suitable manner, e.g., by direct visualization, or by use of a viewing element, such as an endoscope, a camera, loupes, a microscope, or any other suitable viewing element, or a combination of the foregoing. The term "viewing element" is used in its ordinary sense to mean a device useful for viewing and is a broad term and it also includes elements that enhance viewing, such as, for example, a light source or lighting element. In one embodiment, the viewing element provides a video signal representing images, such as images of the surgical site, to a monitor M. The viewing element may be an endoscope and camera that captures images to be displayed on the monitor M whereby the physician D is able to view the surgical site as the procedure is being performed. The endoscope and camera will be described in greater detail herein.

The systems are described herein in connection with minimally invasive postero-lateral spinal surgery. One such procedure is a two level postero-lateral fixation and fusion of the spine involving the L4, L5, and S1 vertebrae. In the drawings, the vertebrae will generally be denoted by reference letter V. The usefulness of the apparatuses and procedures is neither restricted to the postero-lateral approach nor to the L4, L5, and S1 vertebrae. The apparatuses and procedures may be used in other anatomical approaches and with other vertebra (e) within the cervical, thoracic, and lumbar regions of the spine. The procedures may be directed toward surgery involving one or more vertebral levels. Some embodiments are useful for anterior and/or lateral procedures. A retroperitoneal approach can also be used with some embodiments. In one retroperitoneal approach, an initial transverse incision is made just left of the midline, just above the pubis, about 3 centimeters in length. The incision can be carried down through the subcutaneous tissues to the anterior rectus sheath, which is incised transversely and the rectus is retracted medially. At this level, the posterior sheath, where present, can be incised. With blunt finger dissection, the retroperitoneal space can be entered. The space can be enlarged with blunt dissection or with a retroperitoneal balloon dissector. The peritoneal sack can be retracted, e.g., by one of the access devices described herein.

It is believed that embodiments of the invention are also particularly useful where any body structures must be accessed beneath the skin and muscle tissue of the patient, and/or where it is desirable to provide sufficient space and visibility in order to manipulate surgical instruments and treat the underlying body structures. For example, certain features or instrumentation described herein are particularly usefuil for minimally invasive procedures, e.g., arthroscopic procedures. As discussed more fully below, one embodiment of an apparatus described herein provides an access device that is expandable, e.g., including an expandable distal portion. In addition to providing greater access to a surgical site than would be provided with a device having a constant cross-section from proximal to distal, the expandable distal portion prevents or substantially prevents the access device, or instruments extended therethrough to the surgical site, from dislodging or popping put of the operative site.

A. Systems and Devices for Establishing Access

In one embodiment, the system 10 includes an access device that provides an internal passage for surgical instruments to be inserted through the skin and muscle tissue of the patient P to the surgical site. The access device preferably has a wall portion defining a reduced profile, or low-profile, configuration for initial percutaneous insertion into the patient. This wall portion may have any suitable arrangement. In one embodiment, discussed in more detail below, the wall portion has a generally tubular configuration that may be passed over a dilator that has been inserted into the patient to atraumatically enlarge an opening sufficiently large to receive the access device therein.

The wall portion of the access device preferably can be subsequently expanded to an enlarged configuration, by moving against the surrounding muscle tissue to at least partially define an enlarged surgical space in which the surgical procedures will be performed. In a sense, it acts as its own dilator. The access device may also be thought of as a retractor, and may be referred to herein as such. Both the distal and proximal portion may be expanded, as discussed further below. However, the distal portion preferably expands to a greater extent than the proximal portion, because the surgical procedures are to be performed at the surgical site, which is adjacent the distal portion when the access device is inserted into the patient.

While in the reduced profile configuration, the access device preferably defines a first unexpanded configuration. Thereafter, the access device can enlarge the surgical space defined thereby by engaging the tissue surrounding the access device and displacing the tissue outwardly as the access device expands. The access device preferably is sufficiently rigid to displace such tissue during the expansion thereof. The access device may be resiliently biased to expand from the reduced profile configuration to the enlarged configuration. In addition, the access device may also be manually expanded by an expander device with or without one or more surgical instruments inserted therein, as will be described below. The surgical site preferably is at least partially defined by the expanded access device itself. During expansion, the access device can move from a first overlapping configuration to a second overlapping configuration in some embodiments.

In some embodiments, the proximal and distal portions are separate components that may be coupled together in a suitable fashion. For example, the distal end portion of the access device may be configured for relative movement with respect to the proximal end portion in order to allow the physician to position the distal end portion at a desired location. This relative movement also provides the advantage that the proximal portion of the access device nearest the physician D may remain substantially stable during such distal movement. In one embodiment, the distal portion is a separate component that is pivotally or movably coupled to the proximal portion. In another embodiment, the distal portion is flexible or resilient in order to permit such relative movement.

1. Access Devices

One embodiment of an access device is illustrated in FIGS. 2-6 and designated by reference number 20. In one embodiment, the access device 20 includes a proximal wall portion 22 that has a tubular configuration, and a distal wall portion that has an expandable skirt portion 24. The skirt portion 24 preferably is enlargeable from a reduced profile configuration having an initial dimension 26 (illustrated in FIG. 2) and corresponding cross-sectional area, to an enlarged configuration having a second dimension 28 (illustrated in FIG. 4) and corresponding cross-sectional area. In one embodiment, the skirt portion 24 is coupled to the proximal wall portion 22 with a rivet 30, pin, or similar connecting device to permit movement of the skirt portion 24 relative to the proximal wall portion 22.

Figure 3:
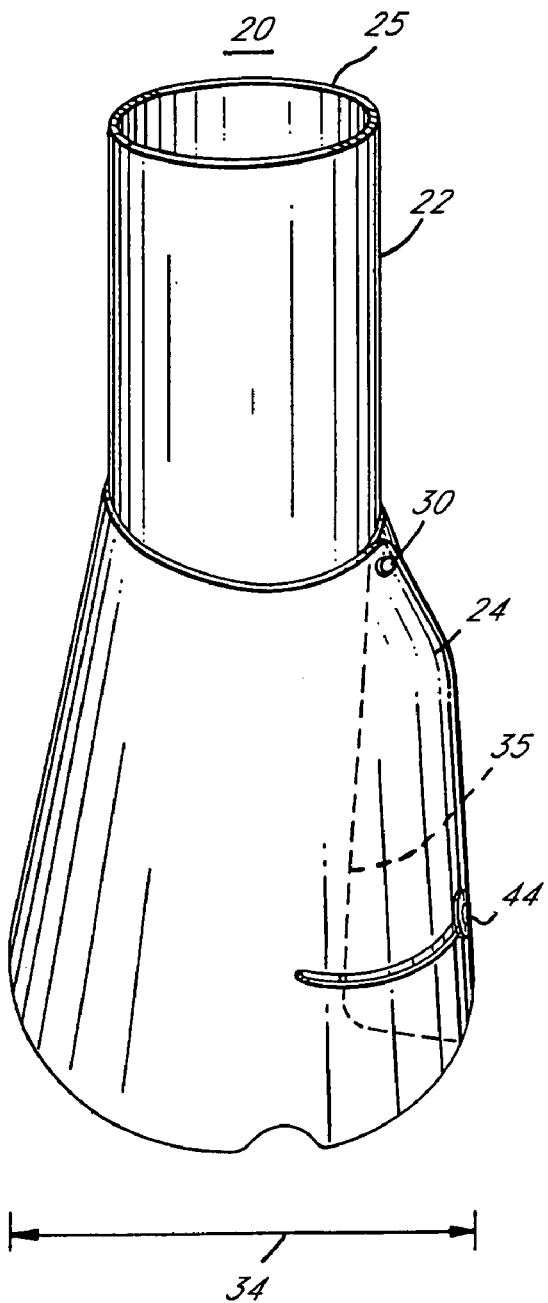
FIG. 3 is a perspective view of the access device of FIG. 2 in a first enlarged configuration.
Figure 6:
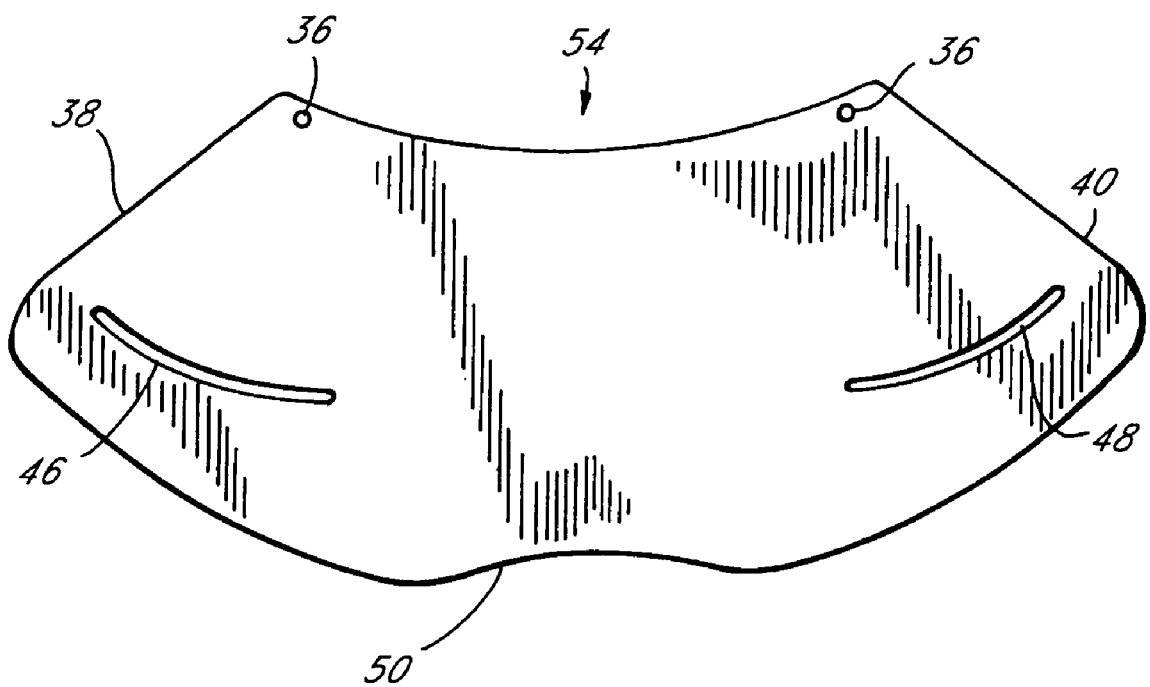
FIG. 6 is a view of another embodiment of a skirt portion of an access device.

In the illustrated embodiment, the skirt portion 24 is manufactured from a resilient material, such as stainless steel. The skirt portion 24 preferably is manufactured so that it normally assumes an expanded configuration as illustrated in FIG. 4. With reference to FIG. 3, the skirt portion 24 may assume an intermediate dimension 34 and corresponding cross-sectional area, which is greater than the initial dimension 26 of the reduced profile configuration of FIG. 2, and smaller than the dimension 28 of the enlarged configuration of FIG. 4. The skirt portion 24 may assume the intermediate configuration of FIG. 3 when deployed in the patient in response to the force of the tissue acting on the skirt portion 24. The intermediate dimension 34 can depend upon several factors, such as the rigidity of the skirt portion 24, the surrounding tissue, and whether such surrounding tissue has relaxed or tightened during the course of the procedure. An outer sleeve 32 (illustrated in dashed line in FIG. 2) may be provided. Preferably, the outer sleeve surrounds the access device 20 and maintains the skirt portion 24 in the reduced profile configuration prior to insertion into the patient. The outer sleeve 32 may be made of plastic. Where provided, the outer sleeve 32 preferably is configured to be easily deployed. For example, a release device may be provided that releases or removes the outer sleeve 32 upon being operated by the user. In one embodiment, a braided polyester suture is embedded within the sleeve 32, aligned substantially along the longitudinal axis thereof. In use, when the suture is withdrawn, the outer sleeve 32 is torn, allowing the access device 20 to resiliently expand from the reduced profile configuration of FIG. 2 to the expanded configurations of FIGS. 3-4. While in the reduced profile configuration of FIG. 2, the skirt portion 24 defines a first overlapping configuration 33, as illustrated by the dashed line. As the skirt portion 24 resiliently expands, the skirt portion 24 assumes the expanded configuration, as illustrated in FIGS. 3-4.

The skirt portion 24 preferably is sufficiently rigid that it is capable of displacing the tissue surrounding the skirt portion 24 as it expands. Depending upon the resistance exerted by surrounding tissue; the skirt portion 24 preferably is sufficiently rigid to provide some resistance against the tissue to remain in the configurations of FIGS. 3-4. Moreover, the expanded configuration of the skirt portion 24 is at least partially supported by the body tissue of the patient. The rigidity of the skirt portion 24 and the greater expansion at the distal portion preferably creates a stable configuration that is at least temporarily stationary in the patient. This arrangement preferably frees the physician from the need to actively support the access device 20, e.g., prior to adding an endoscope mount platform 300 and a support arm 400 (see FIGS. 21-22).

Figure 5:
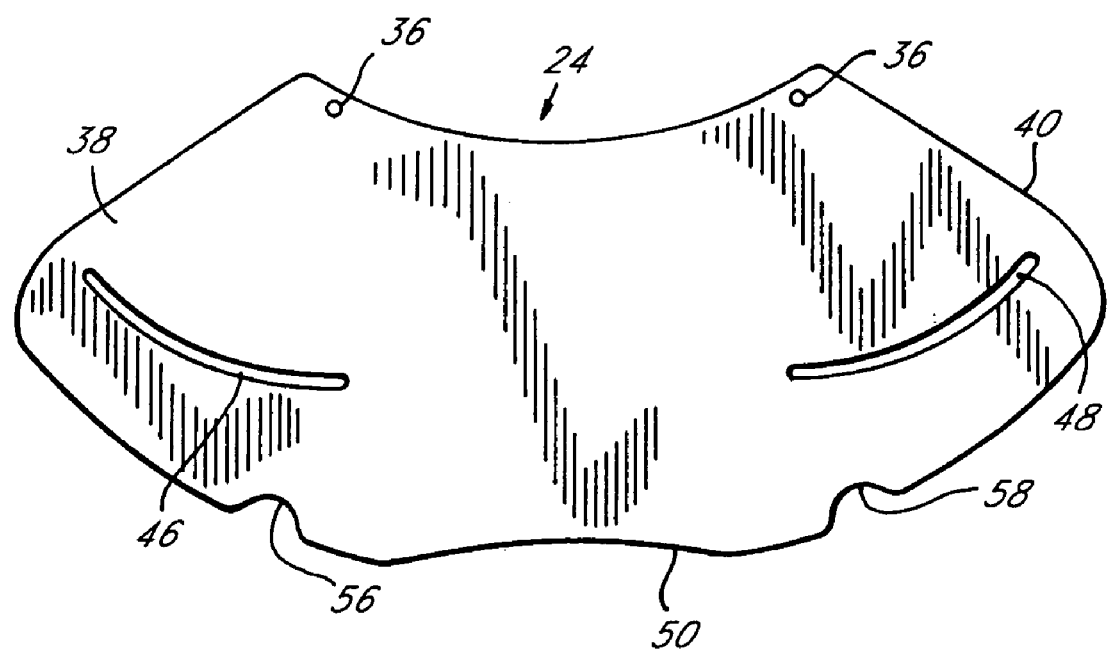
FIG. 5 is a view of one embodiment of a skirt portion of an access device.
Figure 7:
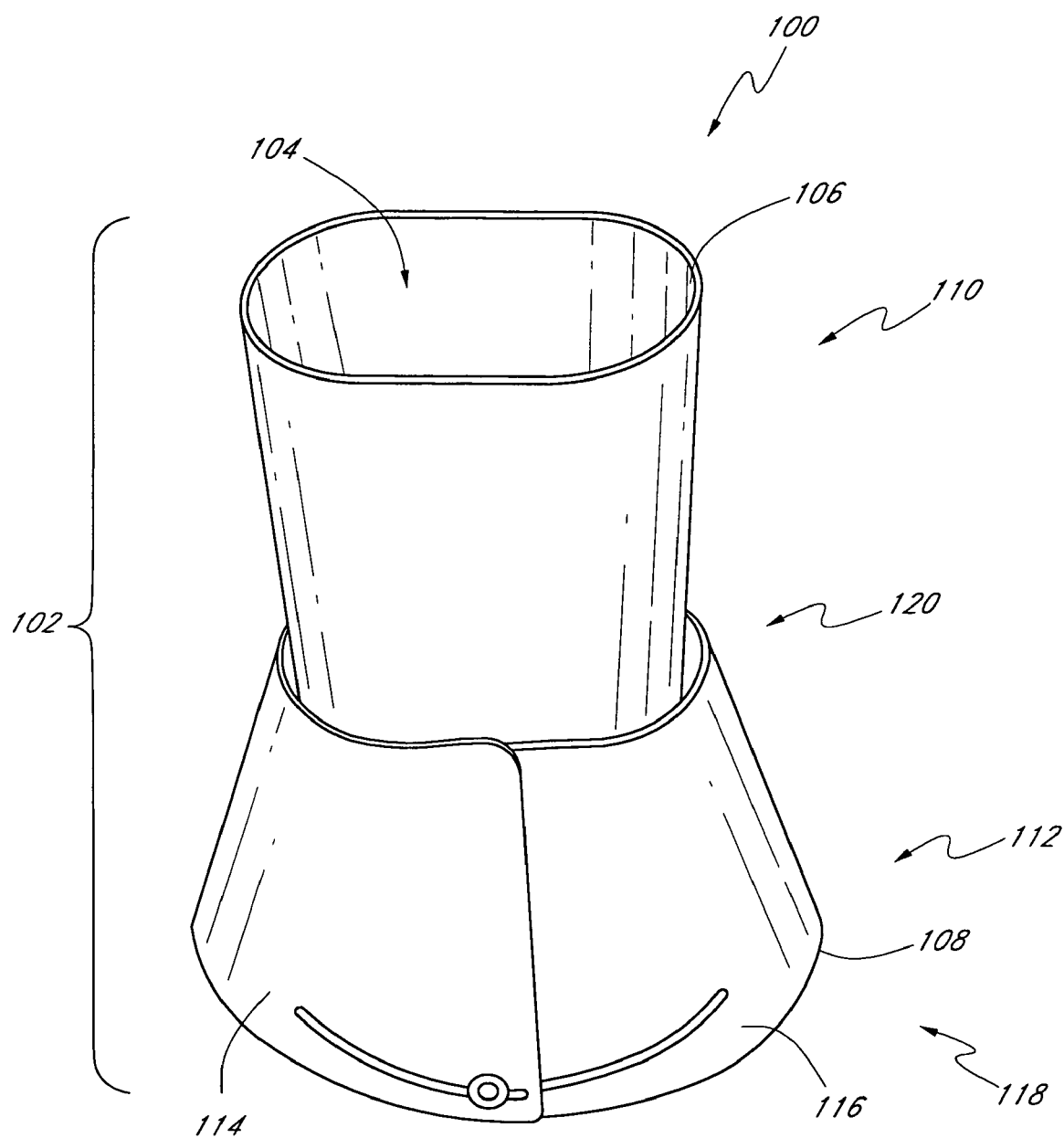
FIG. 7 is a perspective view of another embodiment of an access device.
Figure 8:
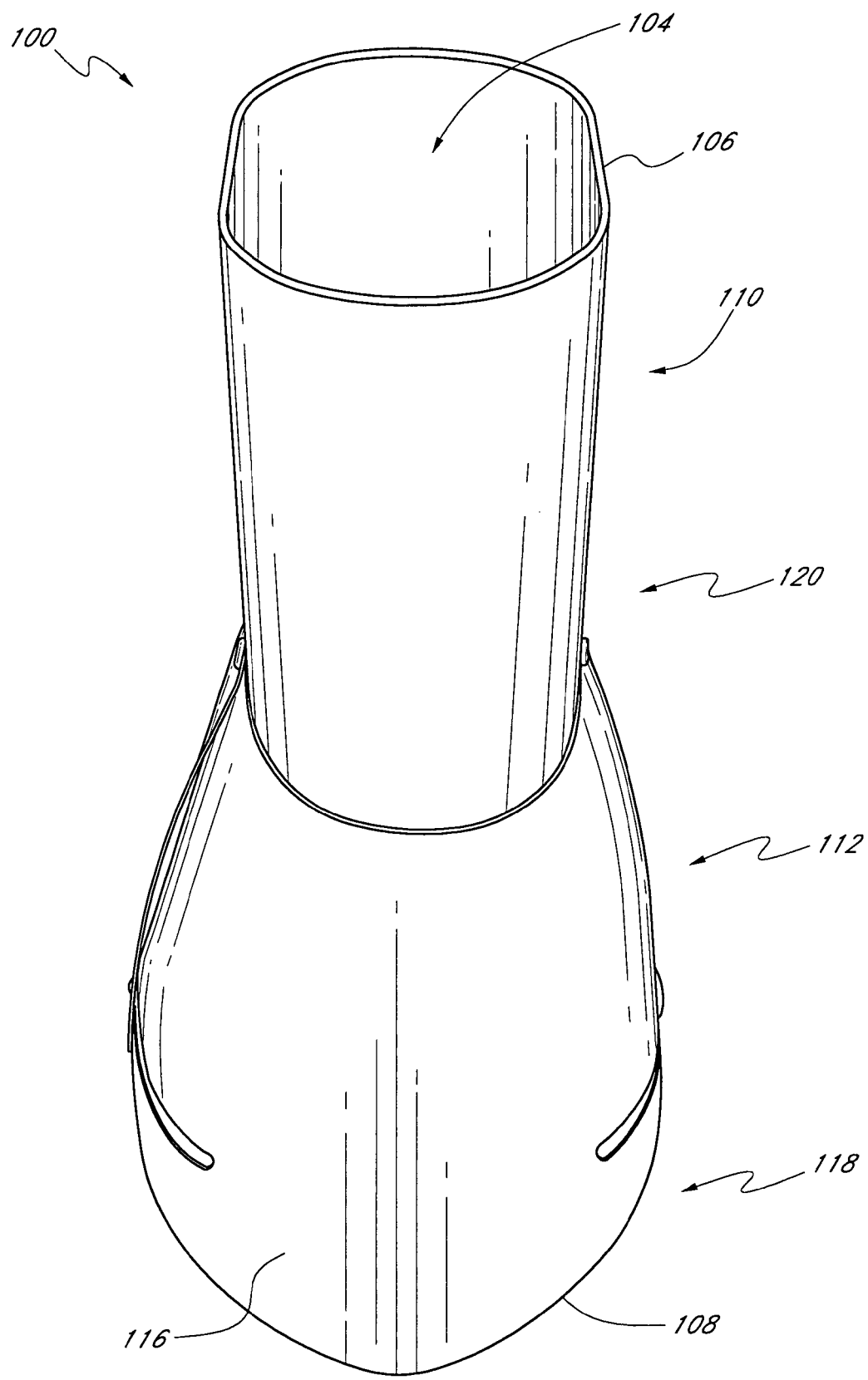
FIG. 8 is a side view of the access device of FIG. 7.
Figure 9:
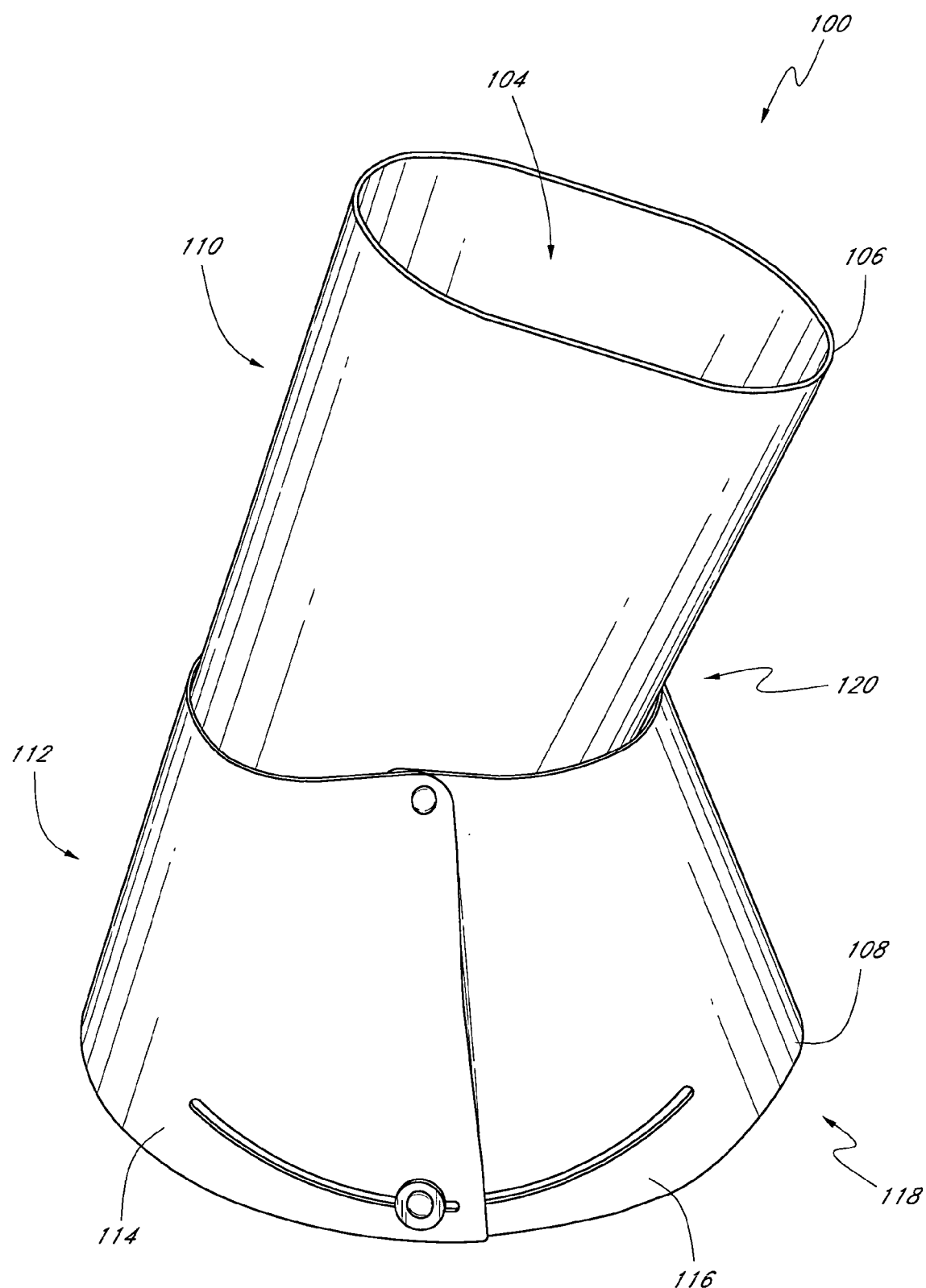
FIG. 9 is a front view of the access device of FIG. 7.
Figure 10:
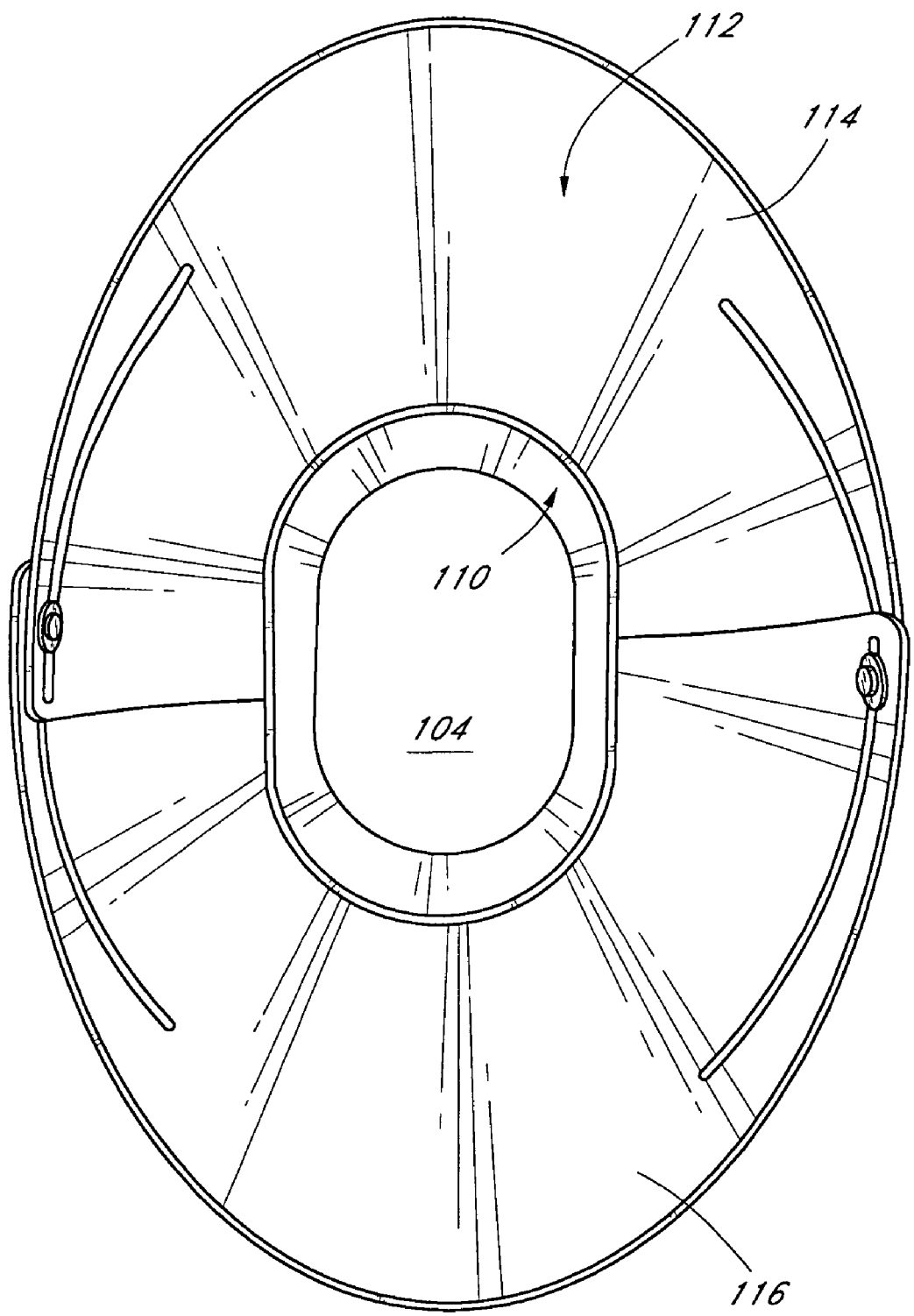
FIG. 10 is a bottom view of the access device of FIG. 7.
Figure 11:
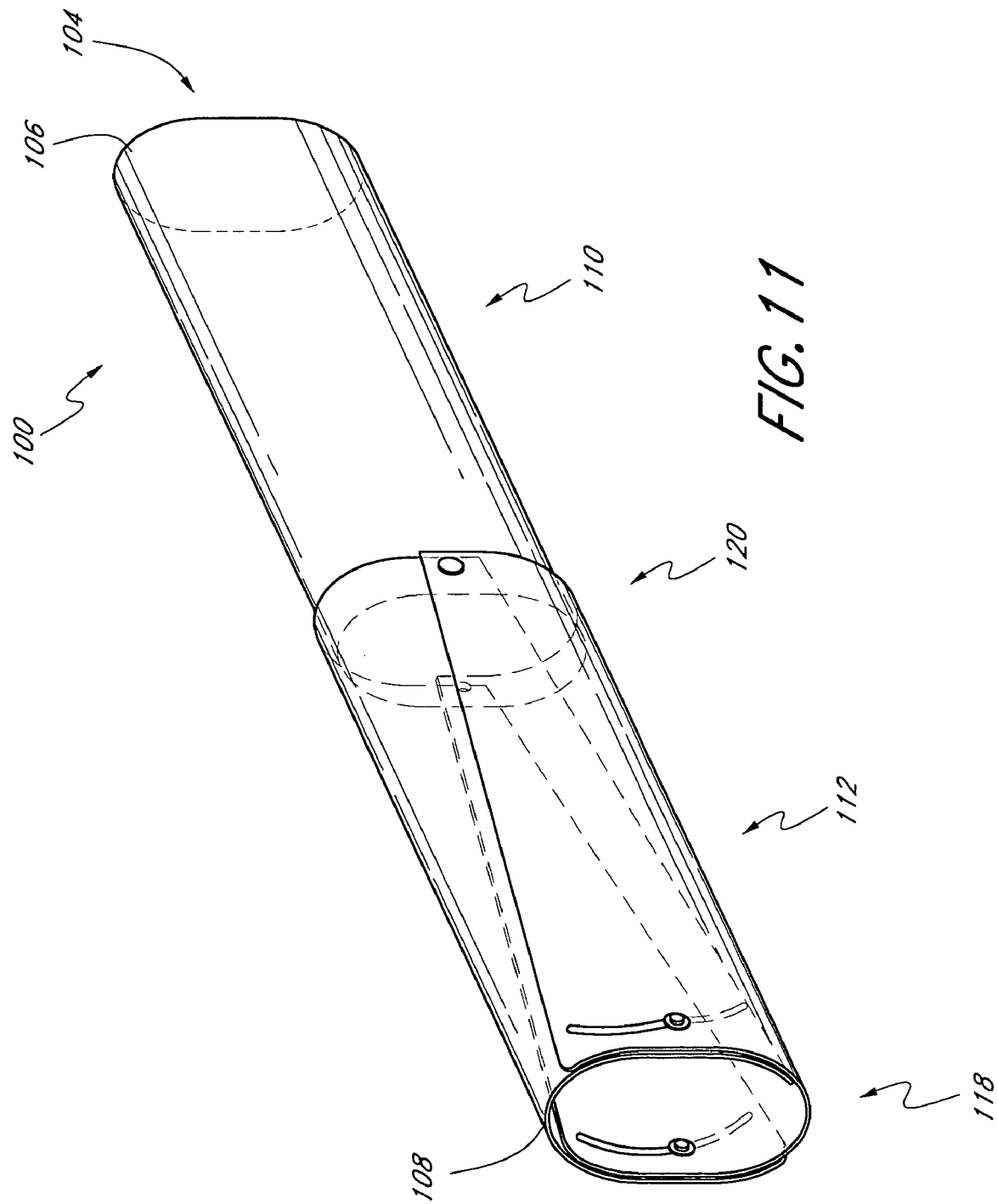
FIG. 11 is a perspective view of the access device of FIG. 7 in a first configuration.
Figure 12:
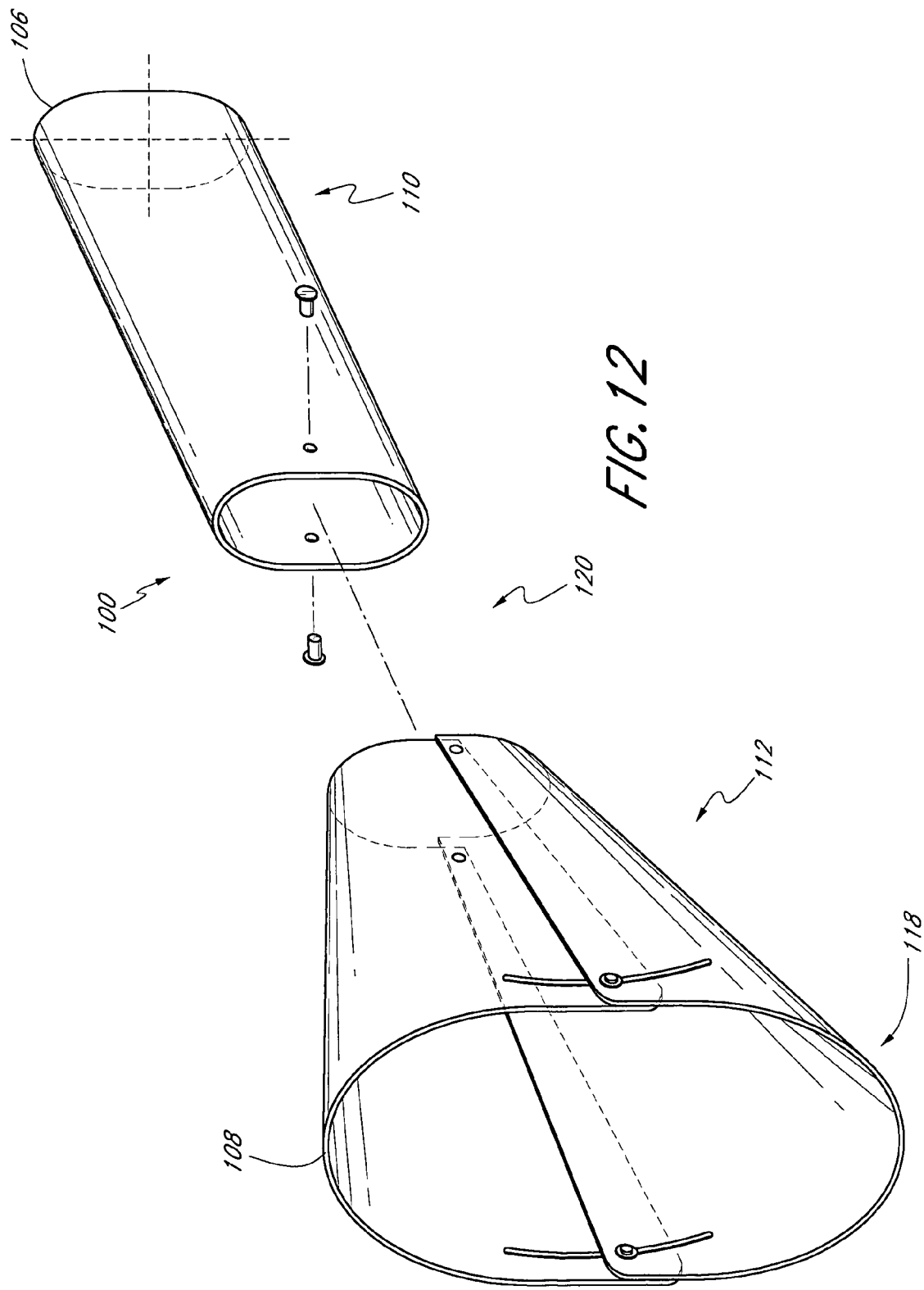
FIG. 12 is an exploded perspective view of the access device of FIG. 7 in a second configuration.

One embodiment of the skirt portion 24 of the access device 20 is illustrated in an initial flattened configuration in FIG. 5. The skirt portion 24 may be manufactured from a sheet of stainless steel having a thickness of about 0.007 inches. In various embodiments, the dimension 28 of the skirt portion 24 is about equal to or greater than 50 mm, is about equal to or greater than 60 mm, is about equal to or greater than 70 mm, is about equal to or greater than 80 mm, or is any other suitable size, when the skirt portion 24 is in the enlarged configuration. In one embodiment, the dimension 28 is about 63 mm, when the skirt portion 24 is in the enlarged configuration. The unrestricted shape of the skirt portion 24 is a circular shape in one embodiment and is an oblong shape in another embodiment. In another embodiment, the skirt portion 24 has an oval shape, wherein the dimension 28 defines a longer dimension of the skirt portion 24 and would be about 85 mm. In another embodiment, the skirt portion 24 has an oval shape and the dimension 28 defines a longer dimension of the skirt portion 24 of about 63 mm. An increased thickness, e.g., about 0.010 inches, may be used in connection with skirt portions having a larger diameter, such as about 65 mm. Other materials, such as nitinol or plastics having similar properties, may also be useful.

As discussed above, the skirt portion 24 preferably is coupled to the proximal wall portion 22 with a pivotal connection, such as rivet 30. A pair of rivet holes 36 can be provided in the skirt portion 24 to receive the rivet 30. The skirt portion 24 also has two free ends 38 and 40 in one embodiment that are secured by a slidable connection, such as a second rivet 44 (not shown in FIG. 5, illustrated in FIGS. 2-4). A pair of complementary slots 46 and 48 preferably are defined in the skirt portion 24 adjacent the free ends 38 and 40. The rivet 44 is permitted to move freely within the slots 46 and 48. This slot and rivet configuration allows the skirt portion 24 to move between the reduced profile configuration of FIG. 2 and the enlarged or expanded configurations of FIGS. 3-4. The use of a pair of slots 46 and 48 reduces the risk of the "button-holing" of the rivet 44, e.g., a situation in which the opening of the slot becomes distorted and enlarged such that the rivet may slide out of the slot, and cause failure of the device. The likelihood of such occurrence is reduced in skirt portion 24 because each of the slots 46 and 48 in the double slot configuration has a relatively shorter length than a single slot configuration. Being shorter, the slots 46, 48 are less likely to be distorted to the extent that a rivet may slide out of position. In addition, the configuration of rivet 44 and slots 46 and 48 permits a smoother operation of enlarging and reducing the skirt portion 24, and allows the skirt portion 24 to expand to span three or more vertebrae, e.g., L4, L5, and S1. This arrangement enables multi-level procedures, such as multilevel fixation procedures alone or in combination with a variety of other procedures, as discussed below. Other embodiments include a single slot rather than the slots 46, 48, or more than two slots.

An additional feature of the skirt portion 24 is the provision of a shallow concave profile 50 defined along the distal edge of the skirt portion 24, which allows for improved placement of the skirt portion 24 with respect to the body structures and the surgical instruments defined herein. In one embodiment, a pair of small scalloped or notched portions 56 and 58, are provided, as illustrated in FIG. 5. When the skirt portion 24 is assembled, the notched portions 56 and 58 are generally across from each other. When the skirt portion 24 is applied to a patient, the notched portions 56, 58 are oriented in the cephcaudal direction (indicated by a dashed line 60 in FIG. 4). In this arrangement, instruments and implants, such as an elongated member 650 used in a fixation procedure (described in detail below), may extend beyond the area enclosed by the skirt portion 24 without moving or raising the skirt portion 24, e.g., by allowing the elongated member 650 (or other implant or instrument) to pass under the skirt portion 24. The notched portions 56, 58 also enable the elongated member 650 (or other implant or instrument) to extend beyond the portion of the surgical space defined within the outline of the distal end of the skirt portion 24. The notched portions 56, 58 are optional, as illustrated in connection with another embodiment of an access device 54, illustrated in FIG. 6, and may be eliminated if, for example, the physician deems the notches to be unnecessary for the procedures to be performed. For example, in some fixation procedures such extended access is not needed, as discussed more fully below. As illustrated in FIG. 4, the skirt portion 24 may be expanded to a substantially conical configuration having a substantially circular or elliptical profile.

Furthermore, it is contemplated that the skirt portion 24 of the access device 20 can include a stop that retains the skirt portion in an expanded configuration, as shown in U.S. patent application Ser. No. 10/361,887, filed Feb. 10, 2003, now U.S. application patent Publication No. US2003/153927 A1, which is hereby incorporated by reference in its entirety herein.

With reference to FIGS. 7-12, another embodiment of an access device 100 comprises an elongate body 102 defining a passage 104 and having a proximal end 106 and a distal end 108. The elongate body 102 has a proximal portion 110 and a distal portion 112. The proximal portion 110 has an oblong or generally oval shaped cross section in one embodiment. The term "oblong" is used in its ordinary sense (i.e., having an elongated form) and is a broad term and it includes a structure having a dimension, especially one of two perpendicular dimensions, such as, for example, width or length, that is greater than another and includes shapes such as rectangles, ovals, ellipses, triangles, diamonds, trapezoids, parabolas, and other elongated shapes having straight or curved sides. The term "oval" is used in its ordinary sense (i.e., egg like or elliptical) and is a broad term and includes oblong shapes having curved portions.

The proximal portion 110 comprises an oblong, generally oval shaped cross section over the elongated portion. It will be apparent to those of skill in the art that the cross section can be of any suitable oblong shape. The proximal portion 110 can be any desired size. The proximal portion 110 can have a cross-sectional area that varies from one end of the proximal portion to another end. For example, the cross-sectional area of the proximal portion can increase or decrease along the length of the proximal portion 110. Preferably, the proximal portion 110 is sized to provide sufficient space for inserting multiple surgical instruments through the elongate body 102 to the surgical location. The distal portion 112 preferably is expandable and comprises first and second overlapping skirt members 114, 116. The degree of expansion of the distal portion 112 is determined by an amount of overlap between the first skirt member 114 and the second skirt member 116 in one embodiment.

The elongate body 102 of the access device 100 has a first location 118 distal of a second location 120. The elongate body 102 preferably is capable of having a configuration when inserted within the patient wherein the cross-sectional area of the passage 104 at the first location 118 is greater than the cross-sectional area of the passage 104 at the second location 120. The passage 104 preferably is capable of having an oblong shaped cross section between the second location 120 and the proximal end 106. In some embodiments the passage 104 preferably is capable of having a generally elliptical cross section between the second location 120 and the proximal end 106. Additionally, the passage 104 preferably is capable of having a non-circular cross section between the second location 120 and the proximal end 106. Additionally, in some embodiments, the cross section of the passage 104 can be symmetrical about a first axis and a second axis, the first axis being generally normal to the second axis.

In another embodiment, an access device comprises an elongate body defining a passage and having a proximal end and a distal end. The elongate body can be a unitary structure and can have a generally uniform cross section from the proximal end to the distal end. In one embodiment, the elongate body preferably has an oblong or generally oval shaped cross section along the entire length of the elongate body. The passage can have a generally elliptical cross section between the proximal end and the distal end. The elongate body preferably has a relatively fixed cross-sectional area along its entire length. In one embodiment, the elongate body is capable of having a configuration when inserted within the patient wherein the cross-sectional area of the passage at a first location is equal to the cross-sectional area of the passage at a second location. The passage preferably is capable of having an oblong shaped cross section between the first and second locations. The cross section of the passage can be of any suitable oblong shape and the elongate body can be any desired size. Preferably, the elongate body is sized to provide sufficient space for inserting multiple surgical instruments sequentially or simultaneously through the elongate body to the surgical location.

In one embodiment, the access device has a uniform, generally oblong shaped cross section and is sized or configured to approach, dock on, or provide access to, anatomical structures. The access device preferably is configured to approach the spine from a posterior position or from a postero-lateral position. A distal portion of the access device can be configured to dock on, or provide access to, posterior portions of the spine for performing spinal procedures, such as, for example, fixation, fusion, or any other procedure described herein. In one embodiment, the distal portion of the access device has a uniform, generally oblong shaped cross section and is configured to dock on, or provide access to, generally posterior spinal structures. Generally posterior spinal structures can include, for example, one or more of the transverse process, the superior articular process, the inferior articular process, and the spinous process. In some embodiments, the access device can have a contoured distal end to facilitate docking on one or more of the posterior spinal structures. Accordingly, in one embodiment, the access device has a uniform, generally oblong shaped cross section with a distal end sized, configured, or contoured to approach, dock on, or provide access to, spinal structures from a posterior or postero-lateral position.

Further details and features pertaining to access devices and systems are described in U.S. patent application Ser. No. 09/772,605, filed Jan. 30, 2001, application Ser. No. 09/906,463, filed Jul. 16, 2001, application Ser. No. 10/361,887, filed Feb. 10, 2003, application Ser. No. 10/280,489, filed Oct. 25, 2002, application Ser. No. 10/678,744 filed Oct. 2, 2003, Application No. 60/513,796, filed Oct. 22, 2003, Application No. 60/514,559, filed Oct. 24, 2003, and Application No. 60/558,296, filed Mar. 31, 2004 which are incorporated by reference in their entireties herein.

2. Dilators and Expander Devices

According to one application or procedure, an early stage involves determining a point in the skin of the patient at which to insert the access device 20. The access point preferably corresponds to a posterior-lateral aspect of the spine. Manual palpation and Anterior-Posterior (AP) fluoroscopy may be used to determine preferred or optimal locations for forming an incision in the skin of the patient. In one application, the access device 20 preferably is placed midway (in the cephcaudal direction) between the L4 through S1 vertebrae, centrally about 4-7 cm from the midline of the spine.

After the above-described location is determined, an incision is made at the location. A guide wire (not shown) is introduced under fluoroscopic guidance through the skin, fascia, and muscle to the approximate surgical site. A series of dilators is used to sequentially expand the incision to the desired width, about 23 mm in one procedure, preferably minimizing damage to the structure of surrounding tissue and muscles. A first dilator can be placed over the guide wire to expand the opening. The guide wire may then be removed. A second dilator, slightly larger than the first dilator, is placed over the first dilator to expand the opening further. Once the second dilator is in place, the first dilator may be removed. This process of (1) introducing a next-larger-sized dilator coaxially over the previous dilator and (2) optionally removing the previous dilator(s) when the next-larger-sized dilator is in place continues until an opening of the desired size is created in the skin, muscle, and subcutaneous tissue. According to one application, the desired opening size is about 23 mm. (Other dimensions of the opening, e.g., about 20 mm, about 27 mm, about 30 mm, etc., are also usefuil with this apparatus in connection with spinal surgery, and still other dimensions are contemplated.)

FIG. 13 shows that following placement of a dilator 120, which is the largest dilator in the above-described dilation process, the access device 20 is introduced in its reduced profile configuration and positioned over the dilator 120. The dilator 120 is subsequently removed from the patient, and the access device 20 remains in position.

Once positioned in the patient, the access device 20 may be enlarged to provide a passage for the insertion of various surgical instruments and to provide an enlarged space for performing the procedures described herein. As described above, the access device may achieve the enlargement in several ways. In one embodiment, a distal portion of the access device may be enlarged, and a proximal portion may maintain a constant diameter. The relative lengths of the proximal portion 22 and the skirt portion 24 may be adjusted to vary the overall expansion of the access device 20. Alternatively, such expansion may extend along the entire length of the access device 20. In one application, the access device 20 may be expanded by removing a suture 35 and tearing the outer sleeve 32 surrounding the access device 20, and subsequently allowing the skirt portion 24 to resiliently expand towards its fully expanded configuration as (illustrated in FIG. 4) to create an enlarged surgical space from the L4 to the S1 vertebrae. The resisting force exerted on the skirt portion 24 may result in the skirt portion 24 assuming the intermediate configuration illustrated in FIG. 3. Under many circumstances, the space created by the skirt portion 24 in the intermediate configuration is a sufficiently large working space to perform the procedure described herein. Once the skirt portion 24 has expanded, the rigidity and resilient characteristics of the skirt portion 24 preferably allow the access device 20 to resist closing to the reduced profile configuration of FIG. 2 and to at least temporarily resist being expelled from the incision. These characteristics create a stable configuration for the access device 20 to remain in position in the body, supported by the surrounding tissue. It is understood that additional support may be needed, especially if an endoscope is added.

According to one embodiment of a procedure, the access device 20 may be further enlarged at the skirt portion 24 using an expander apparatus to create a surgical access space. An expander apparatus useful for enlarging the access device has a reduced profile configuration and an enlarged configuration. The expander apparatus is inserted into the access device in the reduced profile configuration, and subsequently expanded to the enlarged configuration. The expansion of the expander apparatus also causes the access device to be expanded to the enlarged configuration. In some embodiments, the expander apparatus may increase the diameter of the access device along substantially its entire length in a generally conical configuration. In other embodiments, the expander apparatus expands only a distal portion of the access device, allowing a proximal portion to maintain a relatively constant diameter.

In addition to expanding the access device, in some embodiments the expander apparatus may also be used to position the distal portion of the access device at the desired location for the surgical procedure. The expander can engage an interior wall of the access device to move the access device to the desired location. For embodiments in which the distal portion of the access device is relatively movable with respect to the proximal portion, the expander apparatus is useful to position the distal portion without substantially disturbing the proximal portion.

Figure 15:
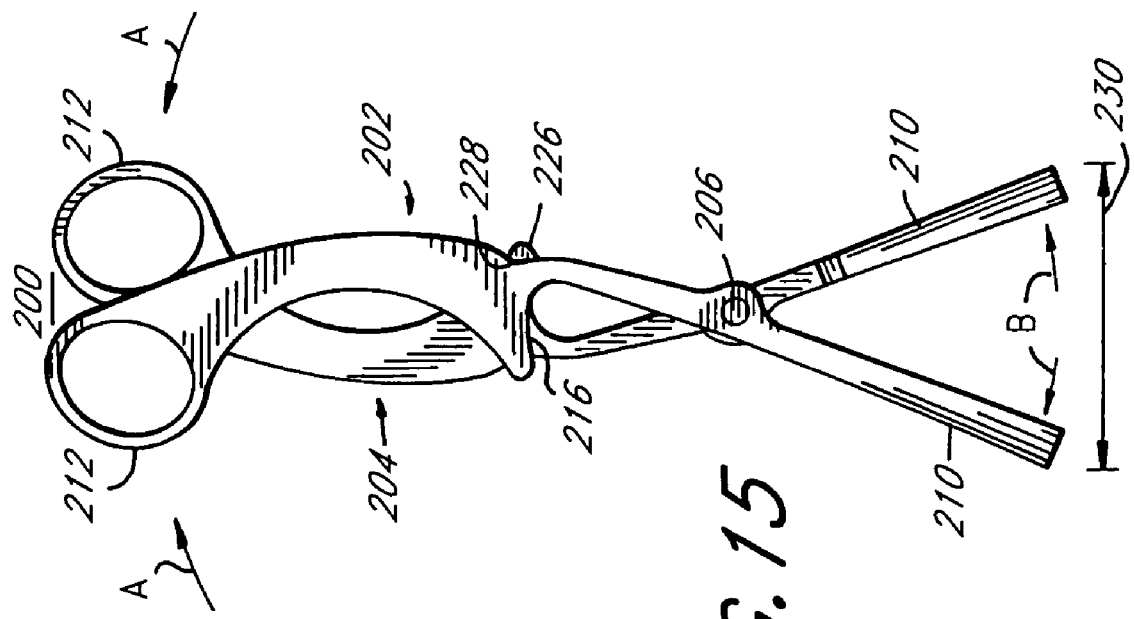
FIG. 15 is a side view of the expander apparatus of FIG. 14 in an expanded configuration.
Figure 14:
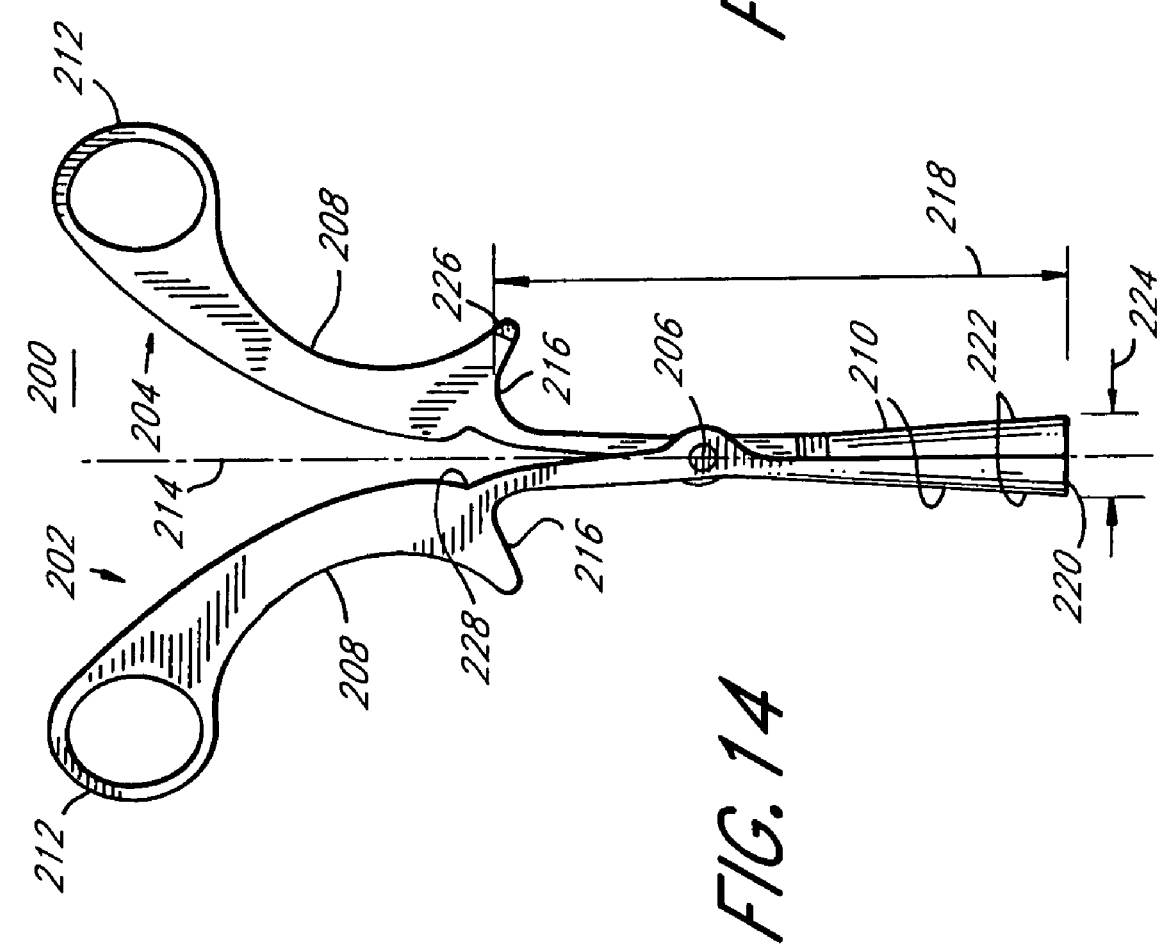
FIG. 14 is a side view of one embodiment of an expander apparatus in a reduced profile configuration.
Figure 18:
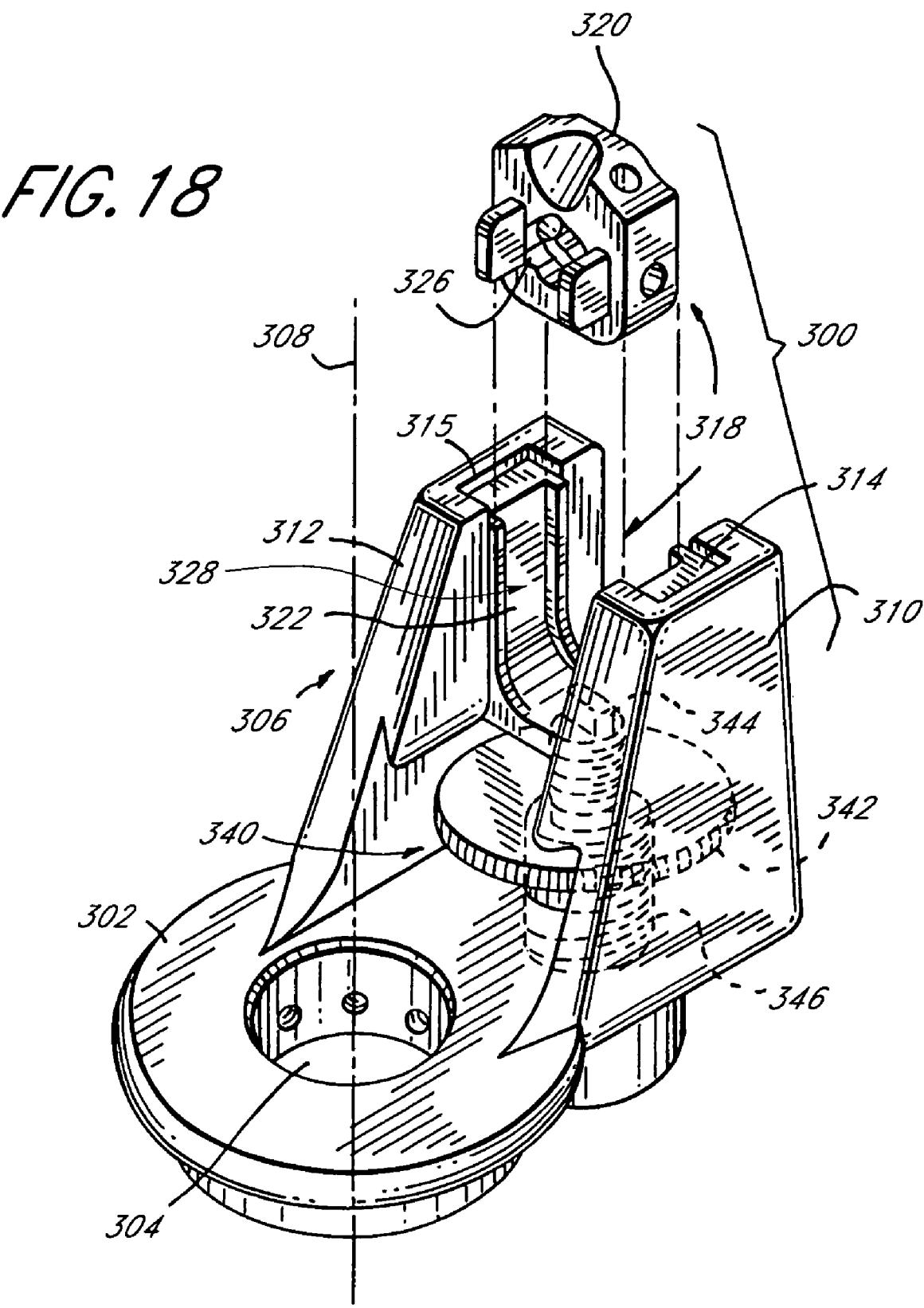
FIG. 18 is an exploded perspective view of one embodiment of an endoscope mount platform.

In some procedures, an expander apparatus is used to further expand the skirt portion 24 towards the enlarged configuration (illustrated in FIG. 4). The expander apparatus is inserted into the access device, and typically has two or more members that are movable to engage the interior wall of the skirt portion 24 and apply a force sufficient to further expand the skirt portion 24. FIGS. 14 and 15 show one embodiment of an expander apparatus 200 that has a first component 202 and a second component 204. The first component 202 and the second component 204 of the expander apparatus 200 are arranged in a tongs-like configuration and are pivotable about a pin 206. The first and second components 202 and 204 can be constructed of steel having a thickness of about 9.7 mm. Each of the first and second components 202 and 204 has a proximal handle portion 208 and a distal expander portion 210. Each proximal handle portion 208 has a finger grip 212 that may extend transversely from an axis, e.g., a longitudinal axis 214, of the apparatus 200. The proximal handle portion 208 may further include a stop element, such as flange 216, that extends transversely from the longitudinal axis 214. The flange 216 preferably is dimensioned to engage the proximal end 25 of the access device 20 when the apparatus 200 is inserted a predetermined depth. This arrangement provides a visual and tactile indication of the proper depth for inserting the expander apparatus 200. In one embodiment, a dimension 218 from the flange 216 to the distal tip 220 is about 106 mm. The dimension 218 is determined by the length of the access device 20, which in turn is a function of the depth of the body structures beneath the skin surface at which the surgical procedure is to be performed. The distal portions 210 are each provided with an outer surface 222 for engaging the inside wall of the skirt portion 24. The outer surface 222 is a frusto-conical surface in one embodiment. The expander apparatus 200 has an unexpanded distal width 224 at the distal tip 220 that is about 18.5 mm in one embodiment.

In use, the finger grips 212 are approximated towards one another, as indicated by arrows A in FIG. 15, which causes the distal portions 210 to move to the enlarged configuration, as indicated by arrows B. The components 202 and 204 are also provided with a cooperating tab 226 and shoulder portion 228 which are configured for mutual engagement when the distal portions 210 are in the expanded configuration. In the illustrated embodiment, the expander apparatus 200 has an expanded distal width 230 that extends between the distal portions 210. The expanded distal width 230 can be about 65 mm or less, about as large as 83 mm or less, or any other suitable width. The tab 226 and shoulder portion 228 together limit the expansion of the expander apparatus 200 to prevent expansion of the skirt portion 24 of the access device 20 beyond its designed dimension, and to minimize trauma to the underlying tissue. Further features related to the expander apparatus are described in U.S. Pat. No. 6,652,553, issued Nov. 25, 2003, which is incorporated by reference in its entirety herein.

When the access device 20 is inserted into the patient and the outer sleeve 32 is removed, the skirt portion 24 expands to a point where the outward resilient expansion of the skirt portion 24 is balanced by the force of the surrounding tissue. The surgical space defined by the access device 20 may be sufficient to perform any of a number of surgical procedures or combination of surgical procedures described herein. However, if it is desired to expand the access device 20 further, the expander apparatus 200, or a similar device, may be inserted into the access device 20 in the reduced profile configuration until the shoulder portions 216 are in approximation with the proximal end 25 of the skirt portion 24 of the access device 20, as shown in FIG. 16.

FIG. 16 shows the expander apparatus 200 inserted in the access device 20 in the reduced profiled configuration. Expansion of the expander apparatus 200 is achieved by approximating the handle portions 212 (not shown in FIG. 16), which causes the distal portions 210 of the expander apparatus 200 to move to a spaced apart configuration. As the distal portions 210 move apart and contact the inner wall of the skirt portion 24, the rivet 44 is allowed to slide within the slots 46 and 48 of the skirt portion 24, thus permitting the skirt portion 24 to expand. When the distal portions 210 reach the maximum expansion of the skirt portion 24 (illustrated by a dashed line in FIG. 17), the tab 226 and shoulder portion 228 of the expander apparatus 200 come into engagement to prevent further expansion of the tongs-like portions (as illustrated in FIG. 15). Alternatively, the access device 20 may be expanded with another device that can selectively have a reduced profile configuration and an expanded configuration, e.g., a balloon or similar device.

An optional step in the procedure is to adjust the location of the distal portion of the access device 20 relative to the body structures to be operated on. For example, the expander apparatus 200 may also be used to engage the inner wall of the skirt portion 24 of the access device 20 in order to move the skirt portion 24 of the access device 20 to the desired location. For an embodiment in which the skirt portion 24 of the access device 20 is relatively movable relative to the proximal portion, e.g. by use of the rivet 30, the expander apparatus 200 is useful to position the skirt portion 24 without substantially disturbing the proximal portion 22 or the tissues closer to the skin surface of the patient. As will be described below, the ability to move the distal end portion, e.g., the skirt portion 24, without disturbing the proximal portion is especially beneficial when an additional apparatus is mounted relative to the proximal portion of the access device, as described below.

B. Systems and Devices for Stabilization and Visualization

Some procedures can be conducted through the access device 20 without any additional peripheral components being connected thereto. In other procedures it may be beneficial to provide at least one of a support device and a viewing element. As discussed more fully below, support devices can be advantageously employed to provide support to peripheral equipment and to surgical tools of various types. Various embodiments of support devices and viewing elements are discussed herein below.

1. Support Devices

One type of support device that can be coupled with the access device 20 is a device that supports a viewing element. In one embodiment, an endoscope mount platform 300 and indexing arm 400 support an endoscope 500 on the proximal end 25 of the access device 20 for remotely viewing the surgical procedure, as illustrated in FIGS. 18-21. The endoscope mount platform 300 may also provide several other functions during the surgical procedure. The endoscope mount platform 300 preferably includes a base 302 that extends laterally from a central opening 304 in a generally ring-shaped configuration. In one application, the physician views the procedure primarily by observing a monitor, when inserting surgical instruments into the central opening 304. The base 302 advantageously enables the physician by providing a visual indicator (in that it may be observable in the physician's peripheral vision) as well as tactile feedback as instruments are lowered towards the central opening 304 and into the access device 20.

The endoscope mount platform 300 preferably has a guide portion 306 at a location off-set from the central opening 304 that extends substantially parallel to a longitudinal axis 308. The base 302 can be molded as one piece with the guide portion 306. The base 302 and guide portion 306 may be constructed with a suitable polymer, such as, for example, polyetheretherketone (PEEK).

The guide portion 306 includes a first upright member 310 that extends upward from the base 302 and a second upright member 312 that extends upward from the base 302. In one embodiment, the upright members 310, 312 each have a respective vertical grooves 314 and 315 that can slidably receive an endoscopic mount assembly 318.

Figure 25:
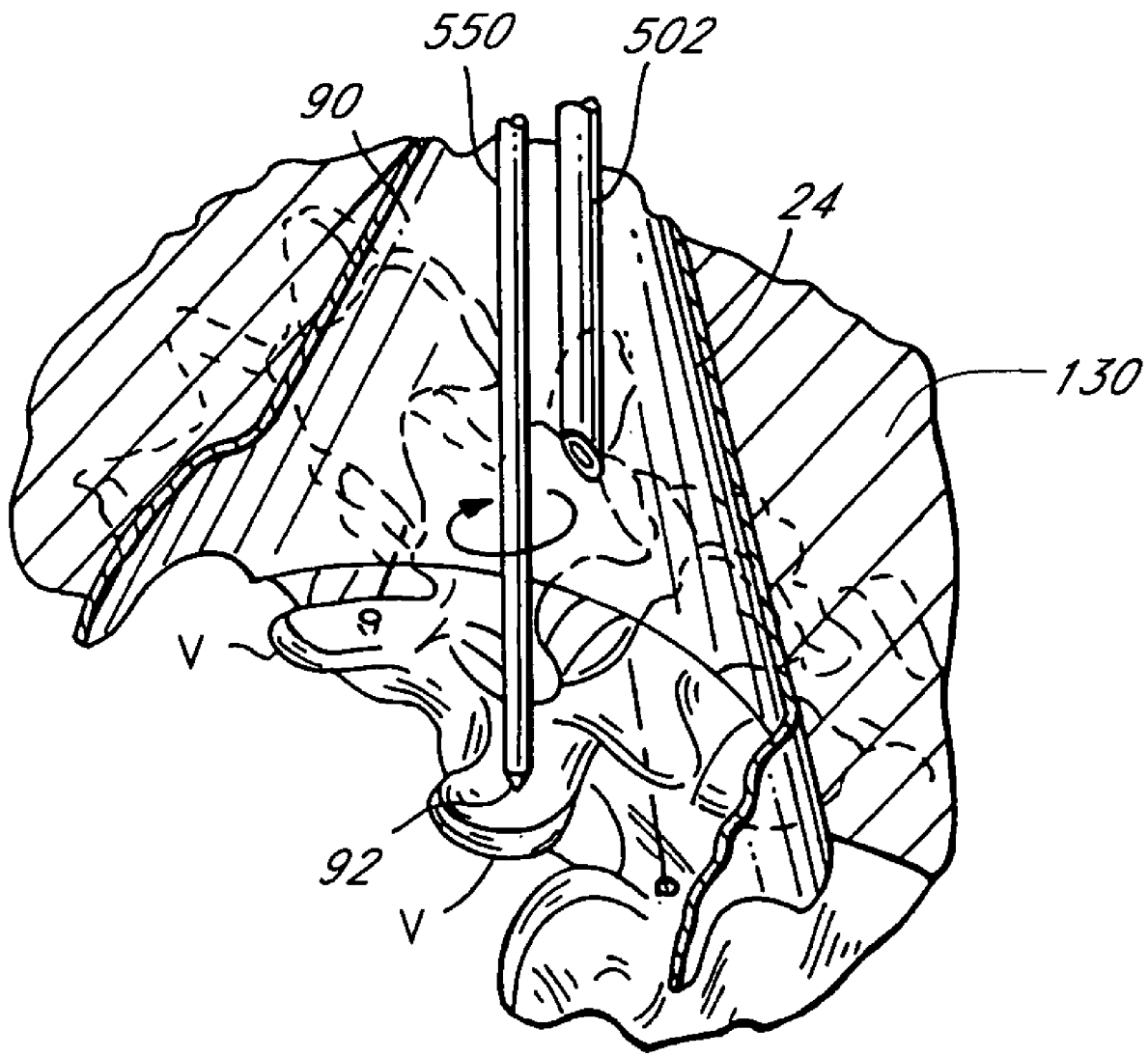
FIG. 25 is a partial sectional view of one stage of one application of a method for treating the spine of a patient.

The endoscope 500 (not shown in FIG. 18) can be movably mounted to the endoscope mount platform 300 with the endoscope mount assembly 318 in one embodiment. The endoscope mount assembly 318 includes an endoscope mount 320 and a saddle unit 322. The saddle unit 322 is slidably mounted within the grooves 314 and 315 in the upright members 310 and 312. The endoscope mount 320 receives the endoscope 500 through a bore 326 which passes through the endoscope mount 320. Part of the endoscope 500 may extend through the access device 20 substantially parallel to longitudinal axis 308 into the patient's body 130, as shown in FIG. 25.

The endoscope mount 320 is removably positioned in a recess 328 defined in the substantially "U"-shaped saddle unit 322. In one embodiment, the saddle unit 322 is selectively movable in a direction parallel to the longitudinal axis 308 in order to position the endoscope 500 at the desired height within the access device 20. The movement of the endoscope 500 by way of the saddle unit 322 also advantageously enables the physician to increase visualization of a particular portion of the surgical space defined by the access device, e.g., by way of a zoom feature, as required for a given procedure or a step of a procedure.

In one embodiment, an elevation adjustment mechanism 340, which may be a screw mechanism, is positioned on the base 302 between the upright members 310 and 312. The elevation adjustment mechanism 340 can be used to selectively move a viewing element, e.g., the endoscope 500 by way of the saddle unit 322. In one embodiment, the elevation adjustment mechanism 340 comprises a thumb wheel 342 and a spindle 344. The thumb wheel 343 is rotatably mounted in a bore in the base 302. The thumb wheel 342 has an external thread 346 received in a cooperating thread in the base 302. The spindle 344 is mounted for movement substantially parallel to the central axis 308. The spindle 344 preferably has a first end received in a rectangular opening in the saddle unit 322, which inhibits rotational movement of the spindle 344. The second end of the spindle 344 has an external thread that cooperates with an internal thread formed in a bore within the thumb wheel 342. Rotation of the thumb wheel 342 relative to the spindle 344, causes relative axial movement of the spindle unit 344 along with the saddle unit 322. Further details and features related to endoscope mount platforms are described in U.S. Pat. No. 6,361,488, issued Mar. 26, 2002; U.S. Pat. No. 6,530,880, issued Mar. 11, 2003, and U.S. patent application Ser. No. 09/940,402, filed Aug. 27, 2001, published as Publication No. 2003/0040656 on Feb. 27, 2003, which are incorporated by reference in their entireties herein.

Figure 19:
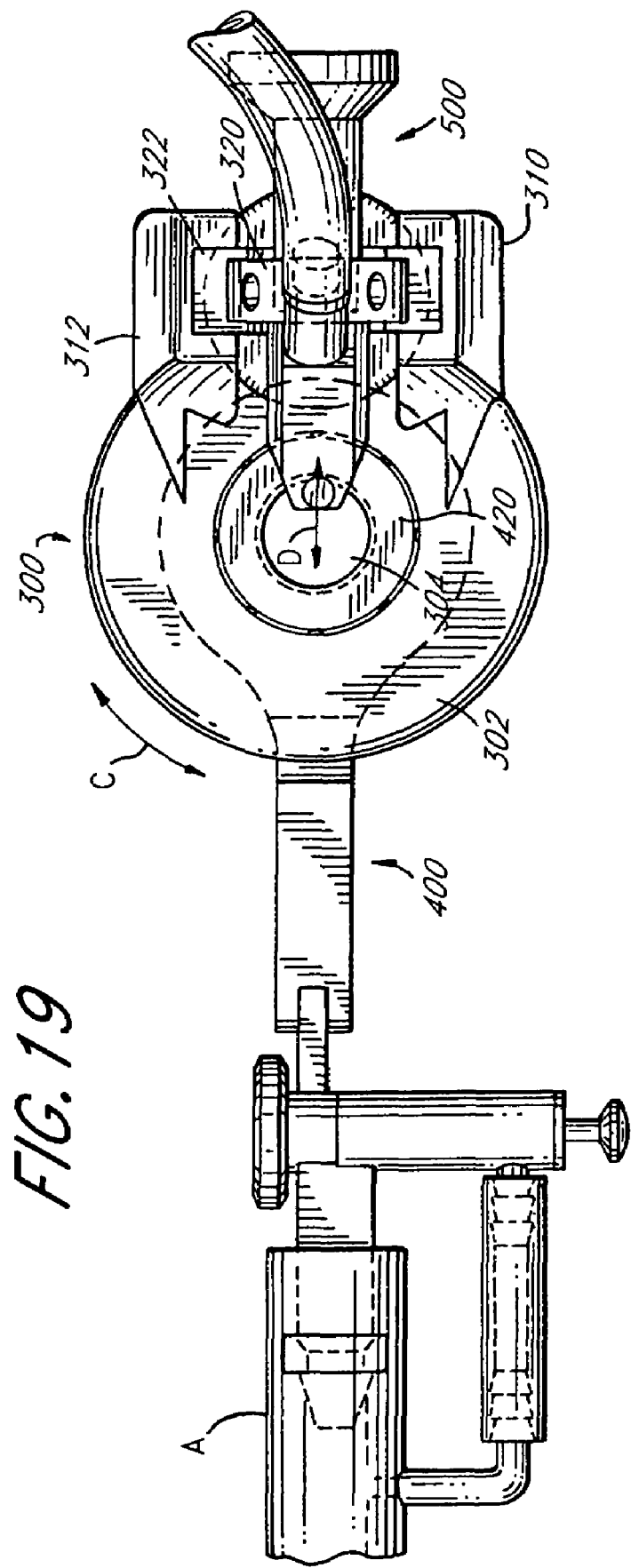
FIG. 19 is a top view of the endoscope mount platform of FIG. 18 coupled with one embodiment of an indexing arm and one embodiment of an endoscope.

FIGS. 19-21 show that the endoscope mount platform 300 is mountable to the support arm 400 in one embodiment. The support arm 400, in turn, preferably is mountable to a mechanical support, such as mechanical support arm A, discussed above in connection with FIG. 1. The support arm 400 preferably rests on, or is otherwise coupled to, the proximal end 25 of the access device 20. In one embodiment, the support arm 400 is coupled with an indexing collar 420, which is configured to be received in the central opening 304 of the base 302 of endoscope mount platform 300. The indexing collar 420 is substantially toroidal in section and has an outer peripheral wall surface 422, an inner wall surface 424, and a wall thickness 426 that is the distance between the wall surfaces 422, 424. The indexing collar 420 further includes a flange 428, which supports the indexing collar 420 on the support arm 400.

In one embodiment, a plurality of collars 420 may be provided to make the surgical system 10 modular in that different access devices 20 may be used with a single endoscope mount platform 300. For example, access devices 20 of different dimensions may be supported by providing indexing collars 420 to accommodate each access device size while using a single endoscope mount platform 300. The central opening 304 of the endoscope mount platform 300 can have a constant dimension, e.g., a diameter of about 32.6 mm. An appropriate indexing collar 420 is selected, e.g., one that is appropriately sized to support a selected access device 20. Thus, the outer wall 422 and the outer diameter 430 are unchanged between different indexing collars 420, although the inner wall 424 and the inner diameter 432 vary to accommodate differently sized access devices 20.

The indexing collar 420 can be mounted to the proximal portion of the access device 20 to allow angular movement of the endoscope mount platform 300 with respect thereto about the longitudinal axis 308 (as indicated by an arrow C in FIG. 19). The outer wall 422 of the index collar 420 includes a plurality of hemispherical recesses 450 that can receive one or more ball plungers 350 on the endoscope mount platform 300 (indicated in dashed line). This arrangement permits the endoscope mount platform 300, along with the endoscope 500, to be fixed in a plurality of discrete angular positions.

Further details and features related to support arms and indexing collars are described in U.S. Pat. No. 6,361,488, issued Mar. 26, 2002, U.S. Pat. No. 6,530,880 issued Mar. 11, 2003, and application Ser. No. 09/940,402 filed Aug. 27, 2001, published as Publication No. 2003/0040656 on Feb. 27, 2003, which are incorporated by reference in their entireties herein.

2. Viewing Elements

As discussed above, a variety of viewing elements and visualization techniques are embodied in variations of the surgical system 10. One viewing element that is provided in one embodiment is an endoscope.

Figure 22:
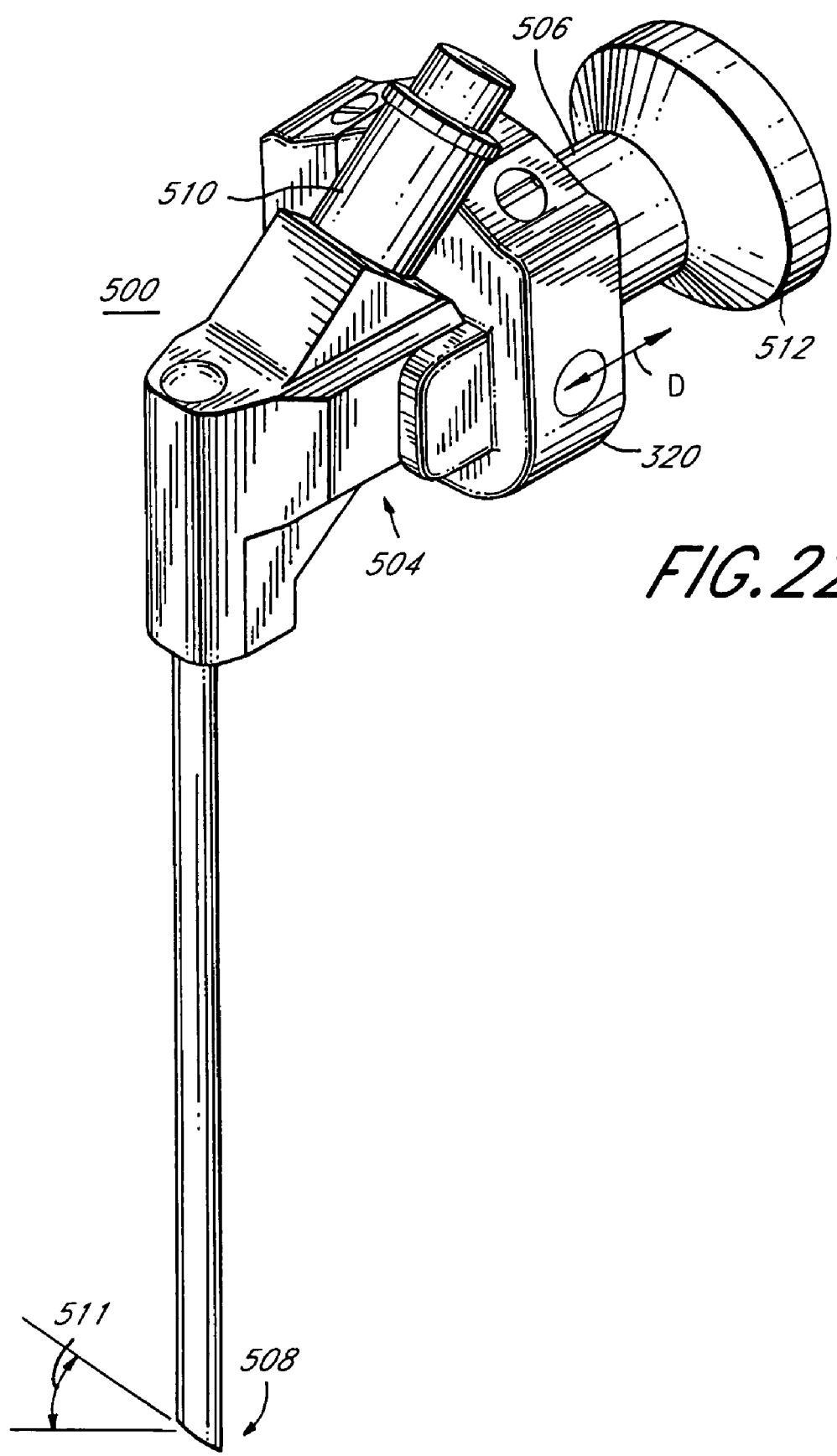
FIG. 22 is a perspective view of one embodiment of an endoscope.

FIG. 22 shows one embodiment of the endoscope 500 that has an elongated configuration that extends into the access device 20 in order to enable viewing of the surgical site. In particular, the endoscope 500 has an elongated rod portion 502 and a body portion 504. The rod portion 502 extends generally perpendicularly from the body portion 504. In one embodiment, the rod portion 502 of endoscope 500 has a diameter of about 4 mm and a length of about 106 mm. Body portion 504 may define a tubular portion 506 configured to be slidably received in the bore 326 of endoscope mount 320 as indicated by an arrow D. The slidable mounting of the endoscope 500 on the endoscope mount platform 300 permits the endoscope 500 to adjust to access device configurations that have different diameters. Additional mobility of the endoscope 500 in viewing the surgical site may be provided by rotating the endoscope mount platform 300 about the central axis 308 (as indicated by arrow C in FIG. 19).

The rod portion 502 supports an optical portion (not shown) at a distal end 508 thereof. In one embodiment, the rod portion 502 defines a field of view of about 105 degrees and a direction of view 511 of about 25-30 degrees. An eyepiece 512 preferably is positioned at an end portion of the body portion 504. A suitable camera (not shown) preferably is attached to the endoscope 500 adjacent the eyepiece 512 with a standard coupler unit. A light post 510 can supply illumination to the surgical site at the distal end portion 508. A preferred camera for use in the system and procedures described herein is a three chip unit that provides greater resolution to the viewed image than a single chip device.

Figure 23A:
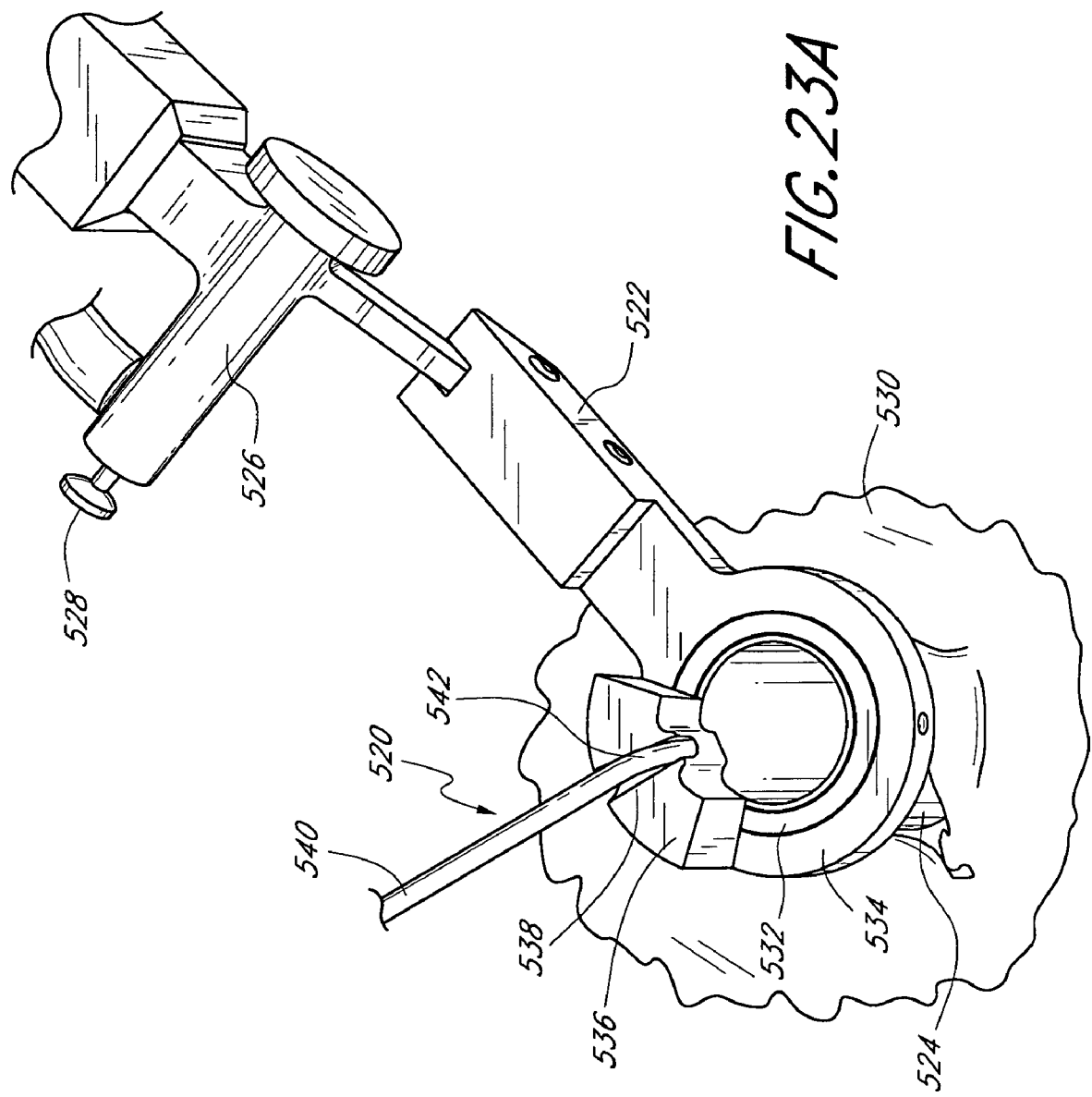
FIG. 23A is a top perspective view of one embodiment of an access system.
Figure 23C:
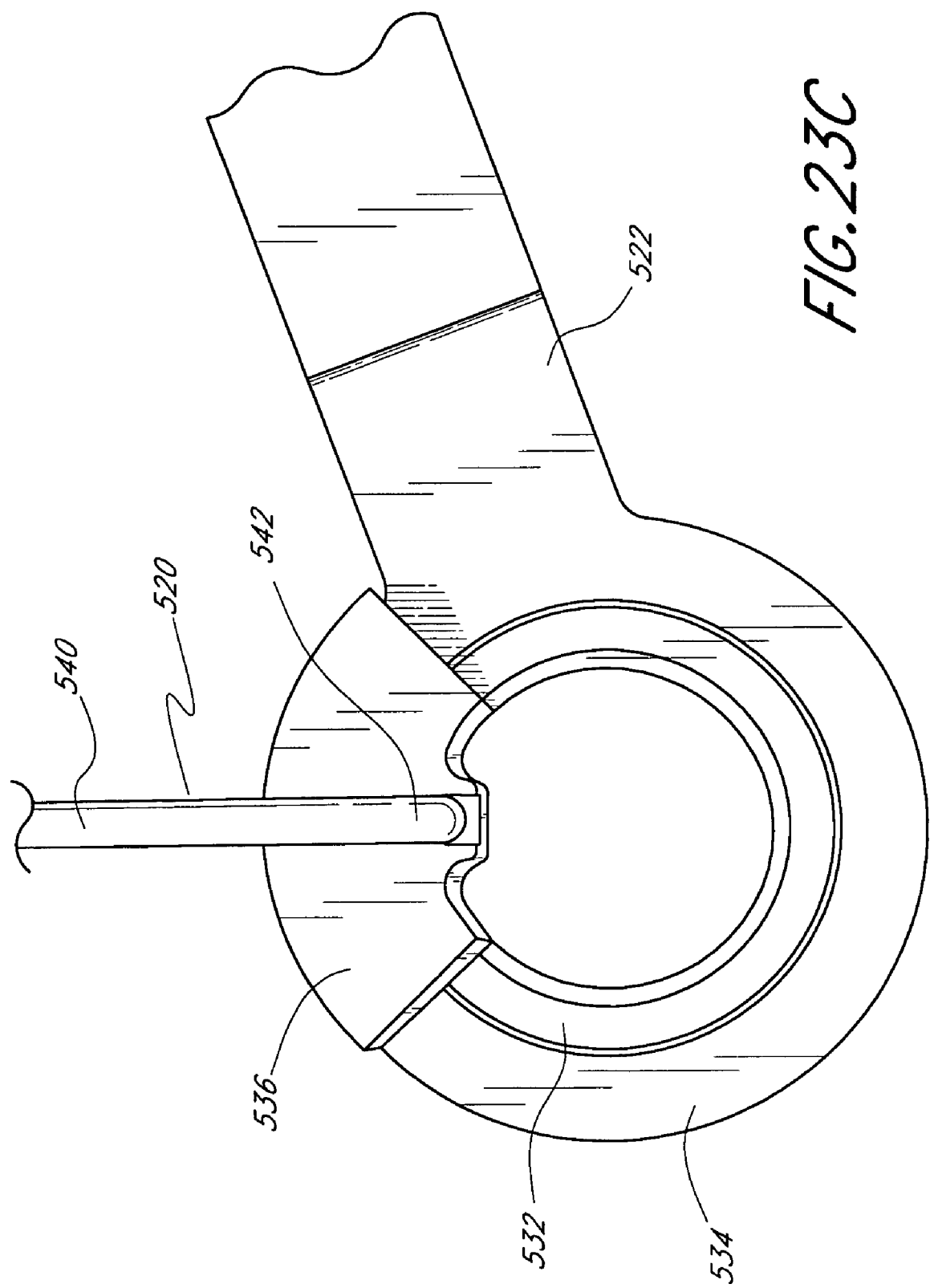
FIG. 23C is a top view of the access system of FIG. 23A.

FIGS. 23A, 23B, 23C, 24A, 24B, and 24C illustrate other embodiments of support devices and viewing elements. FIGS. 23A, 23B, and 23C illustrate one embodiment of a lighting element 520 coupled with a support arm 522 compatible with an access device 524 having a proximal portion with a generally circular cross section. In other embodiments, support arms can be configured to be coupled with access devices having proximal portions with generally oblong or oval cross sections.

The support arm 522 preferably is coupled with the access device 524 to provide support for the access device 524 during a procedure. As shown in FIGS. 23A, 23B, and 23C, the support arm 522 comprises a pneumatic element 526 for maintaining the support arm 522 in a desired position. Depressing a button 528 coupled with a valve of the pneumatic element 526 releases pressure and allows the support arm 522 and access device 524 to be moved relative the patient 530. Releasing the button 528 of the pneumatic element 526 increases pressure and maintains the access device 524 and support arm 522 in the desired position. The support arm 522, as shown, is configured for use with a mechanical arm using a suction, or a vacuum to maintain the access device in a desired location. One of skill in the art will recognize that various other support arms and mechanical arms can be used. For example, commercially available mechanical arms having clamping mechanisms can be used as well as suction or pressure based arms.

The support arm 522 can comprise an inner ring portion 532 and an outer ring portion 534 for surrounding the access device 524 at its proximal end. In the illustrated embodiment, the inner and outer ring portions 532, 534 are fixed relative each other. In other embodiments the inner and outer ring portions 532, 534 can move relative each other. The support arm 522 preferably comprises a lighting element support portion 536. In the illustrated embodiment, the lighting element support portion 536 extends above upper surfaces of the inner and outer ring portions 532, 534. The lighting element support portion 536 can extend from the inner ring portion 532, the outer ring portion 534, or both. The lighting element support portion 536 can have a notch or groove 538 for receiving and supporting the lighting element 520. Additionally, the lighting element support portion 536 can have one or more prongs extending at least partially over the lighting element 520 to hold it in place.

In the illustrated embodiment, the lighting element 520 has an elongated proximal portion 540 and a curved distal portion 542. The proximal portion 540 of the lighting element 520 preferably is coupled with a light source (not shown). The curved distal portion of the lighting element 520 in one embodiment extends only a short distance into the access device and is configured to direct light from the light source down into the access device 524. In another embodiment, the lighting element 520 can be provided such that it does not extend into the access device. In such an embodiment, the right portions 532 and 534 only partially surround the proximal end of the access device 524. Providing a lighting element 520 for use with the access device 524 preferably allows a user to see down into the access device 524 to view a surgical location. Accordingly, use of a lighting element 520 in some cases, enables the user to perform a procedure, in whole or in part, without the use of an endoscope. In one embodiment, the lighting element 520 enables a surgeon to perform the procedure with the use of microscopes or loupes.

Figure 24A:
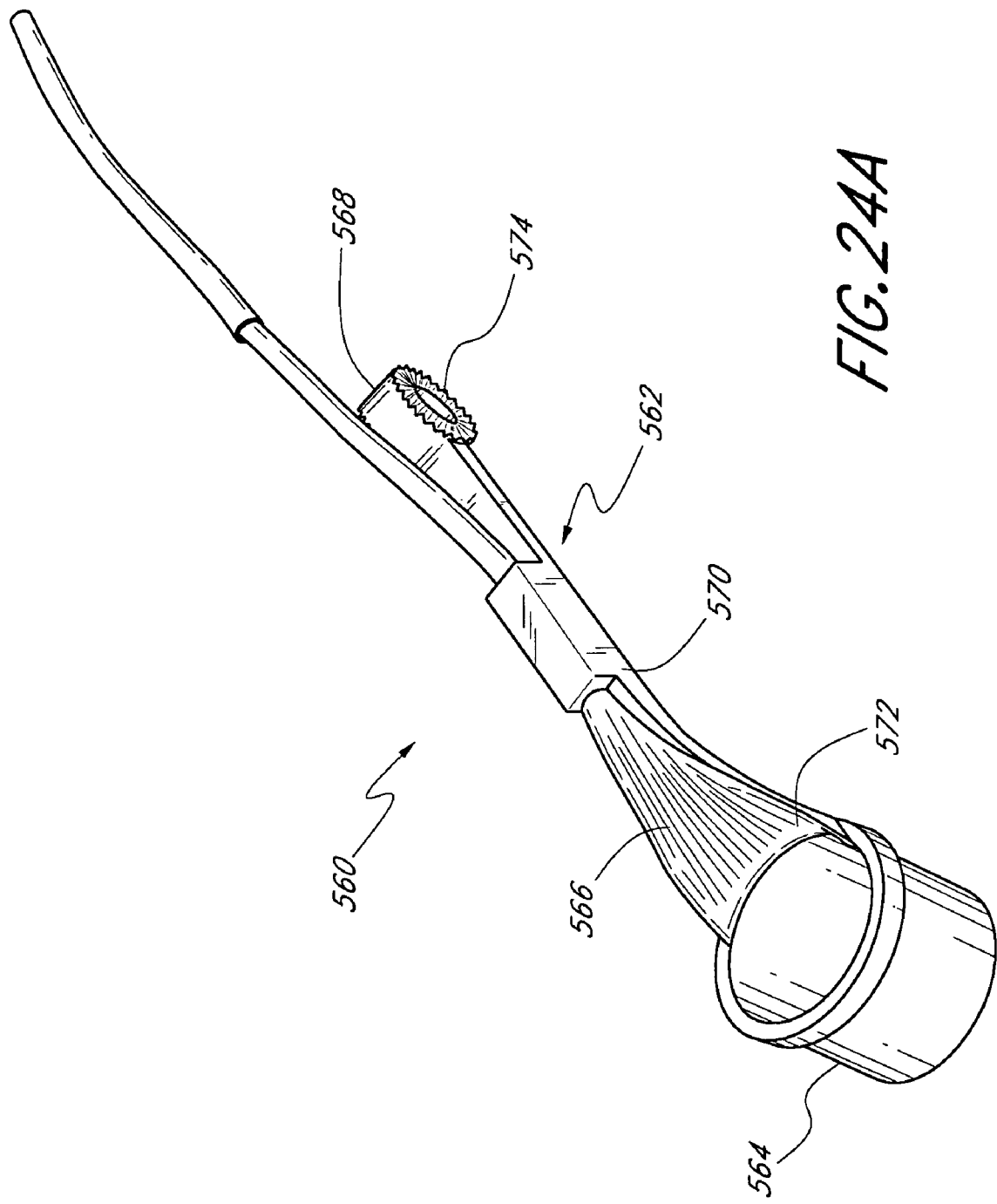
FIG. 24A is a perspective view of one embodiment of a lighting element.

FIGS. 24A, 24B, and 24C illustrate other embodiments of visualization elements. As shown in FIG. 24A, a lighting element 560 comprises a support member 562, an access device insert 564, and fiber optic elements 566. The support member 562 has a proximal end 568, a central portion 570, and a distal end 572. The proximal end 568 preferably has a coupling portion 574 for coupling the support member 562 to a support arm or other support system (not shown). The central portion 570 preferably is coupled with the fiber optic elements 566 to provide support there to. The distal end 572 preferably is coupled with the access device insert 564.

In the illustrated embodiment, the access device insert 564 is configured to be inserted in an access device having a proximal portion with a generally circular cross section. The access device insert 564 is coupled with the fiber optic elements 566. The fiber optic elements 566 extend down into the access device insert 564 so that the ends of the fiber optic elements 566 can direct light down inside an access device along side portions there of.

FIGS. 24B and 24C illustrate other embodiments of visualization elements similar to the embodiment described with reference to FIG. 24A. In the illustrated embodiments, the access device inserts 564 are configured to be inserted into access devices having proximal portions with generally oblong, or oval, cross sections. As shown in FIG. 24B, the access device insert 564 has a generally oblong or oval shaped cross section. The access device insert 564 is coupled with the fiber optic elements 566 along a longer side surface of the access device insert 564. As shown in FIG. 24C, the access device insert 564 has a generally oblong or oval shaped cross section. The access device insert 564 is coupled with the fiber optic elements 566 along a shorter side surface of the access device insert 564. Use of an illumination element with an expandable access device having an oblong shaped proximal section, in some cases, allows a doctor to perform procedures that would be difficult to perform using an endoscope. Increased visualization of the surgical location through the access device can simplify some procedures. For example, decompression of the contra-lateral side can be achieved more easily in some cases without the use of an endoscope.

C. Apparatuses and Methods for Performing Spinal Procedures

The surgical assembly 10 described above can be deployed to perform a wide variety of surgical procedures on the spine. In many cases, the procedures are facilitated by inserting the access device and configuring it to provide greater access to a surgical location, as discussed above and by mounting the support arm 400 and the endoscope mount platform 300 on the proximal portion, e.g., on the proximal end 25, of the access device 20 (FIGS. 1 and 22). As discussed above, visualization of the-surgical location is enhanced by mounting a viewing element, such as the endoscope 500, on the endoscope mount platform 300. Having established increased access to and visualization of the surgical location, a number of procedures may be effectively performed.

Generally, the procedures involve inserting one or more surgical instruments into the access device 20 to manipulate or act on the body structures that are located at least partially within the operative space defined by the expanded portion of the access device 20. FIG. 25 shows that in one method, the skirt portion 24 of access device 20 at least partially defines a surgical site or operative space 90 in which the surgical procedures described herein may be performed. Depending upon the overlap of the skirt portion, the skirt portion may define a surface which is continuous about the perimeter or which is discontinuous, having one or more gaps where the material of the skirt portion does not overlap.

One procedure performable through the access device 20, described in greater detail below, is a two-level spinal fusion and fixation. Surgical instruments inserted into the access device may be used for debridement and decortication. In particular, the soft tissue, such as fat and muscle, covering the vertebrae may be removed in order to allow the physician to visually identify the various "landmarks," or vertebral structures, which enable the physician to determine the location for attaching a fastener, such a fastener 600, discussed below, or other procedures, as will be described herein. Enabling visual identification of the vertebral structures enables the physician to perform the procedure while viewing the surgical area through the endoscope, microscope, loupes, or other viewing element, or in a conventional, open manner.

Tissue debridement and decortication of bone are completed using one or more of a debrider blades, a bipolar sheath, a high speed burr, and any other conventional manual instrument. The debrider blades are used to excise, remove and aspirate the soft tissue. The bipolar sheath is used to achieve hemostasis through spot and bulk tissue coagulation. Additional features of debrider blades and bipolar sheaths are described in U.S. Pat. No. 6,193,715, assigned to Medical Scientific, Inc., which is incorporated by reference in its entirety herein. The high speed burr and conventional manual instruments are also used to continue to expose the structure of the vertebrae.

1. Fixation Systems and Devices

Having increased visualization of the pertinent anatomical structure, various procedures may be carried out on the structures. In one procedure, one or more fasteners are attached to adjacent vertebrae V. As discussed in more detail below, the fasteners can be used to provide temporary or permanent fixation and to provide dynamic stabilization of the vertebrae V. These procedures may combined with other procedures, such as procedures employing other types of implant, e.g., procedures employing fusion devices, prosthetic disc components, or other suitable implants. In some procedures, fasteners are attached to the vertebrae before or after fusion devices are inserted between the vertebrae V. Fusion systems and devices are discussed further below.

In one application, the desired location and orientation of the fastener is determined before the fastener is applied to the vertebra. The desired location and orientation of the fastener may be determined in any suitable manner. For example, the pedicle entry point of the L5 vertebrae may be located by identifying visual landmarks alone or in combination with lateral and A/P fluoroscopy, as is known in the art. With continued reference to FIG. 25, an entry point 92 into the vertebra V is prepared. In procedure, the entry point 92 may be prepared with an awl 550. The entry point 92 corresponds to the pedicle in one procedure. The entry point 92 may be prepared in any suitable manner, e.g., employing a bone probe, a tap, and a sounder to create and verify the integrity of the prepared vertebra. The sounder, as is known in the art, determines whether the hole that is made is surrounded by bone on all sides, and can be used to confirm that there has been no perforation of the pedicle wall.

After the hole in the pedicle beneath the entry point 92 is prepared, a fastener may be advanced into the hole. Prior to advancing the fastener, or at any other point during the procedure, it may be desirable to adjust the location of the distal portion of the access device 20. The distal portion of the access device 20 may be adjusted by inserting the expander apparatus 200 into the access device 20, expanding the distal portions 210, and contacting the inner wall of the skirt portion 24 to move the skirt portion 24 to the desired location. This step may be performed while the endoscope 500 is positioned within the access device 20, and without substantially disturbing the location of the proximal portion of the access device 20 to which the endoscope mount platform 300 may be attached.

FIGS. 26-27 illustrate one embodiment of a fastener 600 that is particularly applicable in procedures involving fixation. The fastener 600 preferably includes a screw portion 602, a housing 604, a spacer member 606, a biasing member 608, and a clamping member, such as a cap screw 610. The screw portion 602 has a distal threaded portion 612 and a proximal, substantially spherical joint portion 614. The threaded portion 612 is inserted into the hole that extends away from the entry point 92 into the vertebrae, as will be described below. The substantially spherical joint portion 614 is received in a substantially annular, partly spherical recess 616 in the housing 604 in a ball and socket joint relationship (see also FIG. 29).

As illustrated in FIG. 27, the fastener 600 is assembled by inserting the screw portion 602 into a bore in a passage 618 in the housing 604 until the joint portion 614 engages the annular recess 616. The screw portion 602 is retained in the housing 604 by the spacer member 606 and by the biasing member 608. The biasing member 608 provides a biasing force to drive the spacer member 606 into frictional engagement with the joint portion 614 of the screw member 602 and the annular recess 616 of the housing 604. The biasing provided by the biasing member 602 frictionally maintains the relative positions of the housing 604 with respect to the screw portion 602. The biasing member 608 preferably is selected such that biasing force prevents unrestricted movement of the housing 604 relative to the screw portion 602. However, in some embodiments the biasing force is insufficient to resist the application of force by a physician to move the housing 604 relative to the screw portion 602. In other words, this biasing force is strong enough maintain the housing 604 stationary relative to the screw portion 602, but this force may be overcome by the physician to reorient the housing 604 with respect to the screw member 602, as will be described below.

In the illustrated embodiment, the biasing member 608 is a resilient ring having a gap 620, which permits the biasing member 608 to radially contract and expand. FIG. 27(a) illustrates that the biasing member 608 may have an arched shape, when viewed end-on. The arched shape of the spring member 608 provides the biasing force, as will be described below. The spacer member 606 and the biasing member 608 are inserted into the housing 604 by radially compressing the biasing member into an annular groove 622 in the spacer member 606. The spacer member 606 and the biasing member 608 are slid into the passage 618 until the distal surface of the spacer member 606 engages the joint portion 614 of the screw portion 602, and the biasing member 608 expands radially into the annular groove 622 in the housing 604. The annular groove 622 in the housing 604 has a dimension 623 that is smaller than the uncompressed height of the arched shape of the biasing member 608. When the biasing member 608 is inserted in the annular groove 620, the biasing member 608 is flattened against its normal bias, thereby exerting the biasing force to the spacer member 606. It is understood that similar biasing members, such as coiled springs, belleville washers, or the like may be used to supply the biasing force described herein.

The spacer member 606 is provided with a longitudinal bore 626, which provides access to a hexagonal recess 628 in the proximal end of the joint portion 614 of the screw member 602. The proximal portion of the housing 604 includes a pair of upright members 630 and 631 that are separated by substantially "U"-shaped grooves 632. A recess for receiving elongated member 650 is defined by the pair of grooves 632 between upright members 630 and 631. Elongated member 650 preferably is configured to be placed distally into the housing 604 in an orientation substantially transverse to the longitudinal axis of the housing 604, as will be described below. The inner walls of he upright members 630 and 631 are provided with threads 634 for attachment of the cap screw 610 by threads 613 therein.

Additional features of the fastener 600 are also described in U.S. patent application Ser. No. 10/075,668, filed Feb. 13, 2002, published as U.S. application Publication No. 2003/0153911A1 on Aug. 14, 2003, and application Ser. No. 10/087,489, filed Mar. 1, 2002, published as U.S. application Publication No. 2003/0167058A1 on Sep. 4, 2003, which are incorporated by reference in their entireties herein.

According to one application, the fastener 600 is inserted into the access device 20 and guided to the prepared hole at the entry point 92 in the vertebrae. The fastener 600 preferably is simultaneously supported and advanced into the hole so that the fastener 600 is secured in the in the hole beneath the entry point 92. In the illustrated embodiment the fastener 600 is supported and attached to the bone by an endoscopic screwdriver apparatus 660, illustrated in FIGS. 28-29. The screwdriver 660 includes a proximal handle portion 662 (illustrated in dashed line), an elongated body portion 664, and a distal tool portion 666.

The distal tool portion 666, as illustrated in greater detail in FIG. 29 includes a substantially hexagonal outer periphery that is received in the substantially hexagonal recess 628 in the joint portion 614 of the screw member 602. A spring member at the distal tool portion 666 releasably engages the hexagonal recess 628 of the screw member 602 to support the fastener 600 during insertion and tightening. In the illustrated embodiment, a spring member 672 is configured to engage the side wall of the recess 628. More particularly, a channel or a groove is provided in the tip portion 666 for receiving the spring member 672. The channel or groove includes a medial longitudinal notch portion 676, a proximal, angled channel portion 678, and a distal substantially transverse channel portion 680. The spring member 672 is preferably manufactured from stainless steel and has a medial portion 682, proximal portion 684, and a transverse distal portion 686. The medial portion 682 is partially received in the longitudinal notch portion 676. The proximal portion 684 preferably is angled with respect to the medial portion 682 and is fixedly received in the angled channel portion 678. The transverse distal portion 686 preferably is slidably received in the transverse channel 680. The medial portion 682 of the spring member 672 is partially exposed from the distal tip portion 666 and normally is biased in a transverse outward direction with respect to the longitudinal axis (indicated by arrow E), in order to supply bearing force against the wall of the recess 628. Alternatively, the distal tip portion of the screwdriver may be magnetized in order to hold the screw portion 602. Similarly, the distal tip portion may include a ball bearing or similar member which is normally biased in a radially outward direction to engage the interior wall of the recess 628 to secure the fastener 600 to the screwdriver distal tip 666. Other means may be provided for temporarily but securely coupling the fastener 600 with the screwdriver distal tip 666.

The insertion of the fastener 600 into the prepared hole that extends into the vertebrae from the entry point 92 may be achieved by insertion of screwdriver 660 into access device 20 (indicated by arrow G). This procedure may be visualized by the use of the endoscope 500 in conjunction with fluoroscopy, or by way of any other suitable viewing element. The screw portion 602 is threadedly advanced by the endoscopic screwdriver 660 into the prepared hole that extends beneath the entry point 92 (indicated by arrow H). The endoscopic screwdriver 660 is subsequently separated from the fastener 600, by applying a force in the proximal direction, and thereby releasing the distal tip portion 666 from the hexagonal recess 628 (e.g., causing the transverse distal portion 686 of the spring member 672 to slide within the transverse recess 680 against the bias, indicated by arrow F), and removing the screwdriver 660 from the access device 20. An alternative method may use a guidewire, which is fixed in the hole beneath the entry point 92, and a cannulated screw which has an internal lumen and is guided over the guidewire into the hole beneath the entry point 92. Where a guidewire system is used, the screwdriver also would be cannulated so that the screwdriver would fit over the guidewire.

For a two-level fixation, it may be necessary to prepare several holes and attach several fasteners 600. Preferably, the access device 20 is sized to provide simultaneous access to all vertebrae in which the surgical procedure is being performed. In some cases, however, additional enlargement or repositioning of the distal portion of the access device 20 may be helpful in providing sufficient access to the outer vertebrae, e.g., the L4 and S1 vertebrae. In the illustrated embodiment, the expander apparatus 200 may be repeatedly inserted into the access device 20 and expanded in order to further open or to position the skirt portion 24. In one procedure, additional fasteners are inserted in the L4 and S1 vertebrae in a similar fashion as the fastener 600 inserted into the L5 vertebra as described above. (When discussed individually or collectively, a fastener and/or its individual components will be referred to by the reference number, e.g., fastener 600, housing 604, and all fasteners 600. However, when several fasteners and/or their components are discussed in relation to one another, an alphabetic subscript will be used, e.g., fastener 600a is moved towards fastener 600b.)

In one application, after the fasteners 600 are advanced into the vertebrae, the housing portions 604 of the fasteners 600 are substantially aligned such that their upright portions 630 and 631 face upward, and the notches 632 are substantially aligned to receive the elongated member 650 therein. The frictional mounting of the housing 604 to the screw member 602, described above, allows the housing 604 to be temporarily positioned until a subsequent tightening step is performed, described below.

Positioning of the housing portions 604 may be performed by the use of an elongated surgical instrument capable of contacting and moving the housing portion to the desired orientation. One such instrument for positioning the housings 604 is a grasper apparatus 700, illustrated in FIG. 30. The grasper apparatus 700 includes a proximal handle portion 702, an elongated body portion 704, and distal nose portion 706. The distal nose portion 706 includes a pair of grasping jaws 708a and 708b, which are pivotable about pin 710 by actuation of the proximal handle portion 702. The grasping jaws 708a and 708b are illustrated in the closed position in FIG. 30. Pivoting the movable handle 714 towards stationary handle 712 causes longitudinal movement of actuator 716, which in turn pivots the jaw 708b towards an open position (illustrated in dashed line). The biasing members 718 and 720 are provided to return the handles 712 and 714 to the open position and bias the jaws 708a and 708b to the closed position.

In one application, the elongated member 650 is inserted into the access device 20. In one application, the elongated member 650 is manufactured from a biocompatible material and is sufficiently strong to maintain the position of the vertebrae, or other body structures, coupled by the elongate member 650 with little or no relative motion therebetween. In one embodiment, the elongated members 650 are manufactured from Titanium 6/4 or titanium alloy. The elongated member 650 also may be manufactured from stainless steel or any other suitable material. The transverse shape, width (e.g., radii), and lengths of the elongated members 650 are selected by the physician to provide the best fit for the positioning of the screw heads. Such selection may be performed by placing the elongated member 650 on the skin of the patient overlying the location of the fasteners and viewed fluoroscopically. For example, a 70 mm preformed rod having a 3.5" bend radius may be selected for the spinal fixation.

Figure 30:
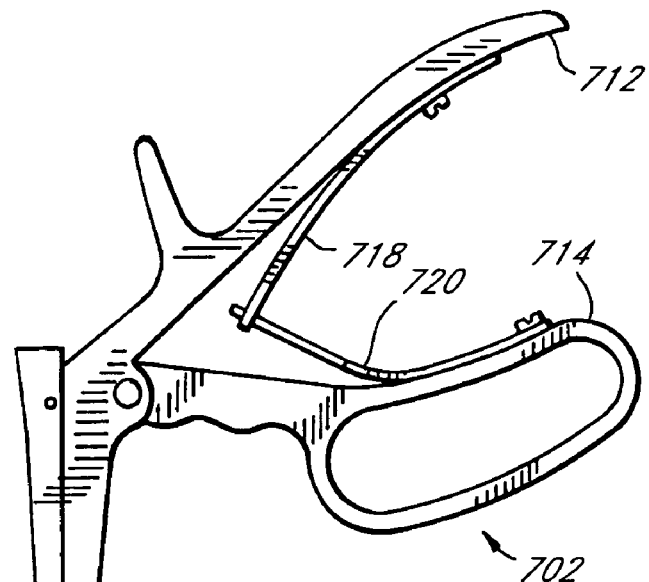
FIG. 30 is side view of one embodiment of another surgical instrument.

In one application, the elongated member 650 is fixed to each of the fasteners 600, and more particularly, to the housings 604 of each fastener 600. The grasper apparatus 700, described above, is also particularly useful for inserting the elongated member 650 into the access device 20 and positioning it with respect to each housing 604. As illustrated in FIG. 30, the jaws 708a and 708b of the grasper apparatus 700 each has shaped (e.g., curved) contact portions 722a and 722b for contacting and holding the outer surface of the elongated member 650.

Figure 31:
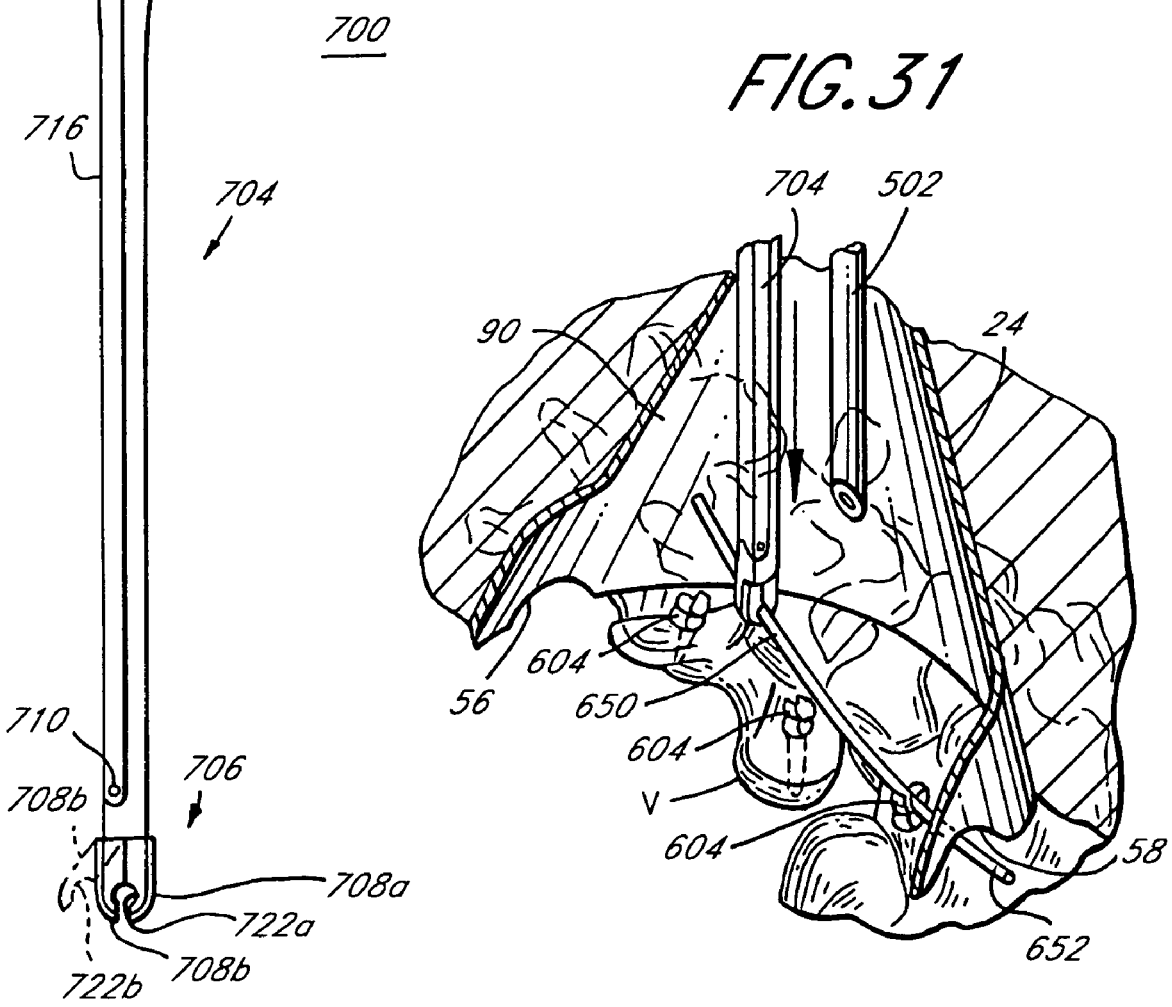
FIG. 31 is a partial sectional view of one stage of one application for treating the spine of a patient.

As illustrated in FIG. 31, the grasper apparatus 700 may be used to insert the elongated member 650 into the operative space 90 defined at least partially by the skirt portion 24 of the access device 20. In some embodiments, the cut-out portions 56 and 58 provided in the skirt portion 24 assist in the process of installing the elongated member 650 with respect to the housings 604. The cut-out portions 56 and 58 allow an end portion 652 of the elongated member 650 to extend beyond the operative space without raising or repositioning the skirt portion 24. The elongated member 650 is positioned within the recesses in each housing 604 defined by grooves 632 disposed between upright members 630 and 631. The elongated member 650 is positioned in an orientation substantially transverse to the longitudinal axis of each housing 604.

Further positioning of the elongated member 650 may be performed by guide apparatus 800, illustrated in FIG. 32. Guide apparatus 800 is useful in cooperation with an endoscopic screwdriver, such as endoscopic screwdriver 660 (illustrated in FIG. 28), in order to position the elongated member 650, and to introduce and tighten the cap screw 610, described above and illustrated in FIG. 27. Tightening of the cap screw 610 with respect to the housing 604 fixes the orientation of the housing 604 with respect to the screw portion 602 and fixes the position of the elongated member 650 with respect to the housings 604.

In the illustrated embodiment, the guide apparatus 800 has a proximal handle portion 802, an elongated body portion 804, and a distal tool portion 806. The elongated body portion 804 defines a central bore 808 (illustrated in dashed line) along its longitudinal axis 810. The central bore 808 is sized and configured to receive the endoscopic screwdriver 660 and cap screw 610 therethrough. In the exemplary embodiment, the diameter of the central bore 808 of the elongated body portion 804 is about 0.384-0.388 inches in diameter, and the external diameter of the endoscopic screwdriver 660 (FIG. 28) is about 0.25 inches. The proximal handle portion. 802 extends transverse to the longitudinal axis 810, which allows the physician to adjust the guide apparatus 800 without interfering with the operation of the screwdriver 660.

The distal portion 806 of the apparatus includes several shaped cut out portions 814 which assist in positioning the elongated member 650. As illustrated in FIG. 33, the cut out portions 814 are sized and configured to engage the surface of elongated member 650 and move the elongated member 650 from an initial location (illustrated in dashed line) to a desired location. In the illustrated embodiment, the cut out portions 814 are semicircular, to match the round elongated member 650. However, other shaped cut out portions may be provided to match other shaped elongated members.

As illustrated in FIG. 34, the guide apparatus 800 is used in cooperation with the endoscopic screwdriver 660 to attach the cap screw 610. The distal end of the body portion 804 includes a pair of elongated openings 816. The openings 816 provide a window to enable the physician to endoscopically view the cap screw 610 retained at the distal tip 666 of the endoscopic screw driver 660. Fewer or more than two openings can be provided and the openings 816 need not be elongated.

The guide apparatus 800 and the endoscopic screwdriver 660 cooperate as follows in one application. The guide apparatus 800 is configured to be positioned in a surrounding configuration with the screwdriver 600. In the illustrated embodiment, the body portion 804 is configured for coaxial placement about the screwdriver 660 in order to distribute the contact force of the guide apparatus 800 on the elongated member 650. The distal portion 806 of the guide apparatus 800 may bear down on the elongated member 650 to seat the elongated member 650 in the notches 632 in the housing 604. The "distributed" force of the guide apparatus 800 may contact the elongated member 650 on at least one or more locations. In addition, the diameter of central bore 808 is selected to be marginally larger than the exterior diameter of cap screw 610, such that the cap screw 610 may freely slide down the central bore 808, while maintaining the orientation shown in FIG. 34. This configuration allows the physician to have effective control of the placement of the cap screw 610 into the housing 604. The cap screw 610 is releasably attached to the endoscopic screwdriver 660 by means of spring member 672 engaged to the interior wall of hexagonal recess 611 as it is inserted within the bore 808 of the body portion 804 of guide apparatus 800. The cap screw 610 is attached to the housing 604 by engaging the threads 615 of the cap screw 610 with the threads 634 of the housing.

Figure 35:
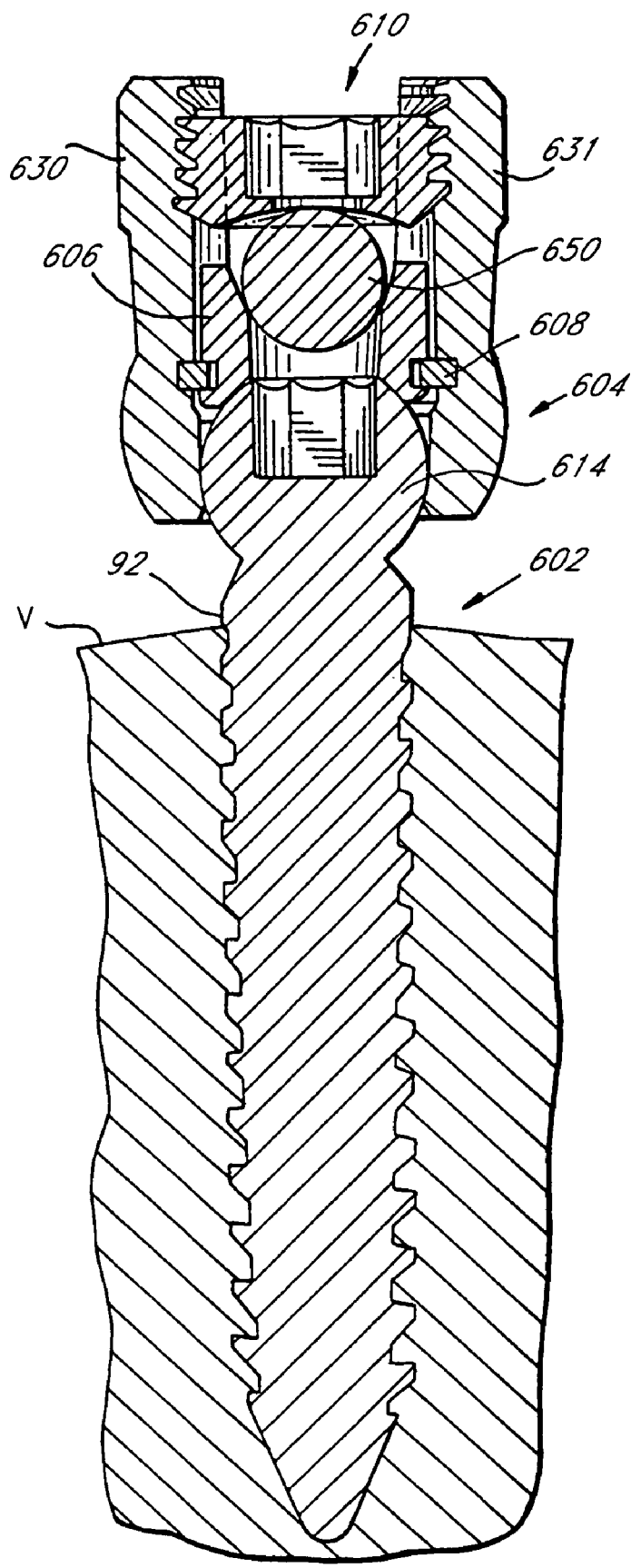
FIG. 35 is an enlarged sectional similar to FIG. 34, illustrating one stage of one application for treating the spine of a patient.

As illustrated in FIG. 35, tightening of the cap screw 610 fixes the assembly of the housing 604 with respect to the elongated member 650. In particular, the distal surface of the cap screw 610 provides a distal force against the elongated member 650, which in turn drives the spacer member 606 against the joint portion 614 of the screw portion 602, which is fixed with respect to the housing 604.

If locations of the vertebrae are considered acceptable by the physician, then the fixation procedure is substantially complete once the cap screws 610 have been attached to the respective housings 604, and tightened to provide a fixed structure as between the elongated member 650 and the various fasteners 600. However, if compression or distraction of the vertebrae with respect to one another is required additional apparatus would be used to shift the vertebrae prior to final tightening all of the cap screws 610.

In the illustrated embodiment, this step is performed with a surgical instrument, such as a compressor-distractor instrument 900, illustrated in FIG. 36, which is useful to relatively position bone structures in the cephcaudal direction and to fix their position with respect to one another. Thus, the compressor-distractor instrument 900 has the capability to engage two fasteners 600 and to space them apart while simultaneously tightening one of the fasteners to fix the spacing between the two vertebrae, or other bone structures. Moreover, the compressor-distractor instrument 900 may also be used to move two fasteners 600, and the vertebrae attached thereto into closer approximation and fix the spacing therebetween.

The distal tool portion 902 of one embodiment of the compressor-distractor instrument 900 is illustrated in FIG. 36. The distal tool portion 902 includes a driver portion 904 and a spacing member 906. The driver portion 904 has a distal end portion 908 with a plurality of wrenching flats configured to engage the recess 611 in the proximal face of the cap screw 610, and to apply torque to the cap screw. The driver portion 904 is rotatable about the longitudinal axis (indicated by arrow M) to rotate the cap screw 610 relative to the fastener 600. Accordingly, the driver portion 904 can be rotated to loosen the cap screw 610 on the fastener 600 and permit movement of the elongated member 650 connected with the vertebra relative to the fastener 600 connected with the vertebra. The cap screw 610 can also be rotated in order to tighten the cap screw 610 and clamp the elongated member 650 to the fastener 600.

The distal tool portion 902 may also include a spacing member, such as spacing member 906, which engages an adjacent fastener 600b while driver member 904 is engaged with the housing 604a to move the fastener 600b with respect to the fastener 600a. In the exemplary embodiment, spacing member 906 comprises a jaw portion that is pivotably mounted to move between a first position adjacent the driver portion and a second position spaced from the driver portion, as shown in FIG. 36. The distal tip 910 of the spacing member 906 is movable relative to the driver portion 904 in a direction extending transverse to the longitudinal axis. (Further details and features related to compressor-distractor apparatuses are described in U.S. application Ser. No. 10/178,875, filed Jun. 24, 2002, entitled "Surgical Instrument for Moving Vertebrae," published as U.S. patent application Publication No. 2003/0236529A1 on Dec. 25, 2003, which is incorporated by reference in its entirety herein. Additionally, further details related to instrumentation for moving a vertebra are described in U.S. Pat. No. 6,648,888, issued Nov. 18, 2003; PCT application No. PCT/US02/28106, filed Sep. 5, 2002, titled SURGICAL INSTRUMENT FOR MOVING VERTEBRAE; PCT application No. PCT/US03/27879, filed Sep. 5, 2003, titled SURGICAL INSTRUMENT FOR MOVING A VERTEBRAE; and PCT application No. PCT/US03/04361, filed Feb. 13, 2003, titled APPARATUS FOR CONNECTING A LONGITUDINAL MEMBER TO A BONE PORTION, which are hereby incorporated by reference in their entireties herein.)

As illustrated in FIG. 36, the spacer member 906 can be opened with respect to the driver portion 904 to space the vertebrae farther apart (as indicated by arrow N). The distal portion 910 of the spacer member 906 engages the housing 604b of fastener 600b and moves fastener 600b further apart from fastener 600a to distract the vertebrae. Where the vertebrae are to be moved closer together, e.g. compressed, the spacer member 906 is closed with respect to the driver portion 904 (arrow P), as illustrated in FIG. 37. The distal portion 910 of the spacer member 906 engages the housing 604b of the fastener 600b and moves the fastener 600b towards the fastener 600a. When the spacing of the vertebrae is acceptable to the physician, the cap screw 610a is tightened by the driver member 904, thereby fixing the relationship of the housing 604a with respect to the elongated member 650, and thereby fixing the position of the vertebrae, or other bone structures, with respect to one another. In one application, once the elongated member 650 is fixed with respect to the fasteners 600, the fixation portion of the procedure is substantially complete.

2. Fusion Systems and Devices

Although fixation may provide sufficient stabilization, in some cases it is also desirable to provide additional stabilization. For example, where one or more discs has degraded to the point that it needs to be replaced, it may be desirable to position an implant, e.g., a fusion device, a prosthetic disc, a disc nucleus, etc., in the intervertebral space formerly occupied by the disc.

Figure 48:
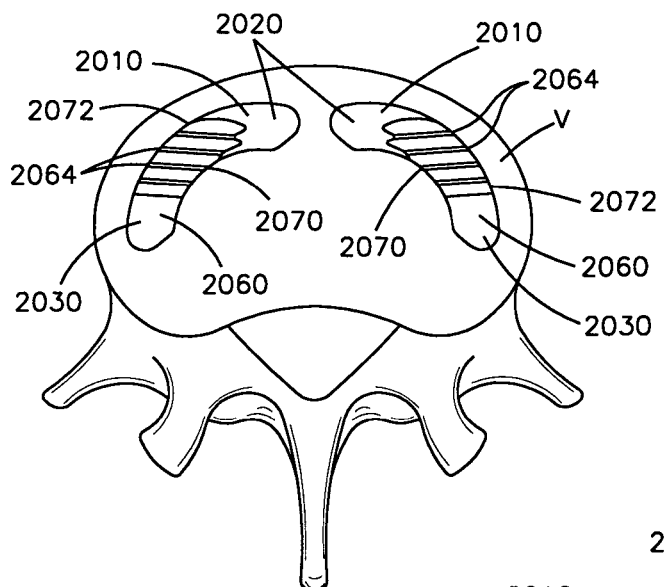
FIG. 48 is a view showing a pair of the spinal implants of FIG. 38 in first relative positions between adjacent vertebrae.
Figure 49:
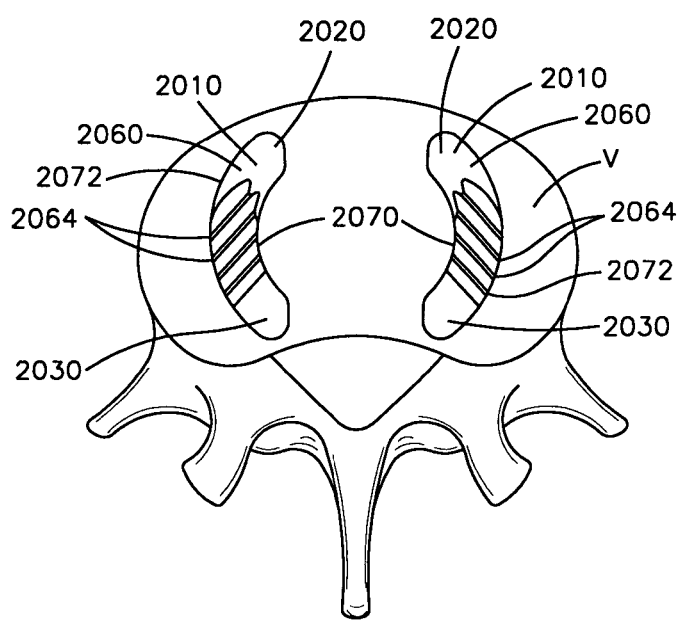
FIG. 49 is a view showing a pair of the spinal implants of FIG. 38 in second relative positions between adjacent vertebrae.

In one application, a fusion device is inserted between adjacent vertebrae V. Portions of the fusion procedure can be performed before, during, or after portions of the fixation procedure. FIGS. 38-42 illustrate one embodiment of a fusion device, referred to herein as a spinal implant 2010, that is inserted between adjacent vertebrae. The spinal implant 2010 preferably is placed between adjacent vertebrae to provide sufficient support to allow fusion of the adjacent vertebrae, as shown in FIGS. 48-49. The spinal implants 2010 are preferably made from an allograft material, though other materials could also be used, including autograft, xenograft, or some non-biologic biocompatible material, such as titanium or stainless steel. Also, where non-biologic materials are used, the implant 2010 may be configured as a cage or other suitable configuration.

Figure 41:
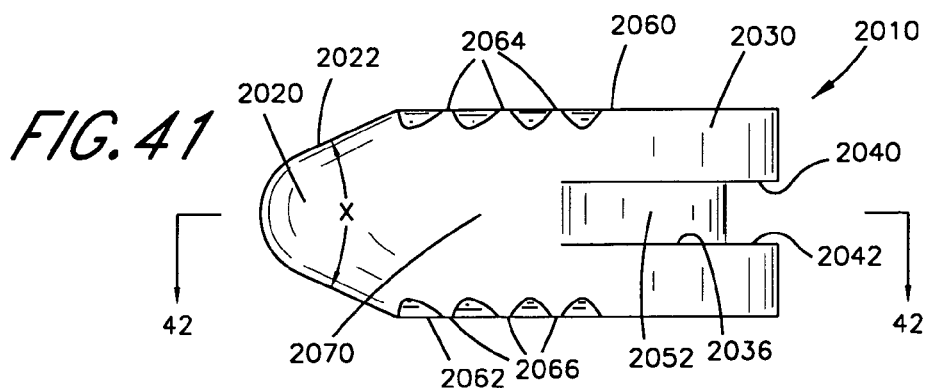
FIG. 41 is a side view of the spinal implant of FIG. 38 showing the first side surface.
Figure 42:
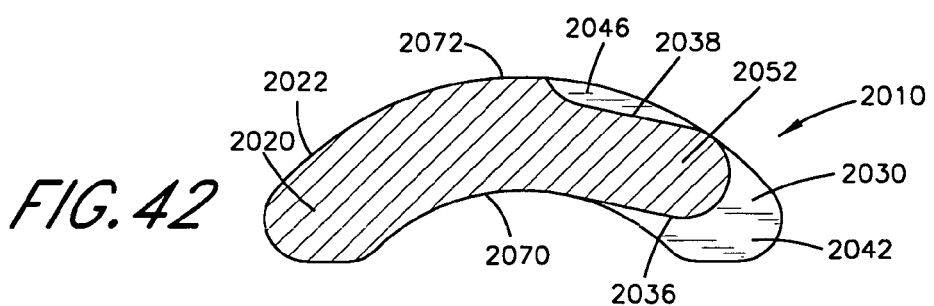
FIG. 42 is a cross-sectional view of the spinal implant taken along the line 42-42 in FIG. 41.

The spinal implant 2010 (FIGS. 38-42) has a first end 2020 for insertion between adjacent vertebrae V. The first end 2020 has a tapered surface 2022 to facilitate insertion of the implant between adjacent vertebrae V. The surface 2022 defines an angle X of approximately 45° as shown in FIG. 41.

Figure 51:
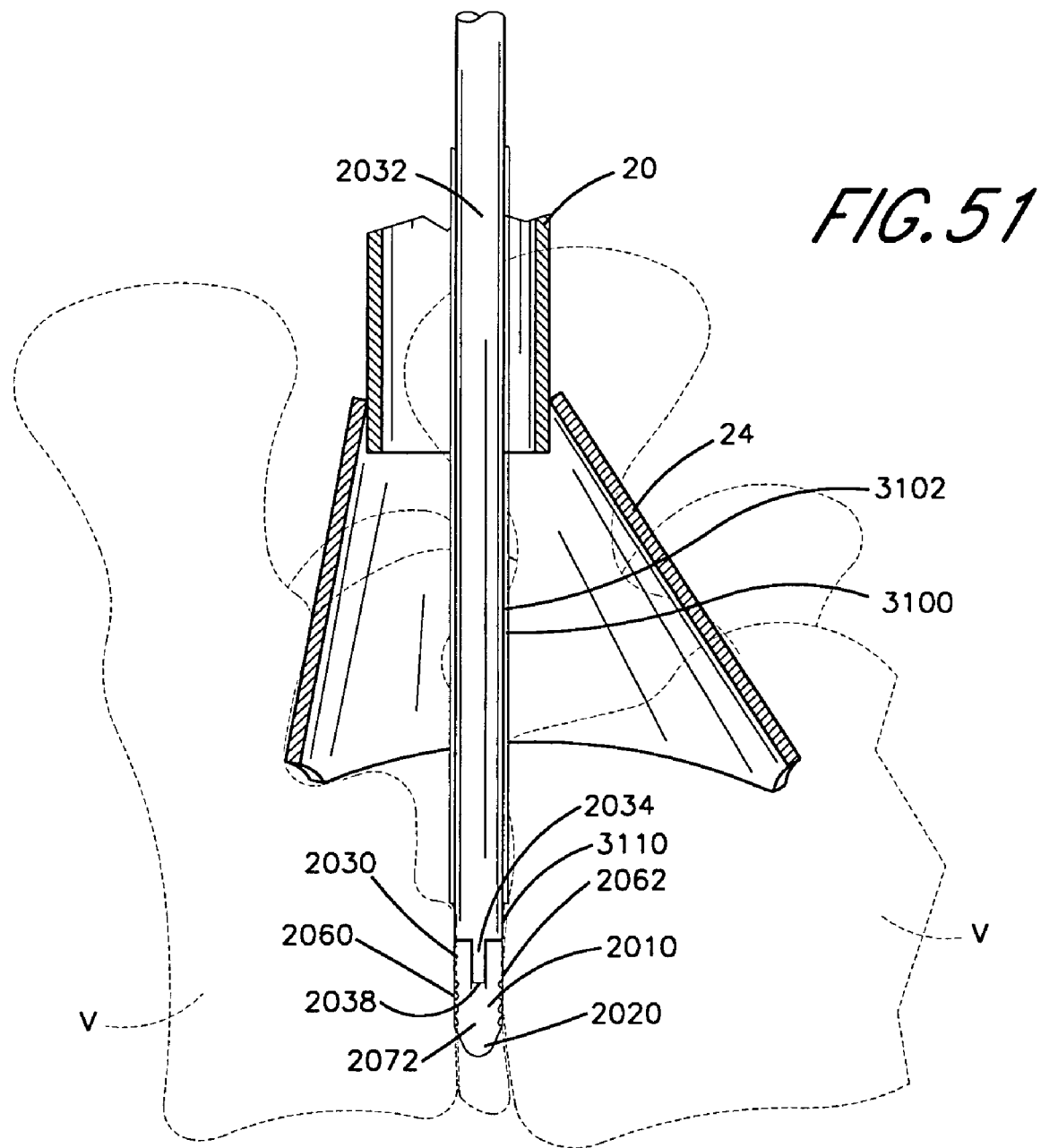
FIG. 51 is a view showing a spinal implant being inserted between the adjacent vertebrae according to one application.
Figure 52:
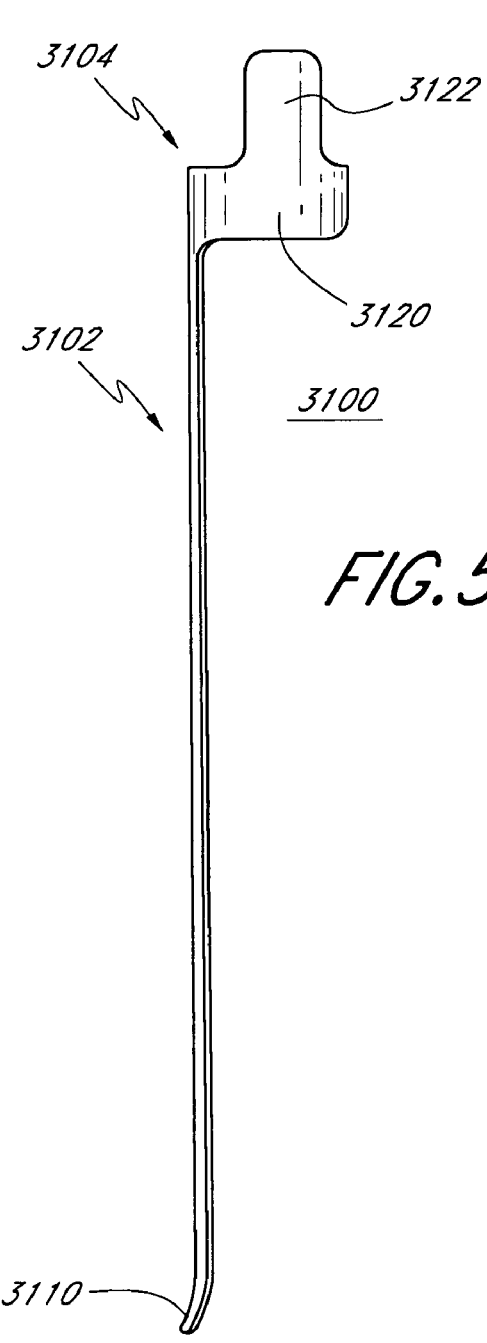
FIG. 52 is a side view of an apparatus according to another embodiment.
Figure 53:
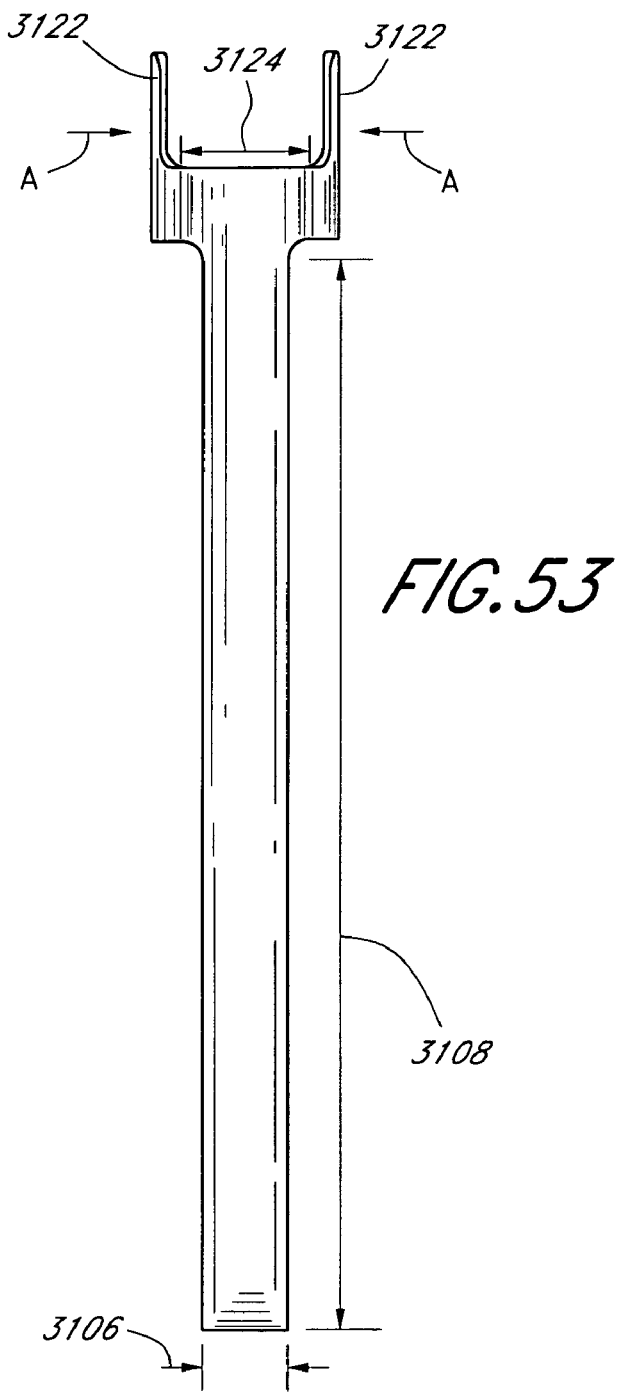
FIG. 53 is a front view of the apparatus of FIG. 52.
Figure 54:
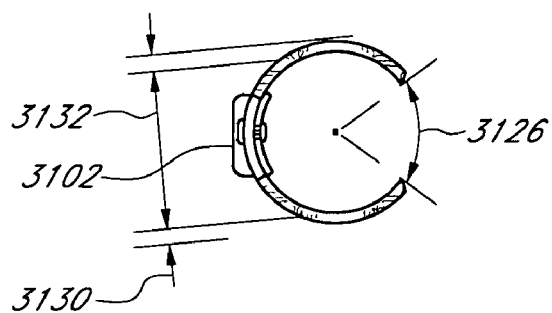
FIG. 54 is a top view of the apparatus of FIG. 52.
Figure 56:
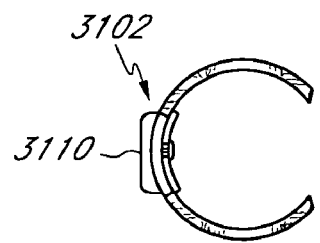
FIG. 56 is a bottom view of the apparatus of FIG. 52.
Figure 55:
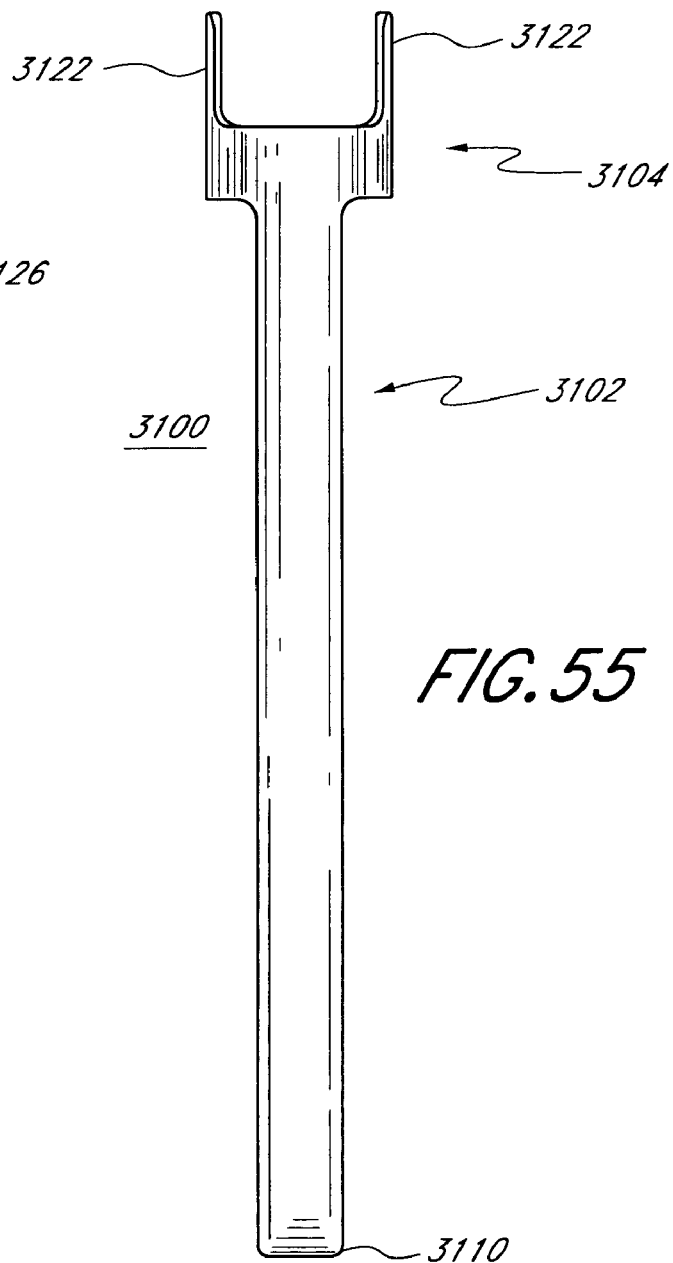
FIG. 55 is a back view of the apparatus of FIG. 52.

The spinal implant 2010 (FIGS. 38-39) has a second end 2030 that is engageable with a tool 2032 (FIG. 51) for inserting the implant between the adjacent vertebrae V. The tool 2032 has a pair of projections 2034, one of which is shown in FIG. 51, that extend into recesses 2036 and 2038 in the end 2030 of the implant 2010. The recesses 2036 and 2038 (FIGS.

38-39) extend from the second end 2030 toward the first end 2020. The recess 2036 (FIG. 41) is defined by an upper surface 2040 and a lower surface 2042 extending generally parallel to the upper surface 2040. The recess 2038 (FIG. 39) has a lower surface 2046 and an upper surface 2048. The upper surface 2048 extends generally parallel to the lower surface 2046.

The recesses 2036 and 2038 define a gripping portion 2052. The projections 2034 on the tool 2032 extend into the recesses 2036 and 2038 and grip the gripping portion 2052. The projections 2034 engage the upper and lower surfaces 2040 and 2042 of the recess 2036 and the upper and lower surfaces 2046 and 2048 of the recess 2038. Accordingly, the tool 2032 can grip the implant 2010 for inserting the implant between the adjacent vertebrae V.

Figures 38, 39:
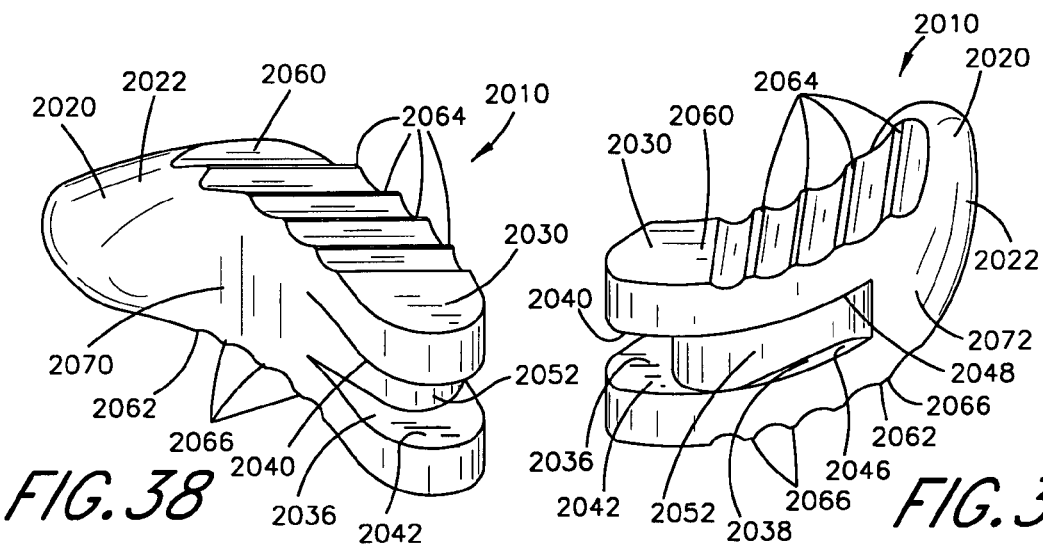
FIG. 38 is a perspective view of a spinal implant or fusion device constructed according to another embodiment showing a first side surface of the spinal implant.
FIG. 39 is a perspective view of the spinal implant of FIG. 38 showing a second side surface of the spinal implant.
Figure 40:
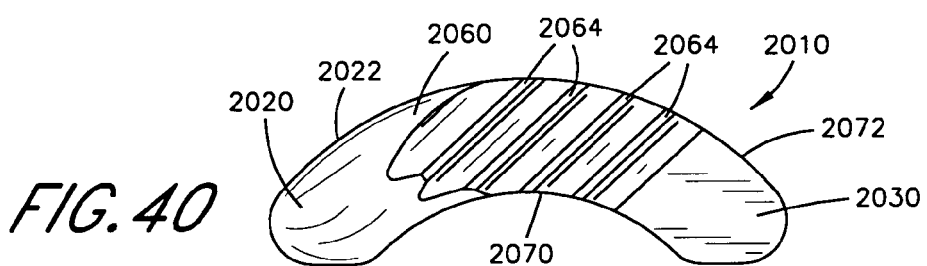
FIG. 40 is a plan view of the spinal implant of FIG. 38 showing an upper surface of the spinal implant.

As viewed in FIGS. 38-41, the implant 2010 has an upper surface 2060 for engaging the upper vertebra V. The implant 2010 has a lower surface 2062, as viewed in FIGS. 38-41, for engaging the lower vertebra V. The upper and lower surfaces 2060 and 2062 extend from the first end 2020 to the second end 2030 of the implant 2010 and parallel to the upper and lower surfaces 2040, 2042, 2046, and 2048 of the recesses 2036 and 2038. The upper surface 2060 has teeth 2064 for engaging the upper vertebra V. The lower surface 2062 has teeth 2066 for engaging the lower vertebra V. Although FIGS. 38-39 show four teeth 2064 and four teeth 2066, it is contemplated that any number of teeth could be used.

A first side surface 2070 and a second side surface 2072 extend between the upper and lower surfaces 2060 and 2062. The first side surface 2070 extends along a first arc from the first end 2022 of the implant 2010 to the second end 2030. The second side surface 2072 extends along a second arc from the first end 2022 to the second end 2030. The first and second side surfaces 2070 and 2072 are concentric and define portions of concentric circles. The teeth 2064 and 2066 extend parallel to each other and extend between the side surfaces 2070 and 2072 and along secant lines of the concentric circles defined by the side surfaces.

The implant 2010 preferably is formed by harvesting allograft material from a femur, as known in the art. The femur is axially cut to form cylindrical pieces of allograft material. The cylindrical pieces are then cut in half to form semi-cylindrical pieces of allograft material. The semi-cylindrical pieces of allograft material are machined into the spinal implants 2010.

A pair of spinal implants 2010 may be placed bilaterally between the adjacent vertebrae V. The access device 20 is positioned in the patient's body adjacent the vertebrae V. The skirt portion 24 of the access device 20 preferably is in a radially expanded condition to provide a working space adjacent the vertebrae V as described above. Disc material between the vertebrae V can be removed using instruments such as kerrisons, rongeurs, or curettes. A microdebrider may also be utilized to remove the disc material. An osteotome, curettes, and scrapers can be used to prepare end plates of the vertebrae V for fusion. Preferably, an annulus of the disc is left between the vertebrae V.

Distracters can be used to sequentially distract the disc space until the desired distance between the vertebrae V is achieved. The fusion device or implant 2010 is placed between the vertebrae V using the tool 2032. The first end 2020 of the implant 2010 is inserted first between the vertebrae V. The implant 2010 is pushed between the vertebrae V until the end 2030 of the implant is between the vertebrae. A second spinal implant 2010 is inserted on the ipsilateral side using the same procedure.

A shield apparatus 3100 with an elongated portion 3102 may be used to facilitate insertion of the implants 2010 between the vertebrae V. A distal portion 3110 of the apparatus 3100 may be placed in an annulotomy. The implant 2010 is inserted with the side surface 2170 facing the elongated portion 3102 so that the apparatus 3100 can act as a "shoe horn" to facilitate or guide insertion of the implants 2010 between the vertebrae.

The implants 2010 may be inserted between the vertebrae V with the first ends 2020 located adjacent each other and the second ends 2030 spaced apart from each other, as shown in FIG. 48. The implants 2010 may also be inserted between the vertebrae V with the first ends 2020 of the implants 2010 spaced apart approximately the same distance that the second ends 2030 are spaced apart. It is contemplated that the implants 2010 may be inserted in any desired position between the vertebrae V. It is also contemplated that in some embodiments only one implant 2010 may be inserted between the vertebrae V. Furthermore, it is contemplated that the implants 2010 may be inserted between vertebrae using an open procedure.

Figure 50:
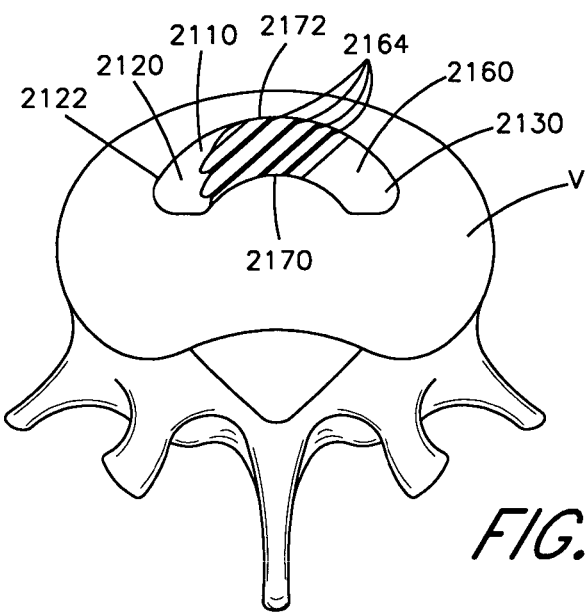
FIG. 50 is a view showing the spinal implant of FIG. 43 between adjacent vertebrae.

Another embodiment of a fusion device or spinal implant 2110 is illustrated in FIGS. 43-47. The spinal implant 2110 is substantially similar to the embodiment disclosed in FIGS. 38-42. The implant 2110 is placed between the adjacent vertebrae V to provide sufficient support to allow fusion of the adjacent vertebrae, as shown in FIG. 50. The spinal implant 2110 is preferably made from an allograft material, though the materials described above in connection with the spinal implant 2010 may also be used. Also, as with the implant 2010, the implant 2110 may be formed as a cage or other suitable configuration.

The spinal implant 2110 (FIGS. 4347) has a first end 2120 for insertion between the adjacent vertebrae V. The first end 2120 has a tapered surface 2122 to facilitate insertion of the implant between the adjacent vertebrae V. The surface 2122 defines an angle Y of approximately 45° as shown in FIG. 65.

The spinal implant 2110 (FIGS. 43-44) has a second end 2130 that is engageable with the projections 2034 on the tool 2032 for inserting the implant between the adjacent vertebrae V. The projections 2034 extend into recesses 2136 and 2138 in the end 2130 of the implant 2110. The recesses 2136 and 2138 extend from the second end 2130 toward the first end 2120. The recess 2136 (FIGS. 43 and 46) is defined by an upper surface 2140 and a lower surface 2142 extending generally parallel to the upper surface 2140. The recess 2138 (FIGS. 44) has a lower surface 2146 and an upper surface 2148 extending generally parallel to the lower surface 2146.

The recesses 2136 and 2138 define a gripping portion 2152. The projections 2034 on the tool 2032 extend into the recesses 2136 and 2138 and grip the gripping portion 2152. The projections 2034 engage the upper and lower surfaces 2140 and 2142 of the recess 2136 and the upper and lower surfaces 2146 and 2148 of the recess 2138. Accordingly, the tool 2032 can grip the implant 2110 for inserting the implant between the adjacent vertebrae V.

As viewed in FIGS. 43-46, the implant 2110 has an upper surface 2160 for engaging the upper vertebra V. The implant 2110 has a lower surface 2162, as viewed in FIGS. 43-46, for engaging the lower vertebra V. The upper and lower surfaces 2160 and 2162 extend from the first end 2120 to the second end 2130 of the implant 2110 and parallel to the upper and lower surfaces 2140, 2142, 2146, and 2148 of the recesses 2136 and 2138. The upper surface 2160 has teeth 2164 for engaging the upper vertebra V. The lower surface 2162 has teeth 2166 for engaging the lower vertebra V. Although FIG.

44 shows four teeth 2164 and four teeth 2166, it is contemplated that any number of teeth could be used.

A first side surface 2170 and a second side surface 2172 extend between the upper and lower surfaces 2160 and 2162. The first side surface 2170 extends along a first arc from the first end 2122 of the implant 2110 to the second end 2130. The second side surface 2172 extends along a second arc from the first end 2120 to the second end 2130. The first and second side surfaces 2170 and 2172 are concentric and define portions of concentric circles. The teeth 2164 and 2166 extend parallel to each other and between the side surfaces 2170 and 2172 along secant lines of the concentric circles defined by the side surfaces.

The implant 2110 preferably is formed by harvesting allograft material from a femur, as is known in the art. The femur is axially cut to form cylindrical pieces of allograft material. The cylindrical pieces are then cut in half to form semi-cylindrical pieces of allograft material. The semi-cylindrical pieces of allograft material are machined into the spinal implants 2110.

A spinal implant 2110 is placed unilaterally between the adjacent vertebrae V. The access device 20 is positioned in the patient's body adjacent the vertebrae V. The skirt portion 24 of the access device 20 preferably is in a radially expanded condition to provide a working space adjacent the vertebrae V as described above. Disc material between the vertebrae V can be removed using instruments such as kerrisons, rongeurs, or curettes. A microdebrider may also be utilized to remove the disc material. An osteotome, curettes, and scrapers can be used to prepare end plates of the vertebrae V for fusion. Preferably, an annulus of the disc is left between the vertebrae V.

Distracters are used to sequentially distract the disc space until the desired distance between the vertebrae V is achieved. The implant 2110 is placed between the vertebrae V using the tool 2032. It is contemplated that the apparatus 3100 could be used also. The first end 2120 of the implant 2110 is inserted first between the vertebrae V. The implant 2110 is pushed between the vertebrae V until the end 2130 of the implant is between the vertebrae. It is contemplated that the implant 2110 may be inserted in any desired position between the vertebrae V. It is also contemplated that in some embodiments more than one implant 2110 may be inserted between the vertebrae.

The apparatus or shield 3100 for use in placing the fusion devices or spinal implants between the vertebrae is illustrated in FIGS. 52-56. The apparatus 3100 preferably includes an elongated body portion 3102, which protects the nerve root or dura, and a mounting portion 3104, which allows for the surgeon to releasably mount the apparatus 3100 to the access device 20. Consequently, the surgeon is able to perform the surgical procedures without requiring the surgeon or an assistant to continue to support the apparatus 3100 throughout the procedure, and without reducing the field of view.

The apparatus 3100 may be manufactured from a biocompatible material such as, for example, stainless steel. In the illustrated embodiment, apparatus 3100 is manufactured from stainless steel having a thickness of about 0.02 inches to about 0.036 inches. The elongated body portion 3102 has dimensions that correspond to the depth in the body in which the procedure is being performed, and to the size of the body structure that is to be shielded by elongated body portion 3102. In the exemplary embodiment, the elongated body portion 3102 has a width 3106 of about 0.346 inches and a length of about 5.06 inches (FIG. 53), although other dimensions would be appropriate for spinal surgical procedures performed at different locations, or for surgical procedures involving different body structures. The distal tip portion 3110 of the apparatus 3100 may have a slightly curved "bell mouth" configuration which allows for atraumatic contact with a body structure, such as a nerve. It is contemplated that the elongated body portion may have any desired shape.

The mounting portion 3104 preferably allows the apparatus 3100 to be secured to a support structure in any number of ways. In the exemplary embodiment, mounting portion 3104 may include a ring portion. With reference to FIGS. 52-56, ring portion 3120 has a substantially ring-shaped configuration with an opening 3124, which defines an angle 3126 of about 90 degrees of the total circumference of the ring portion 3120. As will be described in greater detail below, the angle 3126 is a nominal value, because the ring portion 3104 is resilient, which permits the opening 3124 to change size during the mounting process.

In the illustrated embodiment, the mounting portion 3104 has a substantially cylindrical configuration in order to be mounted within the interior lumen of the access device 20, as will be described below. The ring portion 3104 has an exterior dimension 3130 of about 0.79 inches, and an interior dimension 3132 of about 0.76 inches. It is understood that the dimensions of the ring portion 3104 can be different, such as, for example, where the access device 20 has a different interior dimension. Moreover, the cylindrical shape of the ring portion 3104 can change, such as, for example, where the apparatus 3100 is used with a support member having a differently shaped internal lumen.

Finger grip portions 3122 preferably extend from the mounting portion 3104 and allow the surgeon to apply an inwardly directed force (as indicated by arrows A) to the ring portion 3120. The resilient characteristics of the ring portion 3120 allow the material to deflect thereby reducing the exterior dimension 3130 and reducing the spacing 3124. Releasing the finger grip portions 3122 allows the ring portion to move towards its undeflected condition, thereby engaging the interior wall of the access device 20.

The elongated body portion 3102 and the mounting portion 3104 may be manufactured from a single component, such as a sheet of stainless steel, and the mounting portion 3104 may be subsequently formed into a substantially cylindrical shape. In another embodiment, the mounting portion 3104 may be manufactured as a separate component and coupled to the elongated body portion, by techniques such as, for example, welding and/or securement by fasteners, such as rivets.

The access device 20 serves as a stable mounting structure for apparatus 3100. In particular, mounting portion 3104 is releasably mounted to the interior wall of proximal wall portion 22 of access device 20. Elongated body portion 3102 extends distally into the operative site to protect the desired body structure, such as the nerve, as will be described below.

Figure 58:
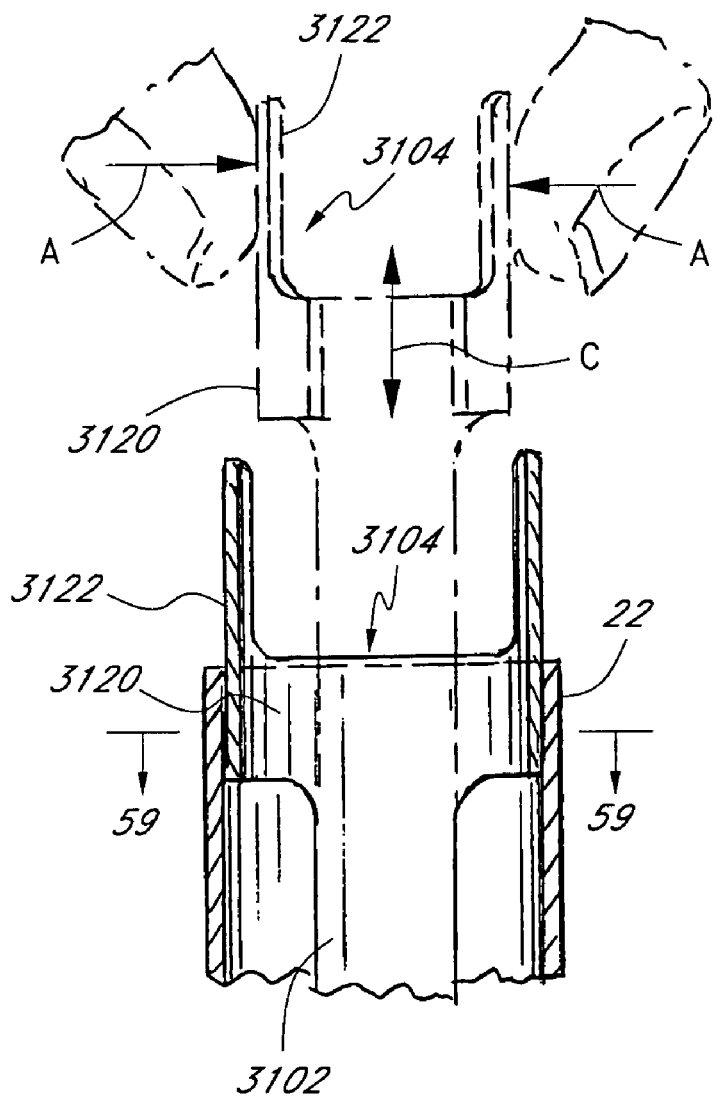
FIG. 58 is a longitudinal sectional view of the apparatus of FIG. 57 taken from line 58-58 of FIG. 57.
Figure 59:
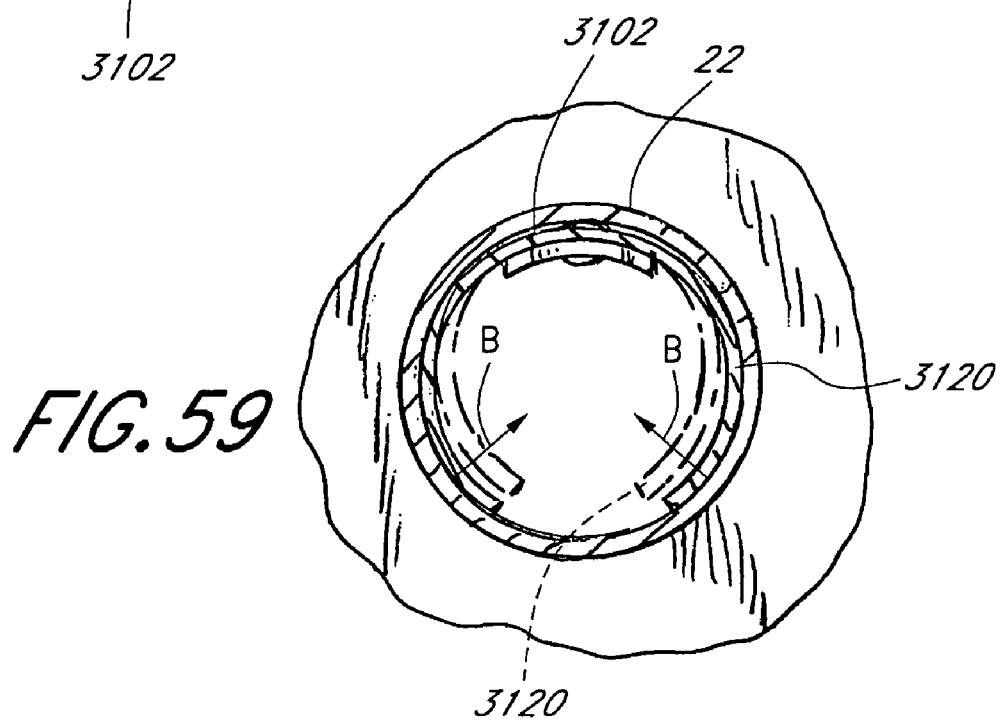
FIG. 59 is a transverse sectional view of the apparatus of FIG. 58 taken from line 59-59 of FIG. 58.

To install the apparatus 3100 within the interior passage of the proximal wall portion 22, the surgeon may apply an inwardly directed force on the ring portion 3120, thereby causing the ring portion to resiliently deform, as illustrated by dashed line and arrows B in FIG. 59. The surgeon subsequently inserts the apparatus 3100 into the interior lumen of the proximal wall portion 22 (as indicated by arrow C) to the position of ring portion 3104 illustrated in solid line in FIG. 58. When the surgeon releases the finger grip portions 3122, the ring portion 3120 resiliently moves towards its undeflected configuration, thereby engaging the interior lumen of the proximal wall portion 22. Advantages of some embodiments include that the mounting portion 3104 is easily removed and/or moved with respect to the access device 20 without disturbing the position of the access device 20 or any other instrumentation.

Figure 57:
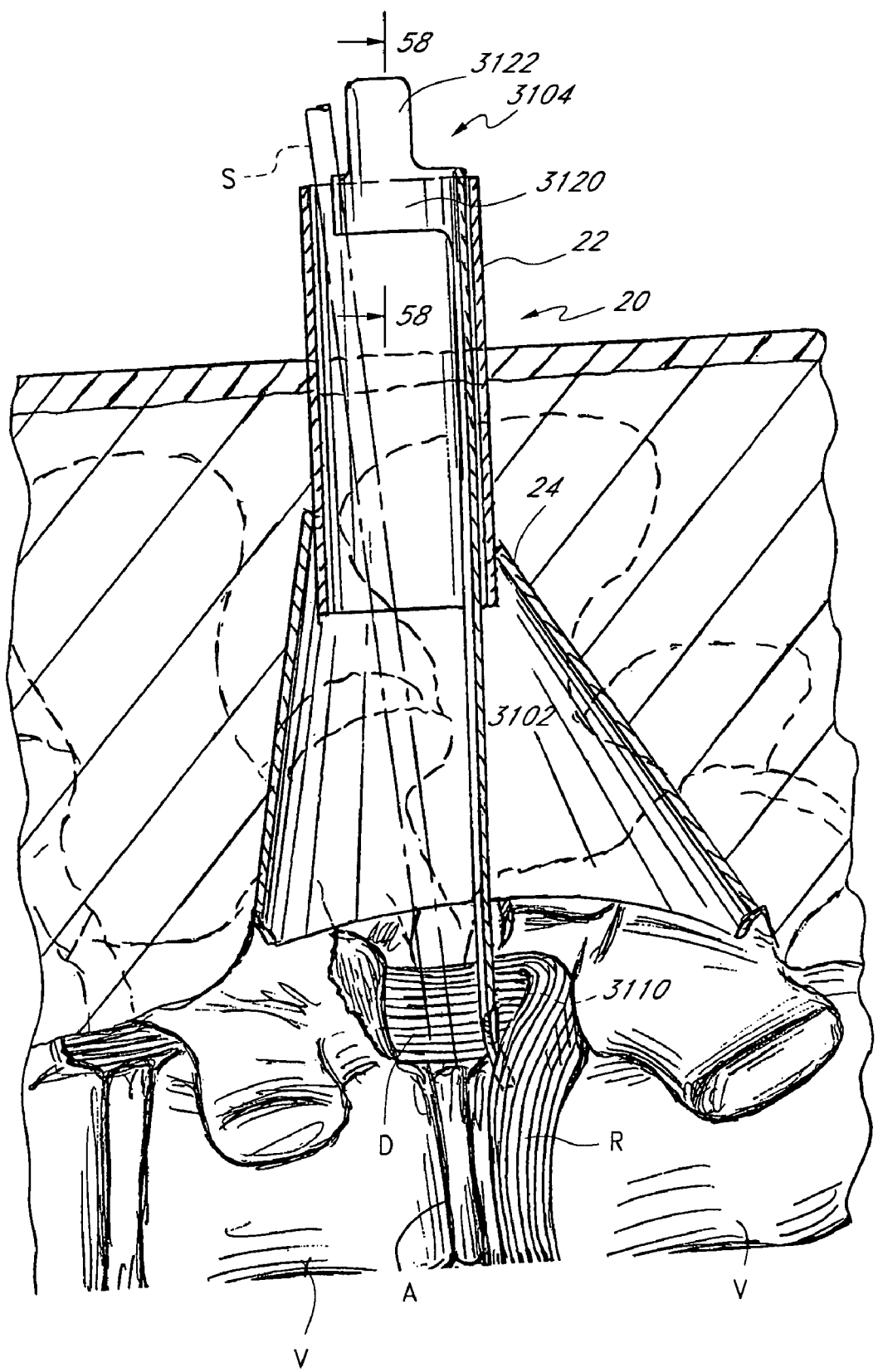
FIG. 57 is a sectional view of the apparatus of FIG. 52, used in conjunction with additional structure in a patient.

As illustrated in FIG. 57, the configuration of the mounting portion 3104 and the elongated body portion 3102 allow the elongated body portion to occupy a small space along the periphery of the proximal wall portion 3122. This allows the apparatus to protect the desired body structure without blocking access for the insertion of other surgical instrumentation, and without blocking visibility by the surgeon during the procedure.

The mounting portion 3104 is one exemplary configuration for mounting the apparatus 3100 to the support structure. It is contemplated that the apparatus 3100 may be mounted within the access device 20 in any suitable manner.

When in position, the distal end portion 3110 covers the exiting nerve root R, while exposing the disc annulus A (See FIG. 57). As discussed above, the debridement and decortication of tissue covering the vertebrae, as well as a facetectomy and/or laminectomy if indicated, are preferably performed prior to the insertion of apparatus 3100 into the surgical space. Accordingly, in some embodiments, there is no need to displace or retract tissue, and apparatus 3100 merely covers the nerve root and does not substantially displace the nerve root or any other body tissue. It is understood that the term "cover" as used herein refers to apparatus 3100 being adjacent to the body structure, or in contact with the body structure without applying significant tension or displacement force to the body structure.

Additional surgical instrumentation S may be inserted into the access device to perform procedures on the surrounding tissue. For example, an annulotomy may be performed using a long handled knife and kerrisons. A discectomy may be completed by using curettes and rongeurs. Removal of osteophytes which may have accumulated between the vertebrae may be performed using osteotomes and chisels.

Figure 60:
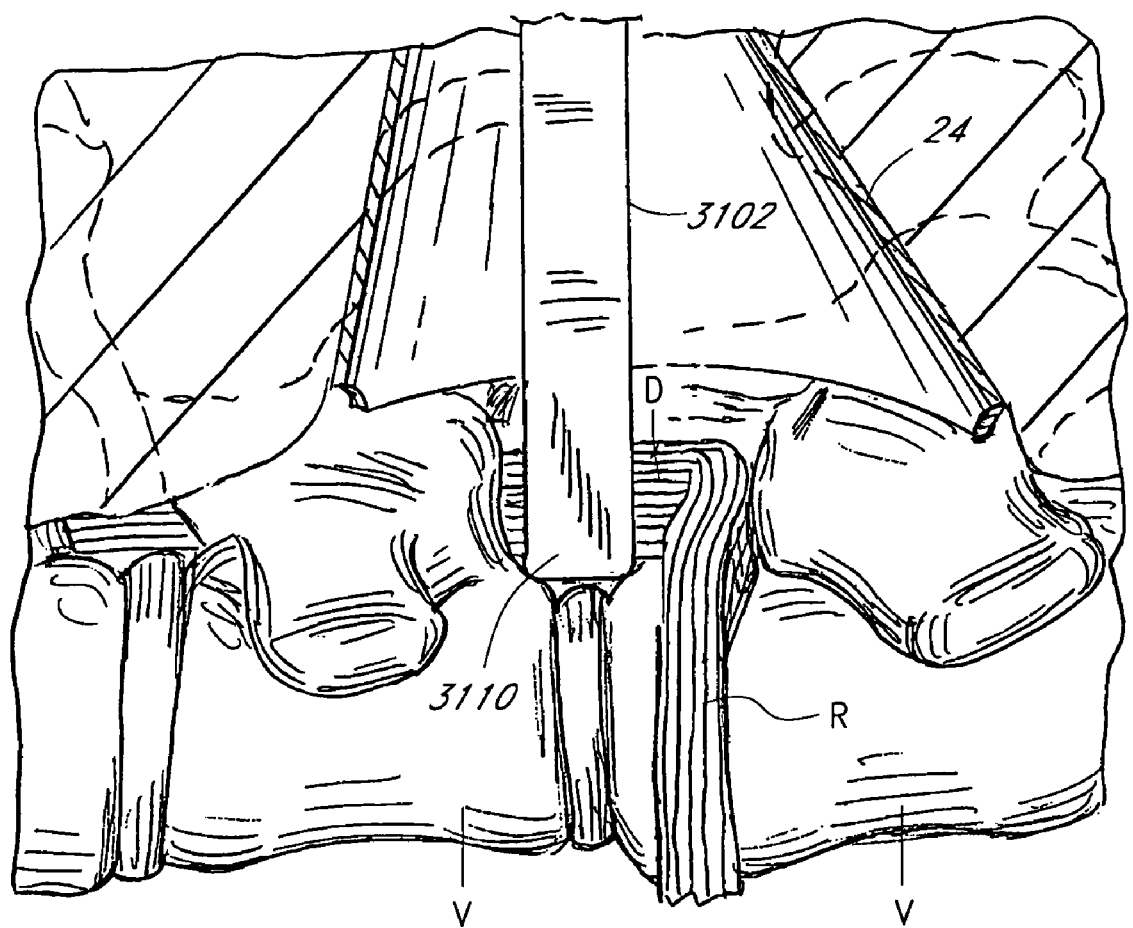
FIG. 60 is a sectional view, similar to FIG. 57, illustrating an alternative position of the apparatus of FIG. 52.

As illustrated in FIG. 60, the elongated body portion 3102 preferably is rotated to protect the spinal cord, or dura D, during the above procedures. The surgeon may change the position of the apparatus 3100 by approximating the finger grips 3122 to release the ring portion from engagement with the inner wall of the proximal wall portion 20, and then re-position the apparatus 3100 without disturbing the access device 20 (as shown in FIG. 58).

Figure 61:
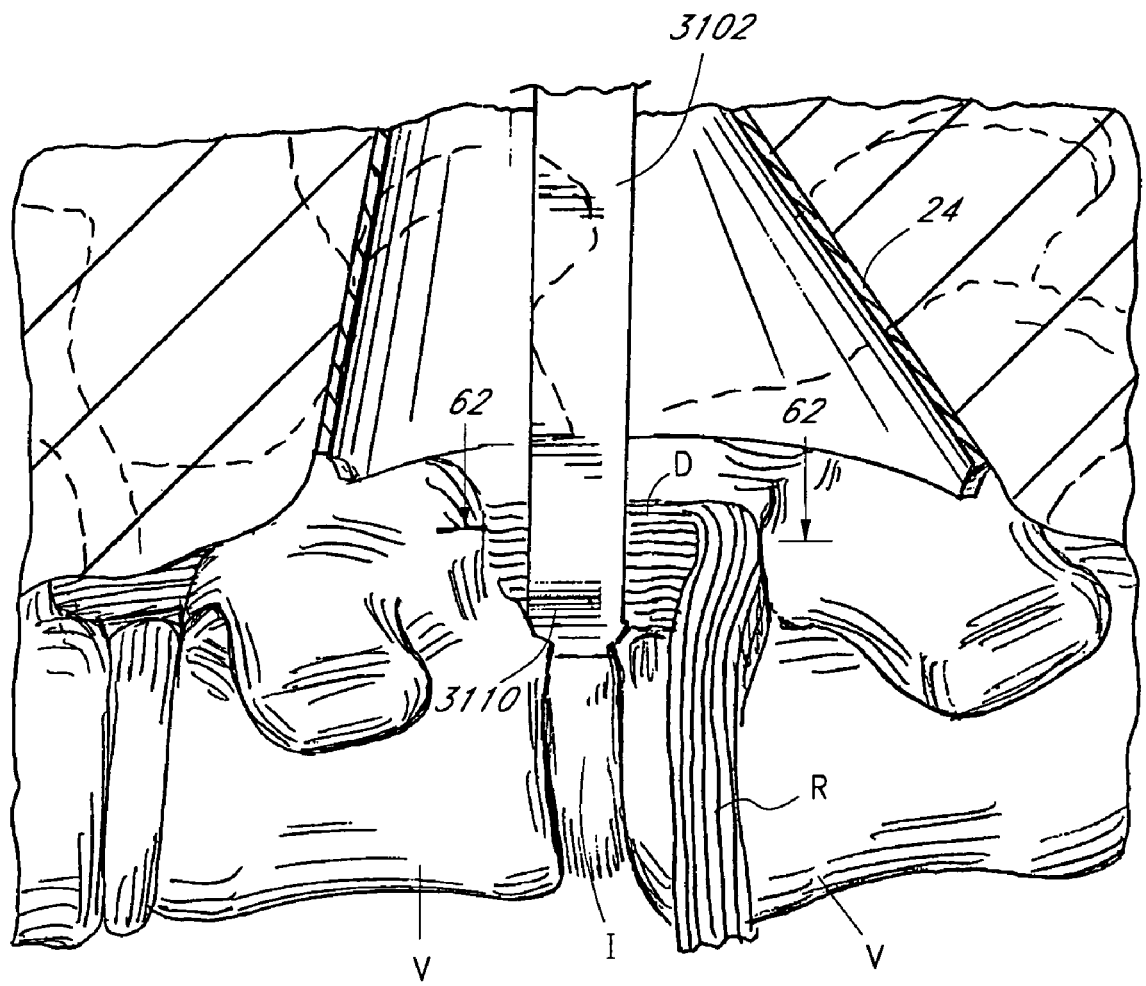
FIG. 61 is a sectional view, similar to FIG. 57, illustrating another alternative position of the apparatus of FIG. 52.
Figure 62:
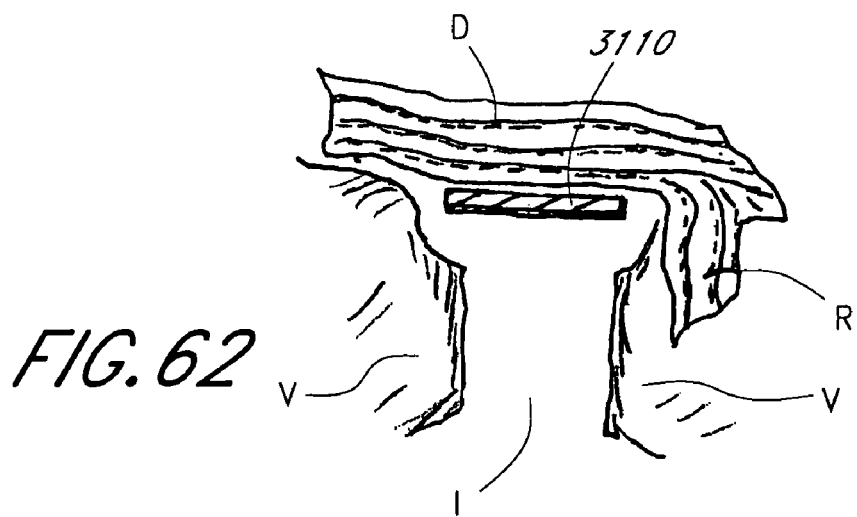
FIG. 62 is a transverse sectional view of the apparatus of FIG. 61, taken along lines 62-62 of FIG. 61.

During certain surgical procedures, it may be useful to introduce crushed bone fragments or the fusion devices 2010 or 2110 to promote bone fusion. As illustrated in FIGS. 61-62, apparatus 3100 is useful to direct the implants into the space I between adjacent vertebrae V. As shown in the figures, the distal portion 3110 of the elongated body portion 3102 is partially inserted into the space I. The distal end portion 3110, is positioned between adjacent vertebrae V, and creates a partially enclosed space for receiving the implants or other material therein.

Another embodiment of the apparatus or shield is illustrated in FIGS. 63-64, and designated apparatus 3200. Apparatus 3200 is substantially identical to apparatus 3100, described above, with the following differences noted herein. In particular, distal end portion 3210 includes a pair of surfaces 3240 and 3242. Surface 3240 is an extension of elongated shield portion 3202, and surface 3242 extends at an angle with respect to surface 3240. In the exemplary embodiment, surfaces 3240 and 3242 defined an angle of about 90 degrees between them. Alternatively another angle between surfaces 3240 and 3242 may be defined as indicated by the body structures to be protected.

Figure 65A:
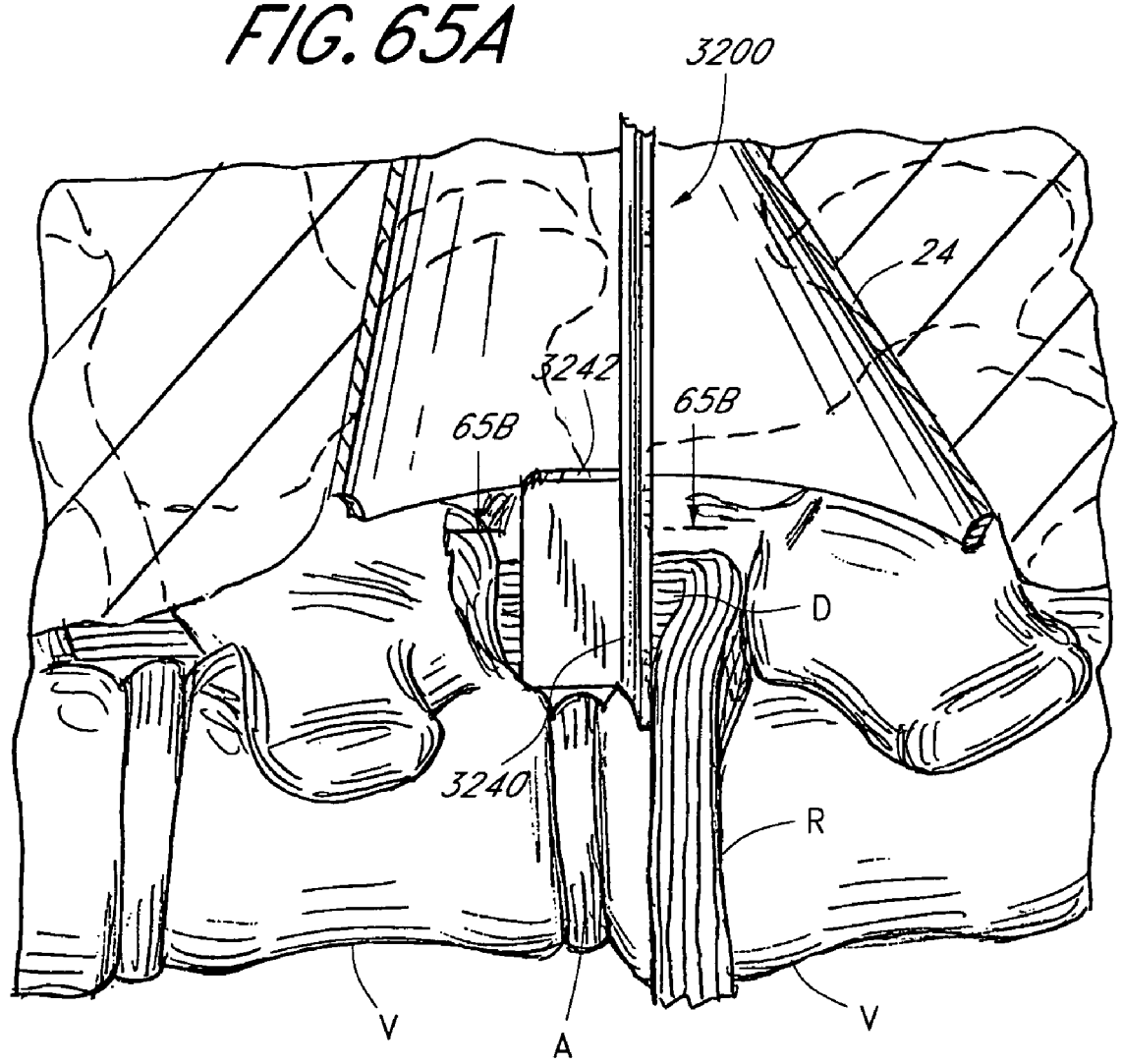
FIG. 65A is a sectional view, similar to FIG. 57, of the apparatus of FIG. 63, used in conjunction with additional structure in a patient.
Figure 65B:
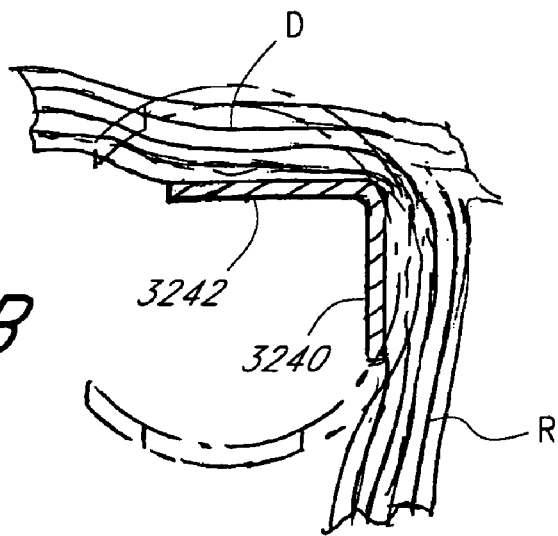
FIG. 65B is a transverse sectional view of the apparatus of FIG. 63, taken along lines 65B-65B of FIG. 65.
Figure 66A:
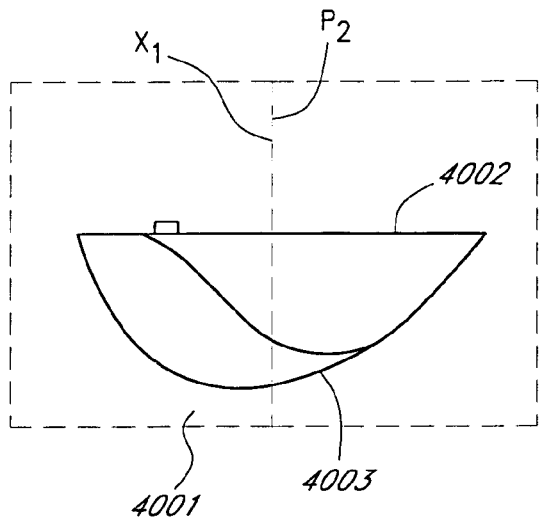
FIG. 66A is a side elevation view of a first portion of one embodiment of a spinal implant configured to preserve a degree of motion.
Figure 66B:
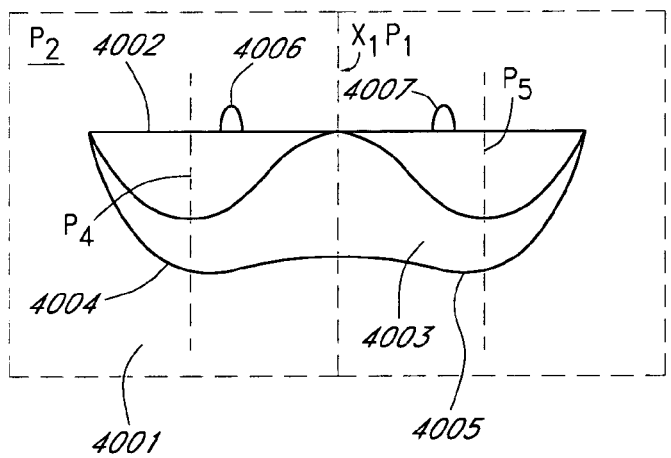
FIG. 66B is a rear or posterior elevation view of the first portion of FIG. 66A.
Figure 66C:
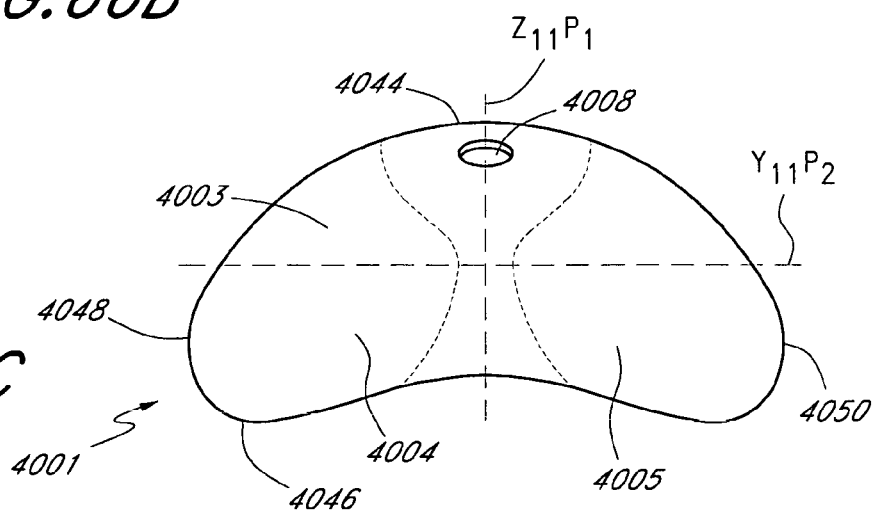
FIG. 66C is a bottom or inferior plan view of the first portion of FIG. 66A.
Figure 67A:
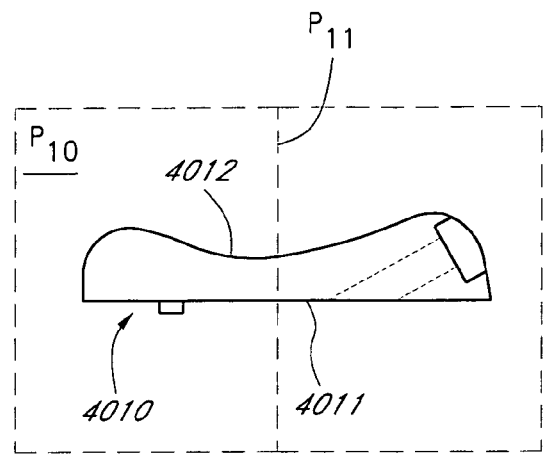
FIG. 67A is a side or lateral elevation view of a second portion of one embodiment of a spinal implant.
Figure 67B:
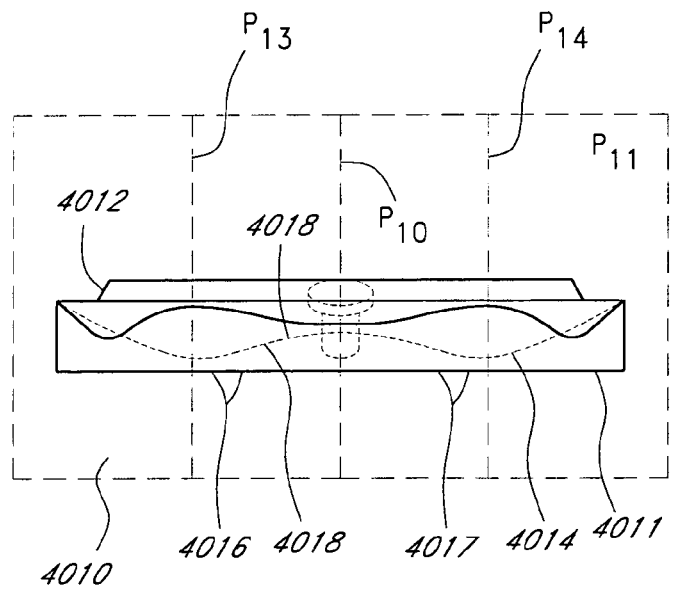
FIG. 67B is a rear or posterior elevation view of the second portion of FIG. 67A.
Figure 67C:
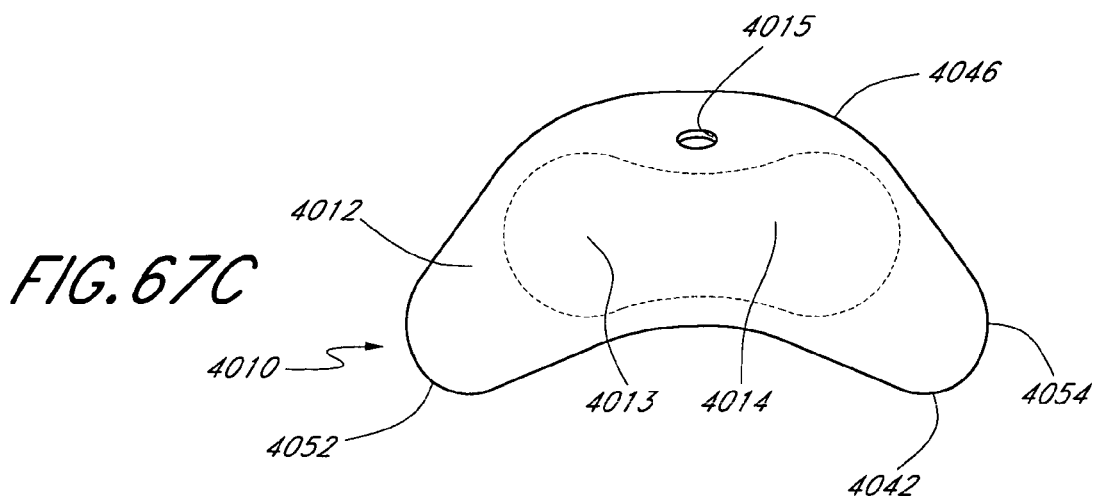
FIG. 67C is a top or superior plan view of the second portion of FIG. 67A.
Figure 70A:
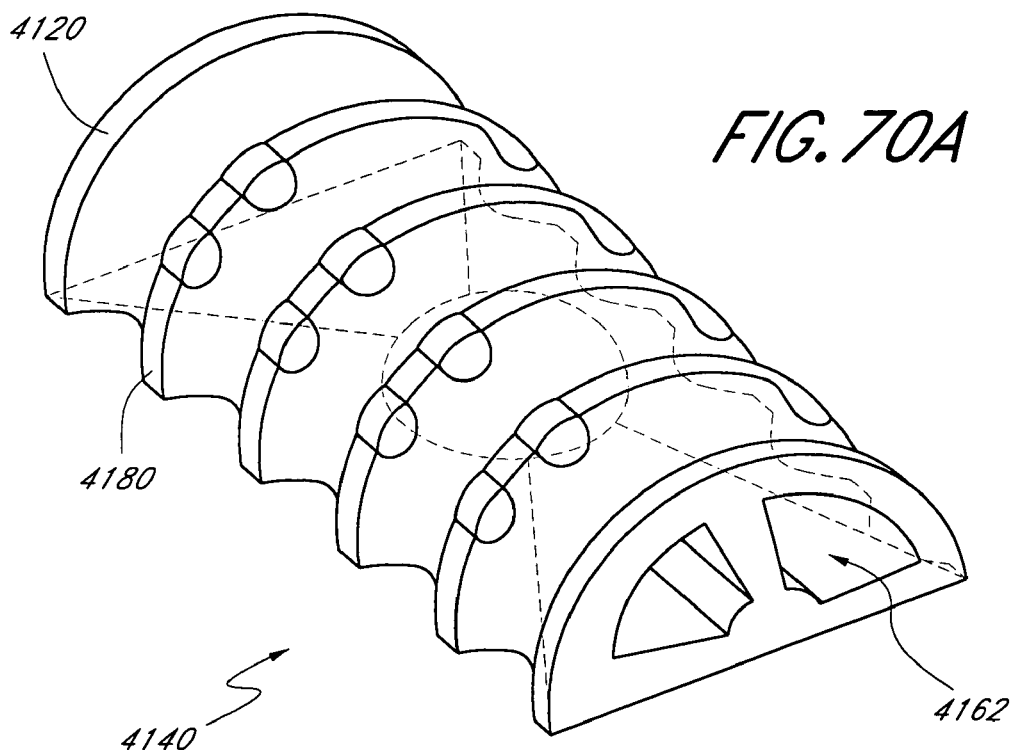
FIGS. 70A and 70B show a perspective view of another embodiment of a spinal implant having a cylindrical form.
Figure 70B:
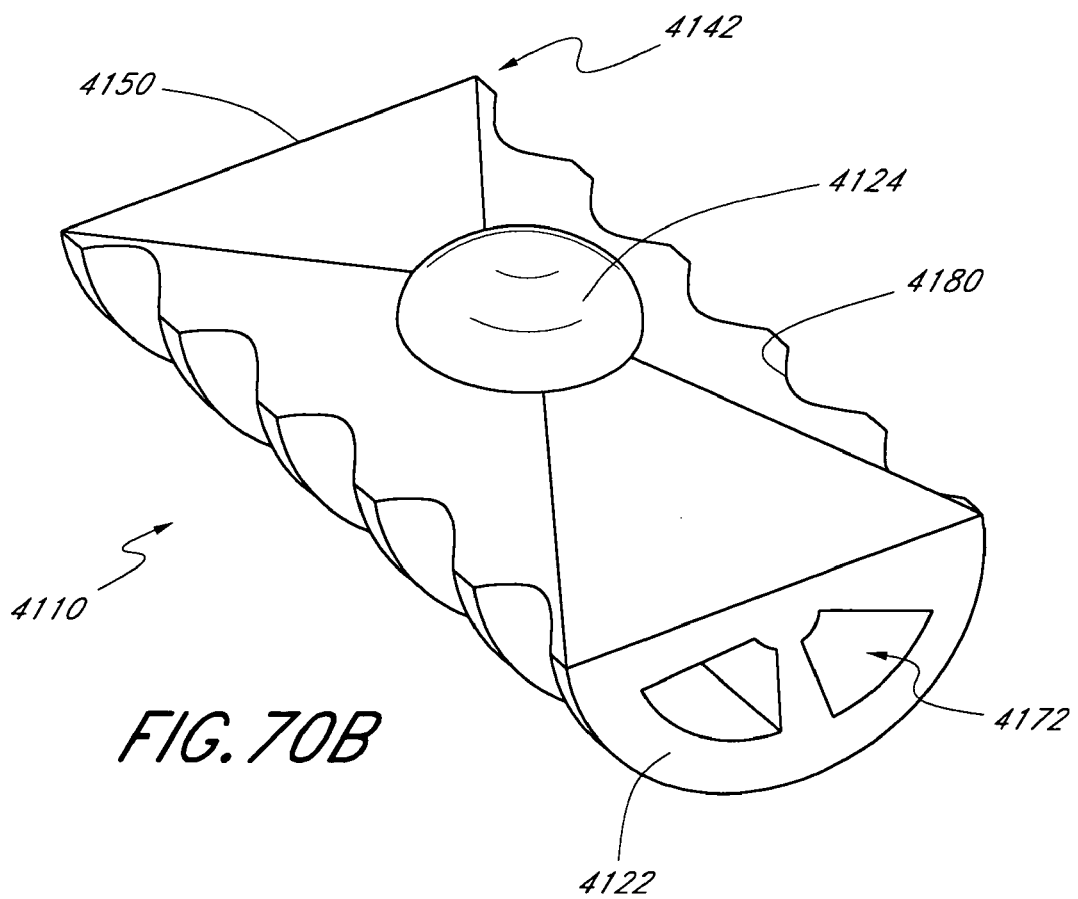

Distal end portion 3210 allows the apparatus to provide simultaneous shielding of both the dura D and the nerve root R. In FIGS. 65A-65B, surface 3242 shields the dura D, and surface 3240 shields the nerve root R. It is understood that surfaces 3240 and 3242 may be interchanged with respect to which tissue they protect during the surgical procedure.

According to the exemplifying embodiment, once the fusion and fixation portions of the procedure have been performed, the procedure is substantially complete. The surgical instrumentation, such as the endoscope 500 can be withdrawn from the surgical site. The access device 20 is also withdrawn from the site. The muscle and fascia typically close as the access device 20 is withdrawn through the dilated tissues in the reduced profile configuration. The fascia and skin incisions are closed in the typical manner, with sutures, etc. The procedure described above may be repeated for the other lateral side of the same vertebrae, if indicated.

II. Apparatuses and Methods for Replacing a Spinal Disc and Preserving Motion

Another type of procedure that can be performed by way of the systems and apparatuses described herein involves replacement of one or more of a patient's spinal discs with an implant, e.g., a prosthetic device, that provides the functions of the spinal disc while preserving or restoring a degree of normal motion after recovery. Such a procedure may be applied to a patient suffering degenerative disc disease or otherwise suffering from disc degeneration. A variety of motion preserving implants that may be applied to replace a damaged or degenerating disc are described below. The access devices and systems described herein enable these devices and methods associated therewith to be practiced minimally invasively.

A. Spinal Implant with Articulation Similar to the Knee

A first type of spinal implant configured to preserve or restore a degree of normal motion after recovery is shown in FIGS. 66A-69B. The first type is characterized by articulating in a manner similar to that of a human knee.

FIGS. 66A-66C and 67A-67C show a first portion 4001 and a second portion 4010 of the implant respectively. In one embodiment, the implant is a kidney-shaped device, as viewed from a top plan view. The implant includes the first portion 4001 and the second portion 4010, both of which are kidney-shaped in one embodiment. The implant may be placed between adjacent vertebrae in a manner similar to the placement of the implant 2110, shown in FIG. 50. Each of the first portion 4001 and second portion 4010 has an anterior end 4040, 4042, an opposing posterior end 4044, 4046, and two lateral sides 4048, 4050 and 4052, 4054.

The first portion and the second portion articulate with one another to form an artificial disc that operates in a manner similar to a human knee, e.g., as a knee-type joint, that permits limited rotation of the first portion 4001 with respect to the second portion 4010 about a vertical axis $X_1$. The range of rotation permitted preferably is about 10 degree, e.g., +/−5 degrees off center in either direction. The implant preferably produces a moderate degree of restraint to permit over-rotation.

The first portion 4001 further comprises a substantially planar, or flat, first superior surface 4002 and an opposing contoured or articulating first inferior surface 4003 comprising two laterally juxtaposed convex portions 4004, 4005 of substantially the same shape. The second portion 4010 further comprises a substantially planar, or flat, second inferior surface 4011 and an opposing contoured or articulating second superior surface 4012 comprising two laterally juxtaposed concave portions 4013, 4014 which are larger in size than the respective convex portions of the first portion 4001.

The first and second portions 4001, 4010 can be described by the frontal (or transverse) and median (or sagittal) sections of their respective articulating surfaces. The articulating first inferior surface 4003 of the first portion 4001 has a sagittal section, in the anterior to posterior direction along plane $P_1$, resembling an outwardly curved arch, e.g., convex, having a varying radius of curvature. The condyles 4004, 4005 can each have a sagittal section, along the midpoint of each condyle (see the planes $P_4$ and $P_5$, respectively), resembling a curve comprising at least a portion having a varying radius of curvature. In one embodiment, the shape of the curve in the sagittal section will approximate the shape of a curve described by a Fibonacci mathematical series.

The condyles 4004, 4005 can have a combined transverse section, in a lateral to lateral direction along plane $P_2$, resembling a bimodal outwardly curved arch, e.g., two convex curves, having a varying radius of curvature. The plane $P_2$ is disposed approximately half way between the anterior end 4040 and the posterior end 4044. The condyles 4004, 4005 can each have an individual transverse section, along the plane $P_2$, resembling a curve comprising at least a portion having a varying radius of curvature. In a preferred embodiment, the shape of the curve of the transverse section for each condyle 4004, 4005 will approximate the shape of a curve described by a Fibonacci mathematical series.

The articulating second superior surface 4012 of the second portion 4010 has a sagittal section, in an anterior to posterior direction along plane $P_{10}$, resembling an inwardly curved arch, e.g., concave, having a varying radius of curvature. The modes 4013, 4014 can each have a sagittal section, along the midpoint of each mode (see the planes $P_{13}$ and $P_{14}$, respectively), resembling a curve comprising at least a portion having a varying radius of curvature. In a preferred embodiment, the shape of the concave curves in the sagittal section will approximate the shape of a curve described by a Fibonacci mathematical series.

The concave modes 4013, 4014 can have a combined transverse section, in a lateral to lateral direction along plane $P_{11}$, resembling a bimodal inwardly curved arch, e.g. two concave curves. The plane $P_{11}$ is disposed approximately half way between the anterior end 4042 and the posterior end 4046. The concave modes 4013, 4014 can each have an individual transverse section, along plane $P_{11}$, resembling a curve comprising at least a portion having a varying radius of curvature. In a preferred embodiment, the shape of the curve of the transverse section for each concave mode 4013, 4014 will approximate the shape of a curve described by a Fibonacci mathematical series.

The respective shapes of the concave and convex portions of the articulating surfaces 4003, 4012, respectively, will comprise portions that are substantially complementary; however, the articulating surfaces will be shaped to permit articulation of the first and second portions 4001, 4010 in a manner resembling the articulation of a human knee. Thus, the articulating surfaces 4003, 4012 can be regularly or irregularly shaped as at least partially complementary portions of spheroids, paraboloids, hyperboloids or ellipsoids of revolution or combinations thereof As discussed above, the concave and convex portions of the articulating surfaces can be described by both coronal, i.e., transverse, and sagittal arcs which are variable, i.e., have varying radii of curvature, and allow for changing instant centers of rotation and moderate degrees of rotation during articulation of the surfaces 4003, 4012.

The articulating surfaces 4003 and 4012 are designed so that the respective concave and convex portions thereof comprise a major portion of substantially the entirety of the respective articulating surfaces 4003 and 4012. Thus, while the articulating surfaces are surrounded by respective surfaces defining the outer periphery of each of the respective portions 4001 and 4010, the articulating surfaces 4003 and 4012 do not have respective inferior and superior surface portions that completely surround the articulating respective portions of said surfaces. For example, substantially all of the convex-shaped portions 4004, 4005 of the articulating surface 4003 can articulate with substantially all of the cave-shaped portions 4013, 4014 of the articulating surface 4012.

FIGS. 68A and 68B depict one embodiment of a spinal implant 4020 that includes a superior first portion 4021 and an inferior second portion 4022. The first portion 4021 includes a first articular surface 4025 which articulates with a second articular surface 4026 of the second portion 4022. FIG. 68A is a side elevation view of the implant 4020 and it corresponds to a lateral view thereof. As the first and second portion 4021, 4022 articulate along their articulating surfaces 4025 and 4026, respectively, the first portion 4021 will move in the direction indicated by the arrow (B) from the home position depicted in FIG. 68A to a second position depicted in FIG. 68B. In the home position, the first and second portions 4021, 4022 share a common center of rotation 4023a, 4023b. However, when the first portion 4021 is articulated to a second position as depicted in FIG. 68B, the instant centers of rotation 4023a, 4023b are no longer coincident. Therefore, when a patient using this embodiment bends in a forward or backward manner, i.e., flexes in an anteroposterior fashion, the instant centers of rotation 4023a, 4023b will be displaced away from each other in an anteroposterior fashion, i.e., there will be an anteroposterior translation of the instant center of rotation 4023b with respect to the instant center of rotation 4023a.

FIGS. 69A and 69B depict partial cross-sectional rear, or posterior, elevation views of another embodiment of an spinal implant 4030 comprising a first superior portion 4031 and a second inferior portion 4032. The first superior portion 4031 comprises a bicondylar articulating surface which articulates with a bimodal concave articulating surface 4034 of the second portion 4032. The first and second portions 4031, 4032 are depicted in a home or neutral position. When the first portion 4031 is translated laterally along the arrow (T) with respect to the second portion 4032, the first portion 4031 will tilt slightly with respect to the second portion 4032 and the instant centers of rotation 4035a, 4035b will be displaced from one another. Therefore, in one embodiment, the spinal implant will comprise first and second articulating surfaces which are adapted to provide a changing center of rotation when the articulating surfaces are translated or articulated with respect to one another in a lateral-to-lateral fashion.

Although not shown, in one embodiment, one or both of the first and second portions of any of the implants 4020, 4030 may include fasteners to facilitate their attachment to adjacent vertebrae. These fasteners may comprise one or more projections on one of the generally planar surfaces of the first and/or second portions. In one embodiment, two projections are provided that mate with corresponding cavities in adjacent vertebrae. Alternatively or additionally, multiple screw holes may be disposed in the first or second portions 4001, 4010 through which cancellous screws may be inserted and screwed into the adjacent vertebra. The fasteners may comprise other known means for providing attachment to a selected portion of the vertebra, including screws, nails, hooks, rivets, adhesives, wires, bands and straps. In one embodiment, the planar surfaces 4002, 4011 can further comprise porous coatings to enhance ossification thereof, such as by promoting the ingrowth of bone.

Further details of the first type of implant may be found in U.S. Pat. No. 6,039,763, issued Mar. 21, 2000, which is hereby incorporated by reference in its entirety.

Further details of similar structures that replace spinal discs with prosthetic devices may be found in U.S. Pat. No. 5,314,477, issued May 24, 1994, U.S. Pat. No. 5,562,738, issued Oct. 8, 1996, U.S. Pat. No. 5,676,701, issued Oct. 14, 1997, U.S. Pat. No. 5,782,832, issued Jul. 21, 1998, U.S. Pat. No. 6,156,067, issued Dec. 5, 2000, U.S. Pat. No. 6,540,785, issued Apr. 1, 2003, and U.S. Pat. No. 6,039,763 assigned to Disc Replacement Technologies, Inc., which are hereby incorporated by reference in their entirety.

B. Spinal Implant with an Internal Pivot

FIGS. 70A-72 show another embodiment of an implant 4110 configured to preserve or restore a degree of normal motion after recovery. The implant 4110 comprises a first element 4120 and a second element 4122. The first element 4120 is coupled to the second element 4122 by an internal pivot 4124 or other suitable means for allowing internal articulation, or relative pivotal movement between the first and second elements 4120, 4122.

The first element 4120 of the implant 4110 comprises a first fusion chamber 4130, for engaging a first vertebra, e.g., a vertebra located directly superiorly of the first fusion chamber 4130. At least one opening 4132 is formed in the first fusion chamber 4130, to facilitate bone growth into, through, and around the first fusion chamber 4130 from the first vertebra, to fuse the first element to the first vertebra. Preferably, a plurality of openings 4132 are provided to further promote bone ingrowth. Fusion by bone ingrowth provides a generally rigid connection between the implant 4110 and the skeletal structure. Other connection means known in the art could be provided in other embodiments.

Similarly, the second element 4122 of the implant 4110 comprises a second fusion chamber 4134, substantially similar in construction to the above-described first fusion chamber 4130, and comprising at least one opening 4136 formed therein for facilitating bone growth into, through and around the second fusion chamber 4134 from a second vertebra located directly inferiorly of the second element 4122. Other second connection means may also be provided, as desired, e.g., an adhesive connection, screw connection, pin connection, or any other effective alternative connection means. The second fusion chamber 4134 provides a permanent and secure coupling, as discussed above. The first and second elements 4120, 4122 can be fabricated from biocompatible materials including, without limitation, titanium, surgical alloys, stainless steel, chrome-molybdenum alloy, cobalt chromium alloy, zirconium oxide ceramic, nonabsorbable polymers and other anticipated biocompatible metallic or polymeric materials.

The internal pivot 4124 of the present invention preferably comprises a first articulation surface 4140 provided on the first element 4120, and an abutting second articulation surface 4142 provided on the second element 4122. The first and second articulation surfaces 4140, 4142 preferably are fabricated from or coated with low-friction, wear and impact-resistant, biocompatible materials, such as, for example, titanium, stainless steel, surgical alloys, chrome molybdenum alloys, cobalt chromium alloy, zirconium oxide ceramic, nonabsorbable polymers and other biocompatible metallic or polymeric materials. The internal pivot 4124 resists axial compression between the first and second elements 4120, 4122, but allows relative pivotal movement therebetween. Thus, when implanted, the internal pivot 4124 resists axial compression between first and second vertebra along a support axis extending generally along the spinal column, but permits pivotal movement between vertebrae. The term "pivotal," is intended to comprehend either or both of a rotational or twisting motion about the support axis (for example, rotation between cervical vertebrae by turning the head to the right or left), and/or a tilting motion angularly inclined in any direction relative to the support axis (for example, nodding the head forward or backward and/or tilting the head downward to the right or left).

Axial compression, as well as lateral translation normal to the support axis, is resisted between the first and second vertebra by providing the first internal articulation surface 4140 with a void, such as a concave surface 4146, which receives a protuberance, such as a convex surface 4148, projecting from the second internal articulation surface 4142, e.g., like a "ball-and-socket" arrangement. This arrangement allows relative rotation about the support axis between the first and second vertebra. The internal pivot 4124 can be provided with one or more stops to limit the range of rotational movement allowed.

The internal pivot 4124 preferably further comprises one or more angularly offset bevels 4150 formed in the first internal articulation surface 4140 and/or the second internal articulation surface 4142, to allow relative tilting movement in one or more directions between the adjacent vertebrae defining the interbody space into which the implant 4110 is implanted. In the illustrated embodiment, the first and second internal articulation surfaces 4140, 4142 are each provided with an angularly offset bevel 4150, in a generally pyramidal configuration, thereby enabling tilting movement in all directions (360 degrees). A generally conical configuration is also possible and, likewise, would permit both rotational movement and 360 degree tilting movement.

The natural range of motion of the spine may be approximated by providing bevels 4150 of approximately 5 degrees around the periphery of each of the first and second articulation surfaces 4140, 4142, thereby allowing approximately 10 degrees of tilt in all directions between adjacent vertebrae. The pivot point or axis of the internal pivot 4124 is generally centrally located on the first and second articulation surfaces 4140, 4142, and may be aligned with the spine's normal axis of rotation when implanted. This location, however, can be selectively varied to position the center of rotation of the internal pivot 4124 centrally, anteriorly, posteriorly, to the left, to the right, or eccentrically (off-center in both the anterior/posterior direction and the left/right direction) of the spine's normal axis of rotation, in order to achieve proper alignment of the spine, thereby restoring optimal sagittal and coronal spinal balance and alignment.

In one embodiment, the first and second elements 4120, 4122 of the implant 4110 preferably comprise generally hemicylindrical outer walls 4160, 4170 adjoining to form a generally cylindrical body. When in their assembled configuration, the first element 4120 and the second element 4122 abut one another with their respective first and second articulating surfaces 4140, 4142 adjacent and engaging one another, as described above. The first element 4120 preferably further comprises a first radiused outer wall 4160. The one or more openings 4132 for facilitating bone ingrowth are provided in this first radiused outer wall 4160, and communicate with a first fusion chamber 4162 formed between the first radiused outer wall 4160 and the first articulating surface 4140. Similarly, the second element 4122 preferably comprises a second radiused outer wall 4170, defining one or more openings 4136 for facilitating bone ingrowth. The openings 4136 communicate with a second fusion chamber 4172 formed between the second radiused outer wall 4170 and the second articulating surface 4134. The first and second radiused outer walls 4160, 4170 can be provided with threads 4180 to facilitate advancing the implant 4110 into the interbody space during implantation and to help secure the implant 4110 in position once implanted. The threads 4180 on each of the first and second radiused outer walls 4160, 4170 are preferably aligned to form continuous threads when the first and second elements 4120, 4122 are engaged. In some instances, it may be desirable to provide self-tapping threads 4180, and/or to configure the threads 80 to direct bone fragment generated by implantation into the openings 4132. In other embodiments, the threads 80 are replaced with a contoured outer surface comprising smooth, splined, flanged, spiked or beaded surface features. The implant 4110 can further comprise one or more support flanges 4185 in the first and/or second elements 4120, 4122, for additional strength.

Figure 72:
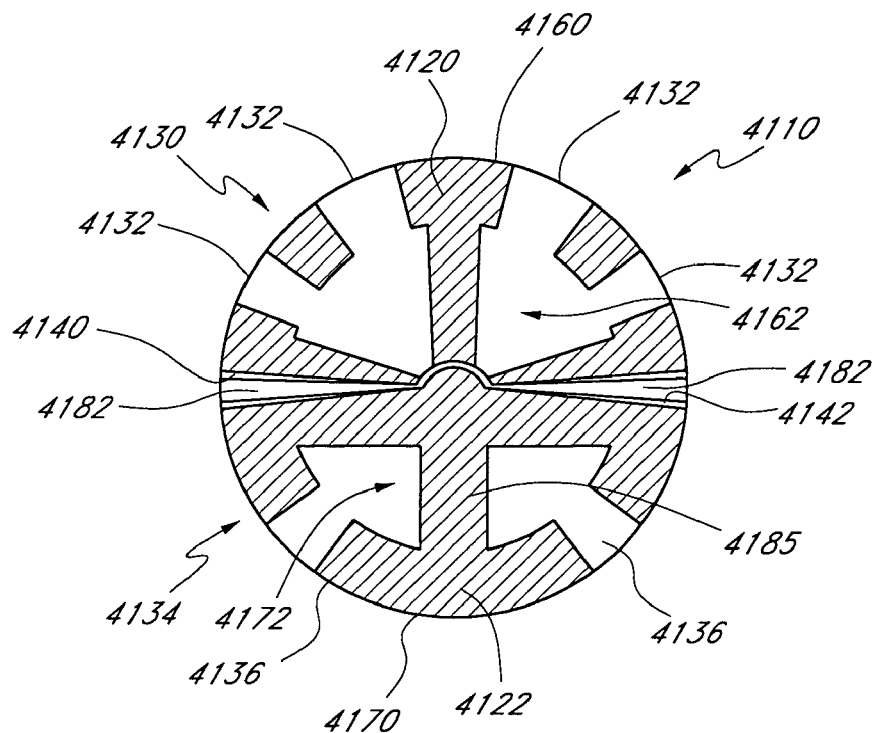
FIG. 72 is a cross-sectional end view of the spinal implant of FIGS. 70A and 70B.

The implant 4110 may further comprise one or more structures to temporarily rigidly coupling the first element 4120 to the second element 41.22 to prevent relative movement therebetween. For example, it is preferred that the first and second elements 4120, 4122 be held rigidly in place during installation of the implant 4110 into the interbody space. In addition, the first and second elements 4120, 4122 should remain rigidly coupled for a sufficient length of time after implantation to permit sufficient bone ingrowth into the fusion chambers to prevent relative motion between the implant 4110 and the vertebrae during normal activities of the patient. This temporary stabilization of the first and second elements is accomplished without the requirement of a second surgical procedure through the use of medium-term structures formed from bioreabsorbable material. Examples of bioreabsorbable materials include polyglycolate polymers or analogues, lactides, polydioxanone, polyglyconate, lactide/glycolide copolymers. By appropriate selection of the material(s) of construction, the length of time required to biodegrade the stabilizing means can be effectively controlled. After the stabilizing means are dissolved and absorbed by the body, the first and second elements of the implant 4110 are uncoupled, allowing articulation. FIG. 72 shows one structure that includes one or more biodegradable shims 4182 wedged between the first element 4120 and the second element 4122, to prevent relative motion therebetween.

Figure 71:
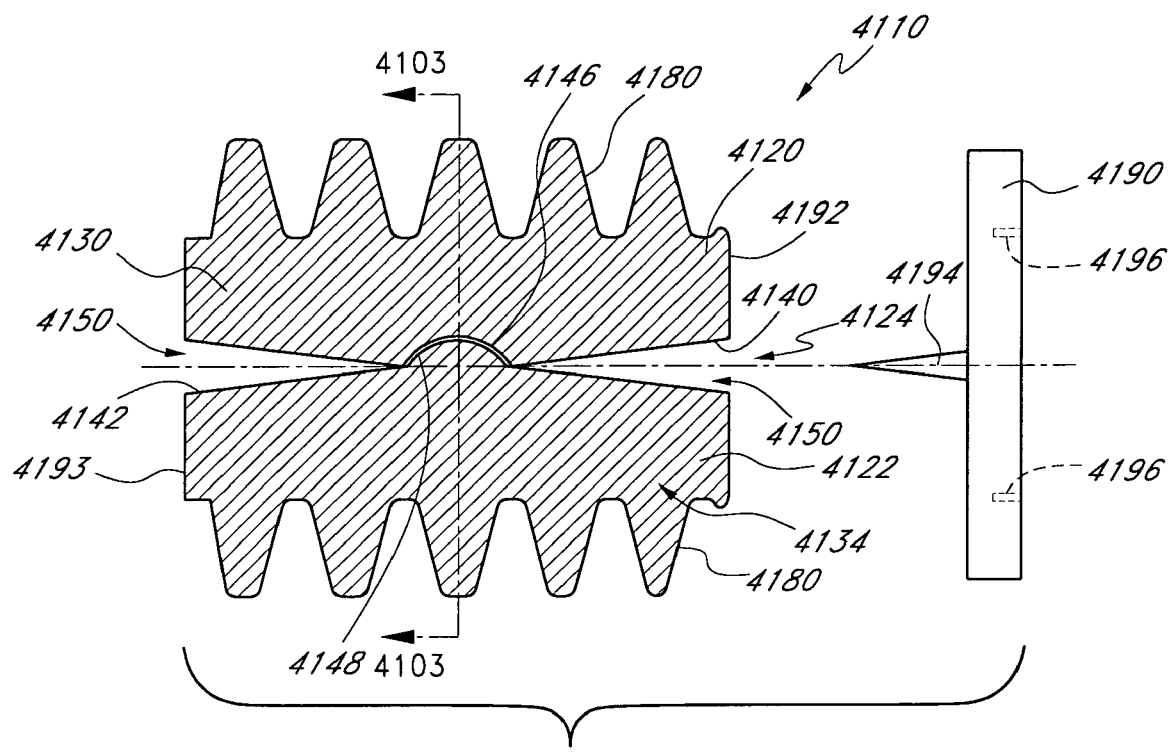
FIG. 71 is a cross-sectional side view of the spinal implant of FIGS. 70A and 70B.

In another example embodiment, the first and second elements 4120, 4122 are placed in their coupled configuration, as shown in FIGS. 71-72, with the spaces between the articulating surfaces 4140, 4142 then being injected or filled with a biodegradable polymer, which provides the medium term temporary stabilizing means to couple the elements in position. Care will be taken to avoid filling the fusion chambers 4130, 4134 and the openings 4132, 4136 to the fusion chambers with the polymer, which could inhibit bone ingrowth. The threads 4180 will also remain exposed to assist in implantation of the device.

FIG. 71 shows a removable and/or bioreabsorbable endcap 4190, which releasably engages a tailing end 4192 of the implant 4110 to couple the first and second elements 4120, 4122. The endcap 4190 can comprise one or more clips 4194 for engaging the implant 4110, and one or more keyways 4196 for engaging a wrench, driver or other actuation device used to advance the implant 4110 into the intervertebral space. A second removable and/or absorbable endcap can be installed on the leading end 4193 of the implant 4110. The endcaps may additionally function to retain the bone fragments within the chambers 4162, 4172 of the fusion chambers 4130, 4134.

Further details of the second type of motion preserving or restoring implant may be found in U.S. Pat. No. 6,440,168, issued Aug. 27, 2002, which is hereby incorporated by reference in its entirety.

Further details of implants that function similarly to implant 4110 may be found in U.S. Pat. No. 6,419,706, issued Jul. 16, 2002, which is hereby incorporated by reference in its entirety.

C. Spinal Implant Arranged for Adequate Deformation

Figure 73:
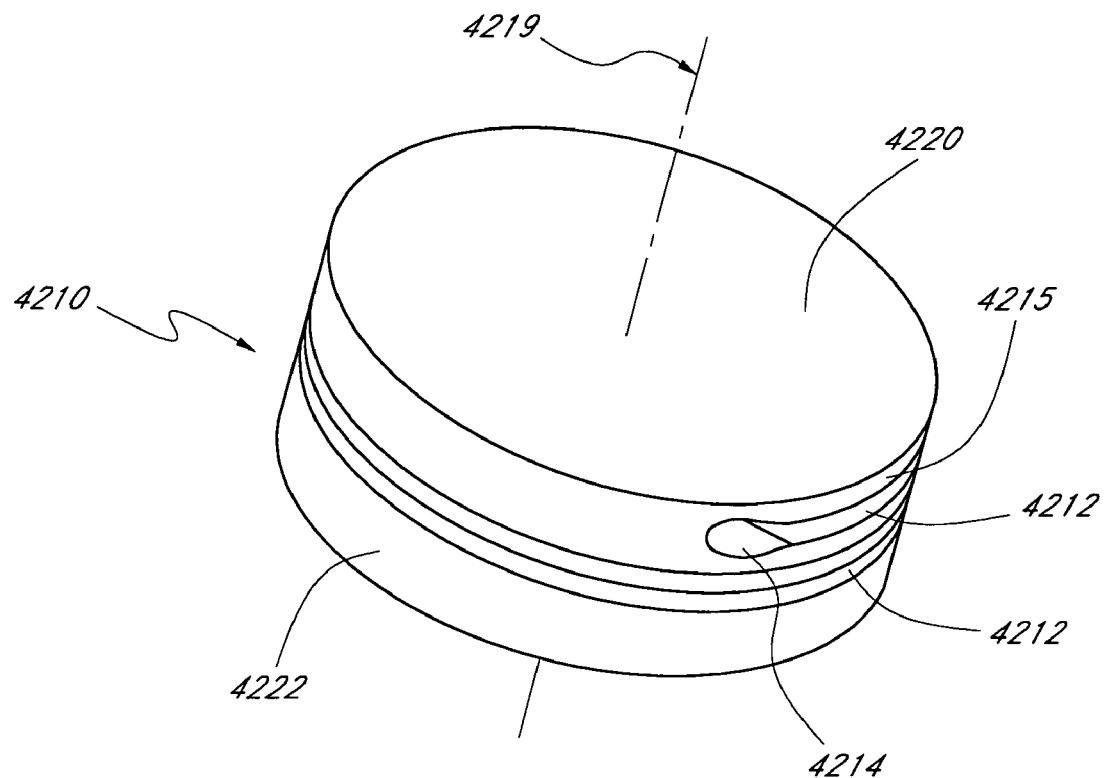
FIG. 73 is a plan view of another embodiment of a spinal implant.

FIG. 73 shows another type of implant configured to preserve or restore a degree of normal motion after recovery. In particular, an implant 4210 includes a plurality of slits 4212 defined in the perimeter surface 4215. The slits 4212 specifically weaken the implant 4210 to enable the implant 4210 to deform as needed. The slits 4212 preferably terminate in perimeter openings 4214, which are larger than the slit thickness. The dimension of the slits 4212, e.g., their placement and anterior-posterior depths and thickness, may be varied. Varying the dimensions or numbers of slits 4212 changes the flexibility of the implant 4210.

FIG. 73 shows that the slits 4212 are substantially at a right angle to an axis (4219) of the implant 4210. In other embodiments a slit may be defined on the perimeter surface 4215 transverse to the axis. However, since the upper and lower surfaces of the implant 4210 do not have to be parallel, the slits 4212 do not have to be parallel with respect to the upper and lower surfaces or with respect to other slits. The number, thickness and depth of the slits may be varied to achieve the level of flexibility desired for the disc prosthesis. Thicker, deeper, or a greater number of slits will increase flexibility. The upper surface and the lower surface of the implant 4210 are shown as being substantially flat. However, there are many surface types that could be used, e.g., surfaces configured to foster bone ingrowth. Preferably, the implant comprises a coating on at least one surface to promote bone ingrowth. This coating may includes ceramic beads, wire meshes, and other types of ceramics.

The slits 4212 preferably terminate at perimeter openings 4214, or holes. The dimensions of the perimeter openings 4214 may be varied to reduce stress and to change the flexibility of the implant. The geometry of the perimeter openings can be circular or non-circular. The perimeter openings are circular in one embodiment.

Further details of structures that replace spinal discs with prosthetic devices may be found in U.S. Pat. No. 6,579,321, issued Jun. 17, 2003, which is hereby incorporated by reference in its entirety.

Further details of implants that function similarly to implant 4210 may be found in U.S. Pat. No. 6,315,797, issued Nov. 13, 2001, which is hereby incorporated by reference in its entirety.

Figure 74:
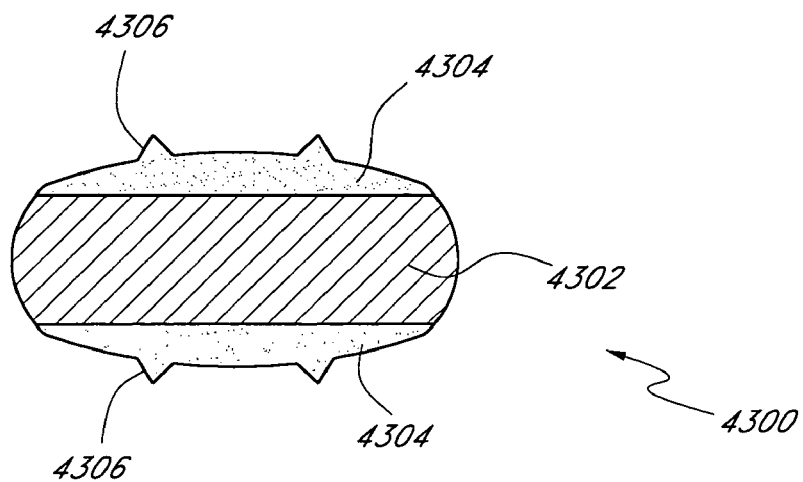
FIG. 74 is a plan view of another embodiment of a spinal implant.

D. Spinal Implant with a Bone Growth Promoting End Plate and a Cushioning Member FIG. 74 is a side view of one embodiment of another type of spinal implant 4300. The implant 4300 includes a cushioning member 4302 that is disposed between a pair of endplates 4304. In one embodiment, a plurality of protrusions 4306, e.g., spikes, extend from at least one of the endplates 4304 to help hold the implant 4300 in the interbody space between the adjacent vertebrae. The cushioning member 4302 is configured to cyclically compress and expand in a manner similar to the disc material being replaced and is composed of a suitable material, e.g., polymeric urethane or other suitable elastomers, or other filling material to impart an appropriate level of compressibility. The superior and inferior surfaces of the end plates 4304 may be convex, and may further include grooves, spikes, or other protrusions to maintain the body within the interbody space, as discussed above. The implant 4300 also may be wedge-shaped to help restore or maintain lordosis, particularly if the prosthesis is introduced into the cervical or lumbar regions of the spine. The endplates 4304 of the implant 4300 preferably are formed of metal and/or otherwise provide bone-ingrowth surfaces. Further details of the implant 4300 may be found in U.S. patent application Publication No. US 2003/0074076, published Apr. 17, 2003, which is the publication of U.S. application Ser. No. 10/303,385, filed Nov. 25, 2002, which is hereby incorporated by reference in its entirety.

Further details of implants that function similarly to implant 4300 may be found in U.S. Pat. No. 4,911,718, issued Mar. 27, 1990, U.S. Pat. No. 4,932,969, issued Jun. 12, 1990, U.S. Pat. No. 5,370,697, issued Dec. 6, 1994, U.S. Pat. No. 5,556,431, issued Sep. 17, 1996, U.S. Pat. No. 6,348,071, issued Feb. 19, 2002, U.S. Pat. No. 6,368,350, issued Apr. 9, 2002, U.S. Pat. No. 6,582,466, issued Jun. 24, 2003, U.S. Pat. No. 6,592,624, issued Jul. 15, 2003, and U.S. patent application Publication No. US 2002/0082701, published Jun. 27, 2002, which is the publication of U.S. application Ser. No. 10/085872, filed Feb. 28, 2002, which are hereby incorporated by reference in their entirety.

E. Motion Preserving Spinal Implant

Figure 75:
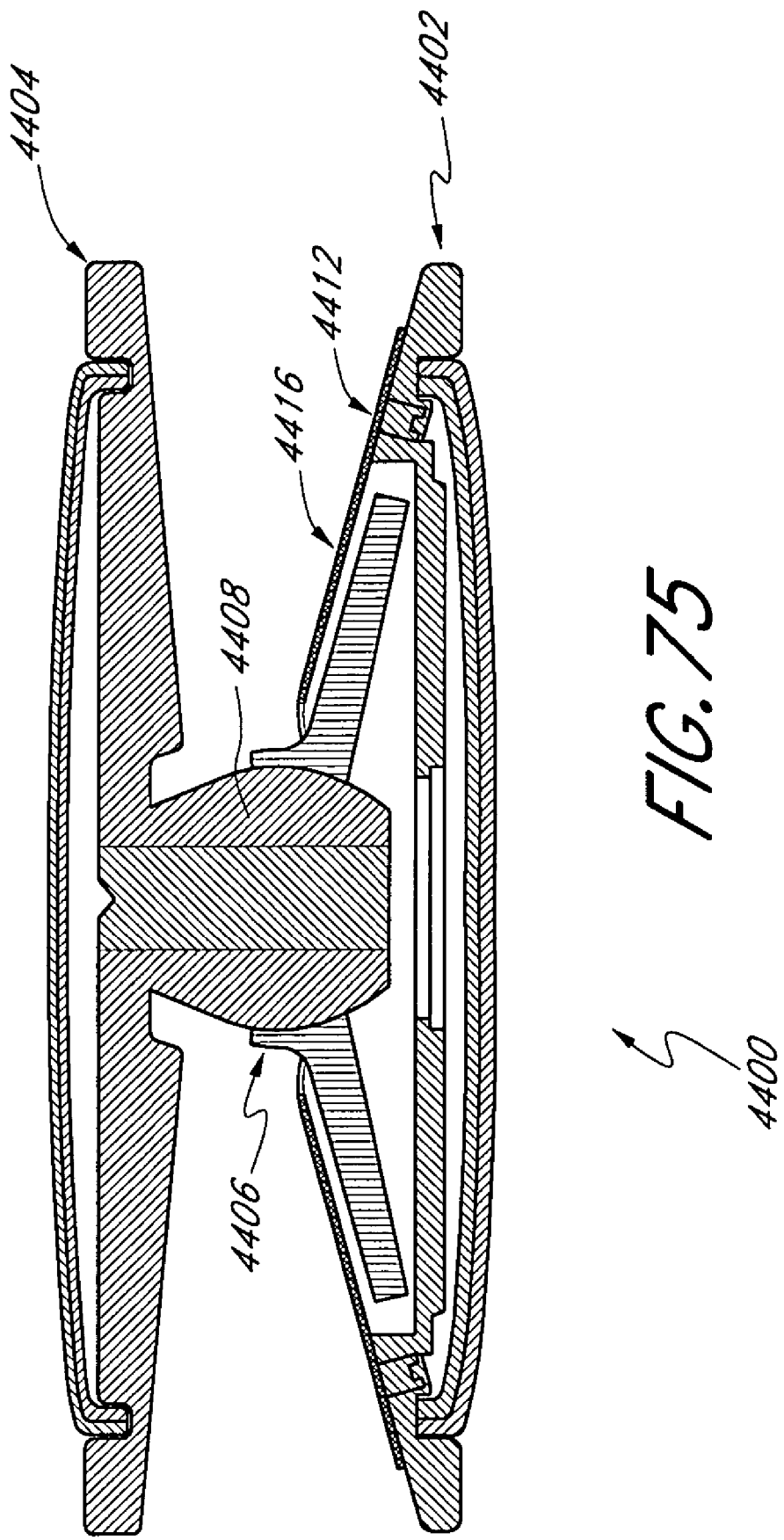
FIG. 75 is a plan view of another embodiment of a spinal implant.

Another type of spinal implant that can be delivered by way of the access device 20 and which is configured to preserve or restore a degree of motion. FIG. 75 shows a spinal implant 4400 that has a pair of opposing members 4402, 4404 for seating against opposing vertebral bone surfaces. The members 4402, 4404 are separated by a spring mechanism. In one embodiment, the spring mechanism includes at least one spirally slotted belleville washer 4406 having radially extending grooves. One of the members 4402, 4404 has a centrally located ball-shaped protrusion 4408 that is rotatably coupled in a central socket in the narrow end of the belleville washer 4406. The wide end of the belleville washer 4406 is held against the member 4402 by a shield 4410 with rivets 4412. This arrangement prevents the implant 4400 from becoming disassembled under tension loads applied to the members 4402, 4404. The location of the ball joint provides the implant 4400 with a centroid of motion that is centrally located between the vertebral bone surfaces when applied. Thus, the implant 4400 behaves similarly to a healthy natural intervertebral disc.

Further details of other embodiments related to the implant 4400 are disclosed in U.S. patent application Publication No. 2003/0069643, published Apr. 10, 2003, which is the publication of U.S. application Ser. No. 10/151,280, filed on May 20, 2002 and U.S. patent application Publication No. 2003/0078667, published Jul. 15, 2003, which is the publication of U.S. application Ser. No. 10/324,200, filed Dec. 20, 2002, which are hereby incorporated by reference in their entirety.

F. Further Methods of Applying an Interbody Implant

FIGS. 76-79 more particularly illustrate methods whereby an implant 4500 is delivered through an access device 4504 and implanted in an interbody space I defined between a first vertebra $V_1$ and a second vertebra $V_2$. The implant 4500 may be any suitable implant, e.g., any of the implants 4020, 4030, 4110, 4210, 4300, 4400. Some methods of implanting the implant 4500 may be similar to the methods of implanting the fusion implant 2010 described above in connection with FIG. 51.

In one method, access to the interbody space I is provided by inserting the access device 4504 into the patient. The access device 4504 may be configured in a manner similar to the expandable conduit 20 and may be inserted in a similar manner, e.g., over a dilator. The access device 4504 preferably has an elongate body 4508 that has a proximal end 4512 and a distal end 4516. In one embodiment, the elongate body 4508 comprises a proximal portion 4520 and a distal portion 4524. The proximal portion 4520 may have a generally oblong or oval shape (as shown in FIG. 76A), a generally circular shape (as shown in FIG. 76B), or any other suitable shape. The distal portion 4524 preferably is expandable, as discussed above in connection with the expandable conduit 20, to the configuration illustrated in FIGS. 76, 77, and 78. At least one passage 4528 extends through the elongate body 4508 between the proximal end 4512 and the distal end 4516.

The elongate body 4508 has a length between the proximal end 4512 and the distal end 4516 that is selected such that when the access device 4504 is applied to a patient during a surgical procedure, the distal end 4516 can be positioned inside the patient adjacent a spinal location, and, when so applied, the proximal end 4512 preferably is located outside the patient at a suitable height. As discussed below, various methods can be performed through the access device 4504 by way of a variety of anatomical approaches, e.g., anterior, lateral, transforaminal, postero-lateral, and posterior approaches. The access device 4504 may be used for any of these approaches and may be particularly configured for any one of or for more than one of these approaches. For example, the access device 4504 may be generally lengthened for certain approaches, e.g., lateral and anterior, compared to other approaches, e.g., posterior and postero-lateral. The access device 4504 may be lengthened by lengthening the proximal portion 4520, the distal portion 4524, or the proximal and distal portions 4520, 4524.

Figure 78:
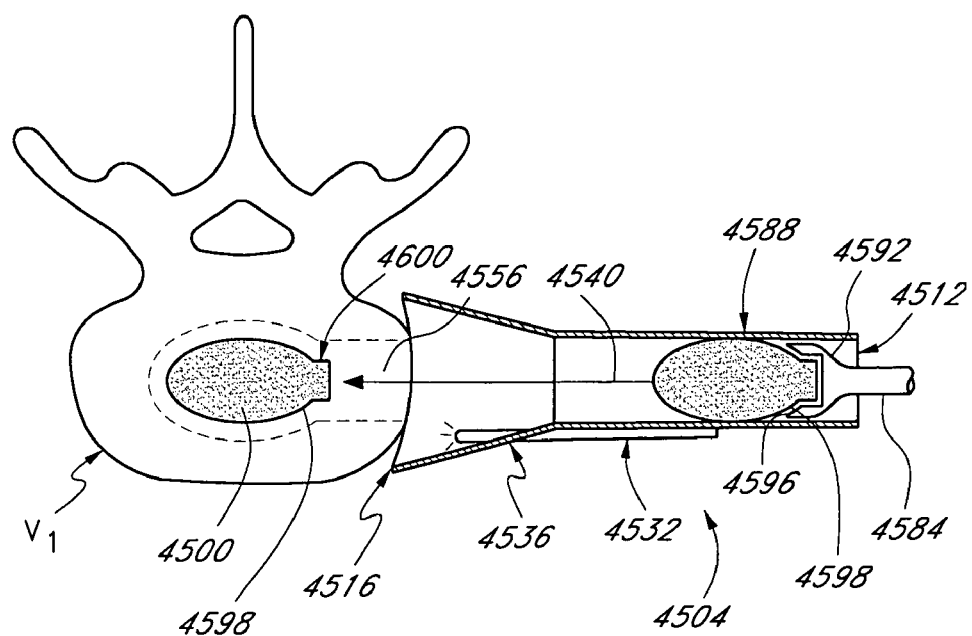
FIG. 78 is a schematic view similar to that of FIG. 76 illustrating one method of inserting a spinal implant into an interbody space through an access device.

FIG. 78 shows that the access device 4504 is configured to be coupled with a viewing element 4532 in one embodiment. The distal portion 4524 of the access device 4504 has an aperture 4536 into which the viewing element 4532 can be inserted, such that a proximal portion of the viewing element 4532 lies external to the proximal portion 4520 and a distal portion of the viewing element 4532 lies within the distal portion 4524 of the access device 4504. In another embodiment, the viewing element 4532 may extend within the access device 4504 substantially entirely the length of the passage 4528. In other embodiments, the viewing element 4532 may be moved to the surgical location entirely externally to the access device 4504. The viewing element 4532 may be configured to be removed from the access device 4504 during the procedure, as required.

The viewing element 4532 may be any suitable viewing element, such as an endoscope, a camera, loupes, a microscope, a lighting element, or a combination of the foregoing. The viewing element may be an endoscope, such as the endoscope 500, and a camera, which capture images to be displayed on a monitor, as discussed above. Further details of the access device 4504 are set forth in an application entitled MINIMALLY INVASIVE ACCESS DEVICE AND METHOD, filed Oct. 2, 2003, U.S. application Ser. No. 10/678,744, which is hereby incorporated by reference in its entirety.

Figure 77:
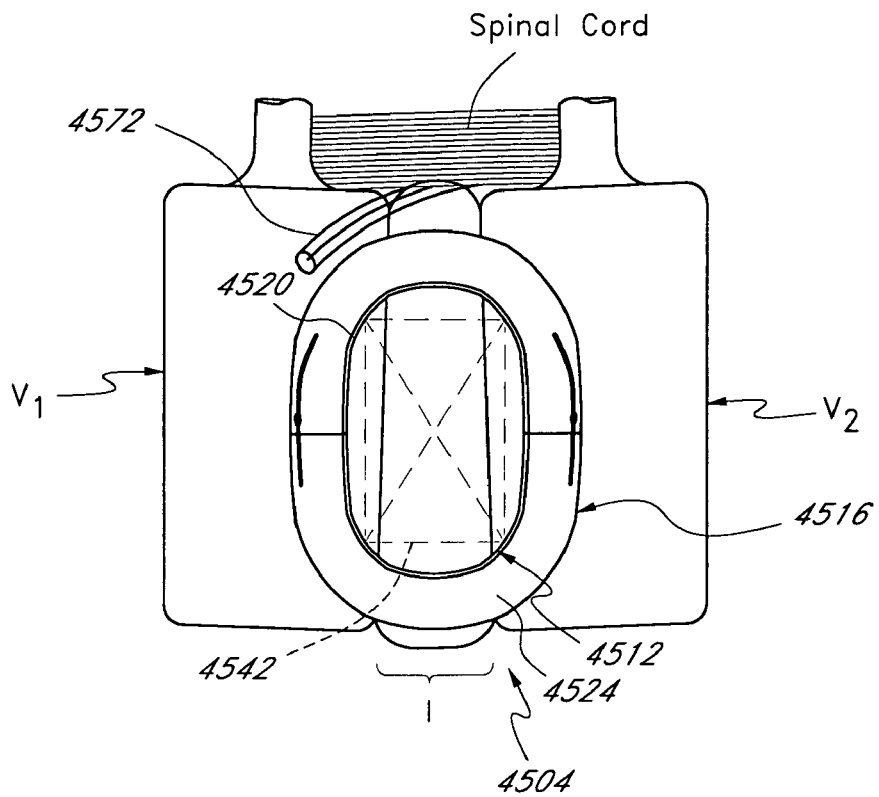
FIG. 77 is a schematic lateral view of a portion of a spine with the access device of FIG. 76B applied thereto to provide access to an interbody space.

In the illustrated methods, the distal end 4516 of the access device 4504 is inserted laterally, as indicated by an arrow 4540, to a surgical location adjacent to at least one vertebra and preferably adjacent to two vertebrae, e.g., the first vertebra $V_1$ and the second vertebra $V_2$, to provide access to at least a portion of the interbody space I. In another method, the access device 4504 is inserted postero-laterally, as indicated by an arrow 4544 and the dashed-line outline of the access device 4504 in FIG. 76, to provide access to at least a portion of the interbody space I. As discussed above, the access device 4504 can have a first configuration for insertion over the interbody space I and a second configuration wherein increased access is provided to the interbody space I. FIGS. 76 and 77 show that the second configuration may provide a cross-sectional area at the distal end 4516 that is larger than that of the first configuration at the distal end 4516. The distal portion 4524 of the access device 4504 may be expanded from the first configuration to the second configuration, as discussed above in connection with the skirt portion 24, using the expander apparatus 200. When so expanded, the distal portion 4524, at the distal end 4516, defines a surgical space 4542 that includes a portion of the interbody space I, e.g., a portion of the external surface of an annulus A.

As discussed above, in one embodiment, the access device 4504 has a substantially circular cross-sectional shape (as shown in FIG. 76B) in the proximal portion 4520. The access device 4504 may further have a circular cross-section near the proximal end 4512, near the distal end 4516, at the proximal and distal ends 4512, 4516, and from the proximal end 4512 to the distal end 4516. As discussed above, in another embodiment, the access device 4504 has an oblong cross-sectional shape (as shown in FIG. 76A) in the proximal portion 4520. In particular, the access device 4504 may have an oblong cross-section near the proximal end 4512, near the distal end 4516, at the proximal and distal ends 4512, 4516, and from the proximal end 4512 to the distal end 4516.

In some methods of applying the implant 4500, a second access device, such as an expandable conduit 20 or other suitable access device, may be inserted into the patient. For example, a second access device could be inserted through a lateral approach on the opposite side of the spine, as indicated by an arrow 4548, to provide access to at least a portion of an interbody space, e.g., the interbody space I. In another embodiment, a second access device could be inserted through a postero-lateral approach on the opposite side of the spine, as indicated by an arrow 4552, to provide access to at least a portion of an interbody space, e.g., the interbody space I. This second access device may provide access to the interbody space I at about the same time as the first access device 4504 or during a later or earlier portion of a procedure. In one method, the implant 4500 is inserted from both sides of the spine using first and second access devices.

In various applications, one or more implants 4500 may be delivered through one or more access devices, such as the access device 4504, from different directions. For example, a first implant 4500 could be delivered through a first access device from the approach indicated by the arrow 4540, and a second implant 4500 could be delivered through a second access device from the approach indicated by the arrow 4548. In another method, a first implant 4500 could be delivered through a first access device from the approach indicated by the arrow 4540, and a second implant 4500 could be delivered through a second access device from the approach indicated by the arrow 4552. In another method, a first portion of a first implant 4500, e.g., a portion to be coupled with the superior vertebra defining the interbody space I, could be delivered through a first access device from the approach indicated by the arrow 4540, and a second portion of the first implant 4500, e.g., a portion to be coupled with the inferior vertebra defining the interbody space I, could be delivered through a second access device from the approach indicated by the arrow 4548. Thus, any combination of single, multiple implants, or implant sub-components may be delivered through one or more access devices from any combination of one or more approaches, such as the approaches indicated by the arrows 4540, 4544, 4548, 4552, or any other suitable approach.

FIG. 77 shows a lateral view of a portion of a spine of a patient with the access device 4504 delivered thereto. In this figure, the patient's natural disc in the interbody space I has not yet been treated. The access device 4504 is shown in the expanded configuration wherein the perimeter of the distal end 4516 extends outwardly beyond a projection of the perimeter of the proximal end 4512. In one embodiment, the access device 4504 is configured so that when in the expanded configuration, the distal end 4516 does not extend beyond the locations of a nerve root 4572 or the spinal cord. The nerve root 4572 and the spinal cord are located outside the surgical space 4542 defined generally within the perimeter of the distal end 4516 in some embodiments, and therefore are shielded from any implement or implant delivered to the surgical location through the access device 4504. When in position, in addition to providing access to the interbody space I and the disc material therein, the distal portion 4524 may cover the nerve root 4572 and spinal cord and thereby protect the nerve root 4572 and spinal cord. It is understood that the term "cover" as used in this context refers to distal end 4516 of the access device 4504 being located between the surgical space 4542 and the nerve root 4572 or the spinal cord, or in contact with the nerve root 4572 or the spinal cord without applying significant force, e.g., tension or displacement force, to the nerve root 4572 or the spinal cord. The access device 4504 can provide the additional advantage of gently retracting the nerve root 4572 or other delicate anatomical structures where desirable. Gentle retraction of the nerve root 4572 may be desirable in connection with some approaches, e.g., the lateral approach.

As discussed above, in some methods, suitable procedures may be performed to prepare the interbody space I to receive an implant, e.g., the implant 4500. For example, degraded natural disc material may be removed in a suitable manner, e.g., a discectomy may be performed. Also, the surfaces of the vertebrae $V_1$, $V_2$ facing the interbody space I may be prepared as needed, e.g., the surfaces may be scraped or scored, and/or holes may be formed in the vertebrae $V_1$, $V_2$ to receive one or more features formed on a surface of the implant 4500. FIG. 77 shows a surgical space 4542 wherein an annulotomy and/or end plate removal may be performed through the access device 4504. Such procedures may necessitate the deployment of additional surgical tools through the access device 4504. For example, an annulotomy may be performed using a long handled knife and kerrisons. A discectomy may be completed by using curettes and rongeurs. Removal of osteophytes which may have accumulated between the vertebrae may be performed using osteotomes and chisels. All or only a portion of the disc material within the interbody space I may be removed prior to insertion of the implant 4500. In some methods, the disc material is entirely removed where it will serve no further purpose or will detract from the performance of the implant 4500. Any of the foregoing procedures to prepare the interbody space I may be performed though the access device 4504 inserted as shown or through a second access device inserted through any suitable approach.

In some methods, a distraction means (not shown in FIG. 77) may be provided to further prepare the interbody space I. As indicated by FIG. 78, the distraction means may be used to create a distracted space 4556 in the interbody space I through the same access device used to deliver the implant 4500. The distraction means may take any suitable form, e.g., a paddle distractor, a jacking instrument, etc. Other distraction means known to those of skill in the art could also be used, if configured to be inserted through the access device 4504.

The distracted space 4556 may be formed by manipulating the distraction means to provide a selected separation between the first vertebra $V_1$ and the second vertebra $V_2$. The separation and the amount of disc material removed may be selected based on the size of the implant 4500 so as to create sufficient space for the implant 4500 to be received therein. After the distracted space 4556 is formed, the distraction means may be removed to free up the passage 4528 to receive the implant 4500.

In another method, the distraction means is provided through a second access device at about the same time or before the implant 4500 is inserted through the first access device 4504. Any of the approaches described herein or any other suitable approach may be used to deliver the distraction means separately from the implant 4500. In another embodiment, the distraction means is provided through an aperture similar to the aperture 4536 so that the proximal portion of the passage 4528 is unobstructed, and the space therein can be substantially entirely used for the delivery of the implant 4500 during a portion of the method.

FIG. 78 illustrates methods of applying the implant 4500 through the access device 4504. In particular, after the access device 4504 is actuated to the expanded configuration, the implant 4500 is delivered laterally as indicated by the arrow 4540 to a surgical location defined by the distal end 4516 of the access device 4504 at one lateral side of the vertebrae $V_1$, $V_2$ and into the interbody space I. In one application, in order to facilitate insertion of the implant 4500, visualization of the surgical site may be achieved in any suitable manner, e.g., by use of a viewing element 4532, as discussed above.

In one procedure, a gripping apparatus 4580, not shown in FIG. 78, is coupled with one or more portions and/or surfaces of the implant 4500 to facilitate insertion of the implant 4500. In one embodiment, the gripping apparatus 4580 is similar to the tool 2032, described above. The gripping apparatus 4580 has an elongate body 4584 that extends between a proximal end (not shown) and a distal end 4588. The length of the elongate body 4584 is selected such that when the gripping apparatus 4580 is inserted through the access device 4504 to the surgical location, the proximal end extends proximally of the proximal end 4512 of the access device 4504. This arrangement permits the surgeon to manipulate the gripping apparatus 4580 proximally of the access device 4504. The gripping apparatus 4580 has a grip portion 4592 that is configured to engage the implant 4500. In one embodiment, the grip portion 4592 comprises a clamping portion 4596 configured to firmly grasp opposing sides 4598 of the implant. The clamping portion 4596 may further comprise a release mechanism, which may be disposed at the proximal end of the gripping apparatus 4580, to loosen the clamping portion 4596 so that the implant 4500 may be released once delivered to the interbody space I. In another embodiment, the grip portion 4592 comprises a jaw portion with protrusions disposed thereon, such that a portion of the implant 4500 fits within the jaw portion and engages the protrusions. In another embodiment, the grip portion 4592 comprises a malleable material that can conform to the shape of the implant 4500 and thereby engage it. Other means of coupling the gripping apparatus 4580 to the implant 4500 known to those of skill in the art could also be used, if configured to be inserted through the access device 4504.

As shown in FIG. 78, the implant 4500 may be configured to be engaged by the grip portion 4592 of the gripping apparatus 4580. For example, the implant 4500 could include a tab 4600 configured to be engaged by the grip portion 4592 of the gripping apparatus 4580. In one embodiment, the tab 4600 is configured to fit within a jaw portion and engage the protrusions disposed thereon. In another embodiment, the tab 4600 may be configured to fit within a clamping portion 4596 that can be tightened upon it. In another embodiment, the tab 4600 may be configured to mate closely with a corresponding surface in the grip portion 4592 of the gripping apparatus 4580.

In one method of delivering the implant 4500 to the surgical location, the gripping apparatus 4580 is coupled with the implant 4500, as described above. The gripping apparatus 4580 and the implant 4500 are advanced into the proximal end 4516 of the access device 4504, to the surgical space 4542, and further into the interbody space I.

Figure 79:
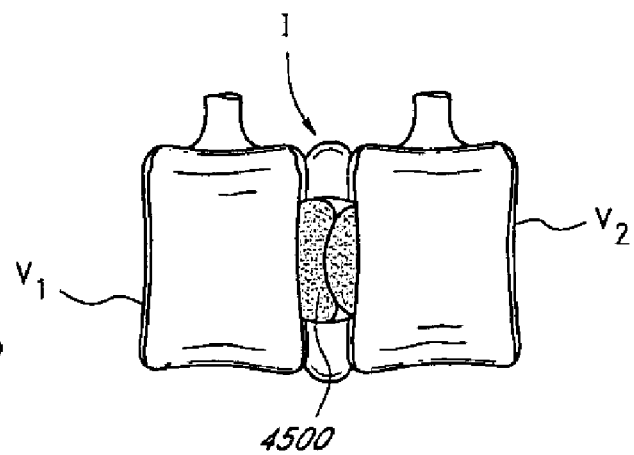
FIG. 79 is a schematic view similar to that of FIG. 77 showing a spinal implant configured to preserve or restore motion inserted into an interbody space.

As shown in FIG. 79, in one application, the implant 4020 is delivered into the interbody space I. The first portion 4021 of the implant 4020 may be delivered to the interbody space I first and thereafter coupled with the lower surface of the superior vertebra $V_1$ defining the interbody space I. As discussed above, each of the first and second portions of each of the implants 4020, 4030 preferably has a generally planar surface. In some embodiments, these surfaces have an element that extends therefrom, which is intended to mate with a corresponding feature, e.g., a hole, formed in the vertebrae $V_1$, $V_2$ as discussed above. Next, the second portion 4022 of the implant 4020 may be delivered to the interbody space I through the same or a different access device, as discussed above, and thereafter coupled with the upper surface of the inferior vertebra $V_2$ defining the interbody space l. Analogous procedures may be performed in connection with the implants 4030, 4110, 4210, 4300, 4400.

The implant 4500 may have to be temporarily fixed in place until it becomes secure, e.g., until sufficient bone growth occurs between the adjacent vertebrae $V_1$, $V_2$ and one or more surfaces of the implant 4500. In other applications, a structure similar to the endcap 4190 could be used to temporarily assist in the securement of the implant 4500 to the adjacent bone structure until the implant 4500 becomes more permanently secure. FIG. 79 shows the spine after the implant 4500 has been inserted between the vertebrae $V_1$, $V_2$.

Figure 80:
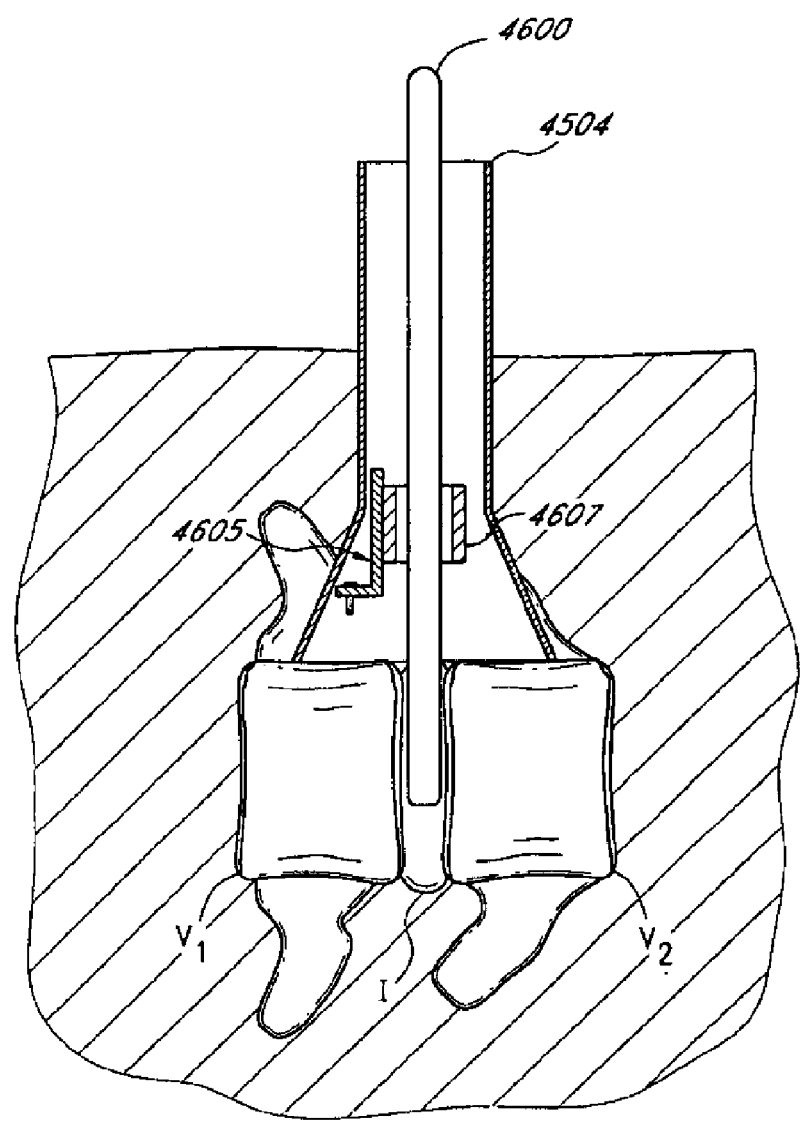
FIG. 80 is a schematic posterior view of a portion of a spine with an access device applied thereto to insert a guide to an interbody space.
Figure 81:
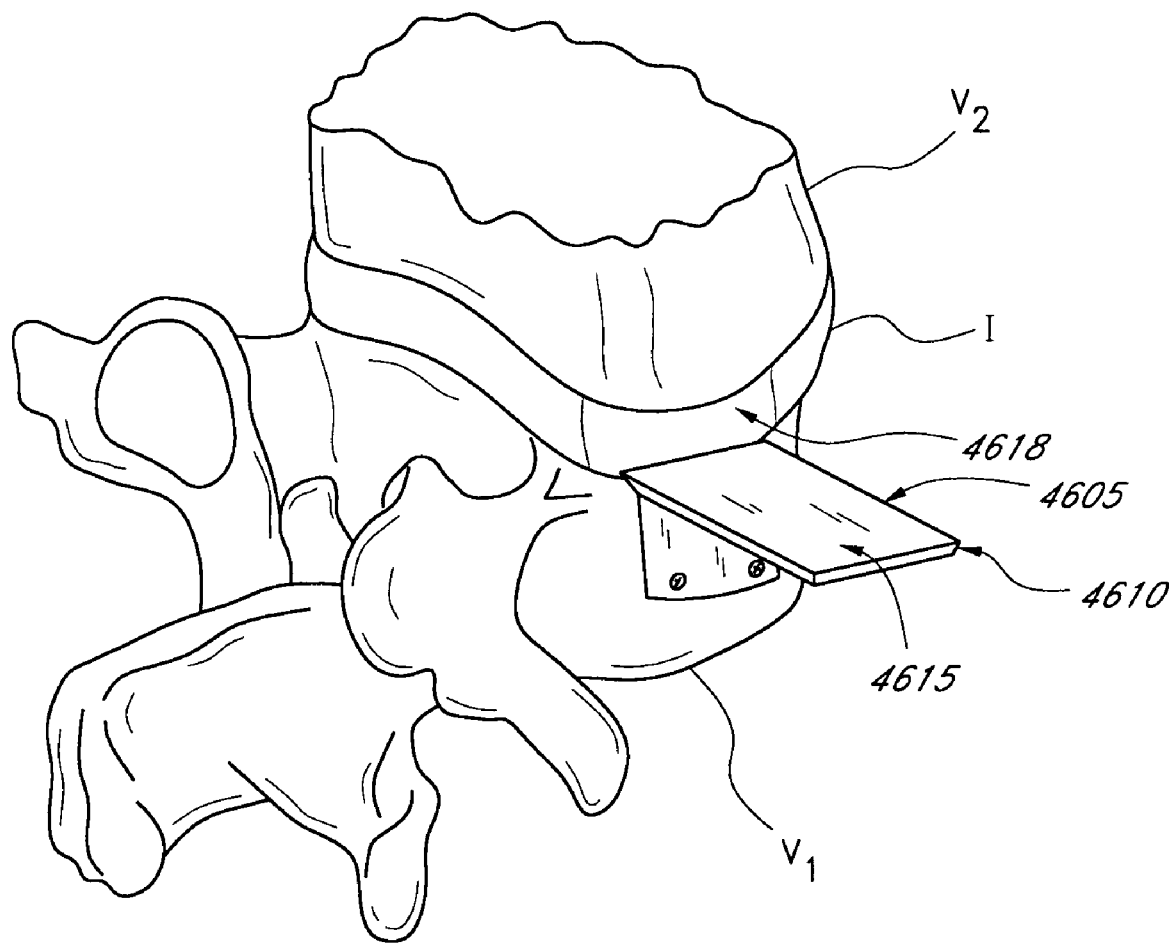
FIG. 81 is a perspective view of one embodiment of a guide attached to a vertebra, facilitating access to an interbody space.

FIGS. 80-82 provide further, detailed methods by which an interbody space may be prepared for the insertion of an implant 4500 delivered through an access device 4504. The methods illustrated are performed via a lateral approach; however, other approaches are also possible, including those enumerated above.

FIG. 80 illustrates the access device 4504 inserted into a patient in a manner such as those discussed above with reference to FIGS. 76-79. Using fluoroscopy in a preferred embodiment to accurately identify the damaged disc, a registration paddle 4600 is inserted through the access device 4504 into the intervertebral disc space. The registration paddle 4600 serves as a place marker to register the location and orientation of the disc that needs to be at least partially replaced with a spinal implant. The registration paddle 4600 preferably has an elongate body that extends between a proximal end and a distal end. The length of the elongate body is selected such that when the registration paddle 4600 is inserted through the access device 4504 to the surgical location, the proximal end extends proximally of the proximal end of the access device 4504, as shown. This arrangement permits the surgeon to manipulate the registration paddle 4600 proximally of the access device 4504. As is well known to those of skill in the art, the registration paddle's distal end corresponds roughly to the shape and size of the interbody space, such that it cannot twist or move easily.

With the registration paddle 4600 accurately positioned and oriented, a guide 4605 with a collar 4607 is then placed over the registration paddle 4600 and slid down to a location proximal the vertebrae. This guide 4605 may then be attached to a vertebra adjacent the interbody space in a number of ways well-known to those of skill in the art. In one application, the guide 4605 may be inserted using a tool similar to the gripping apparatus 4580 described above. In the illustrated embodiment, the guide 4605 is then screwed into the adjacent vertebral body. As will be appreciated, the guide 4605 will be in a particular location and orientation relative to the intervertebral disc. As a result, subsequent disc preparation and implant insertion procedures can be performed relative to this guide 4605 with greater ease and less reliance on endoscopic apparati. Of course, many other means may be used to affix the guide at various locations and orientations with respect to the interbody space, as is well known to those of skill in the art.

FIG. 81 illustrates in greater detail one embodiment of a guide 4605 in position on a vertebra adjacent an interbody space. The guide 4605 includes a dovetail guide 4610. Other surgical instruments may have corresponding surfaces that engage with this dovetail guide 4610 in order to guide them to the interbody space in a proper orientation. The guide 4605 itself, with its planar surface 4615, also provides orientation and location information to a surgeon. Using this guide 4605, various instruments may be inserted in proper orientation and position relative to the interbody space. In the illustrated embodiment, an annulotomy has been performed directly adjacent the guide 4605, creating an opening 4618 in the spinal disc's annulus.

In other embodiments, other means of locating devices relative to the guide 4605 may be used, including simple grooves and milled paths. In still other embodiments, the guide's surface may not be planar, but may have other geometries that help to guide instruments to the vertebrae. In another embodiment, the guide 4605 may not provide more guidance than its own planar surface running roughly parallel to the intervertebral disc space.

Figure 82A:
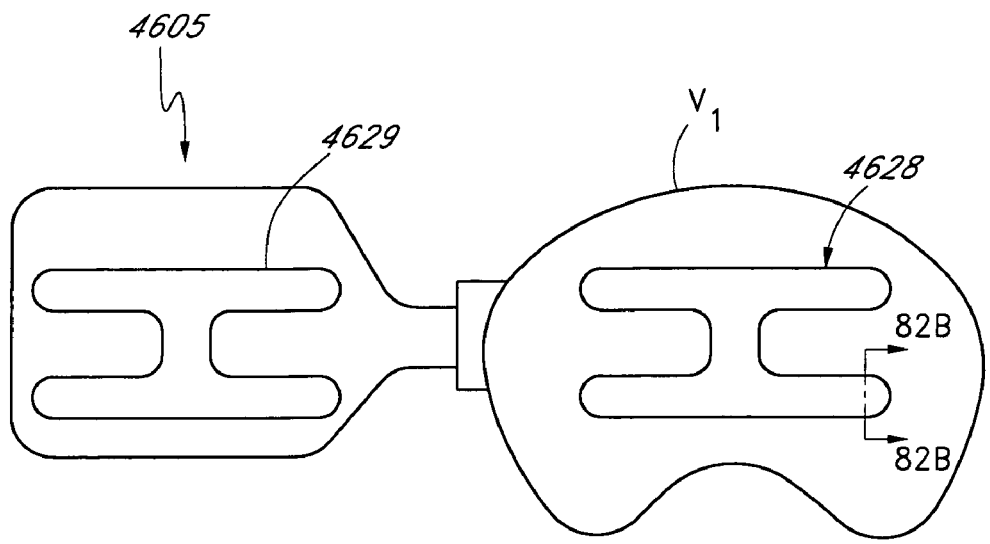
FIG. 82A is a view of one method of preparing an interbody space for the insertion of a spinal implant into an interbody space using a guide.
Figure 82B:
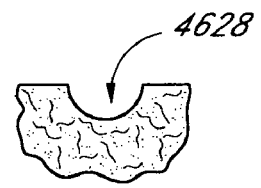
FIG. 82B is a cross-sectional view of a path shown in FIG. 82A.
Figure 82C:
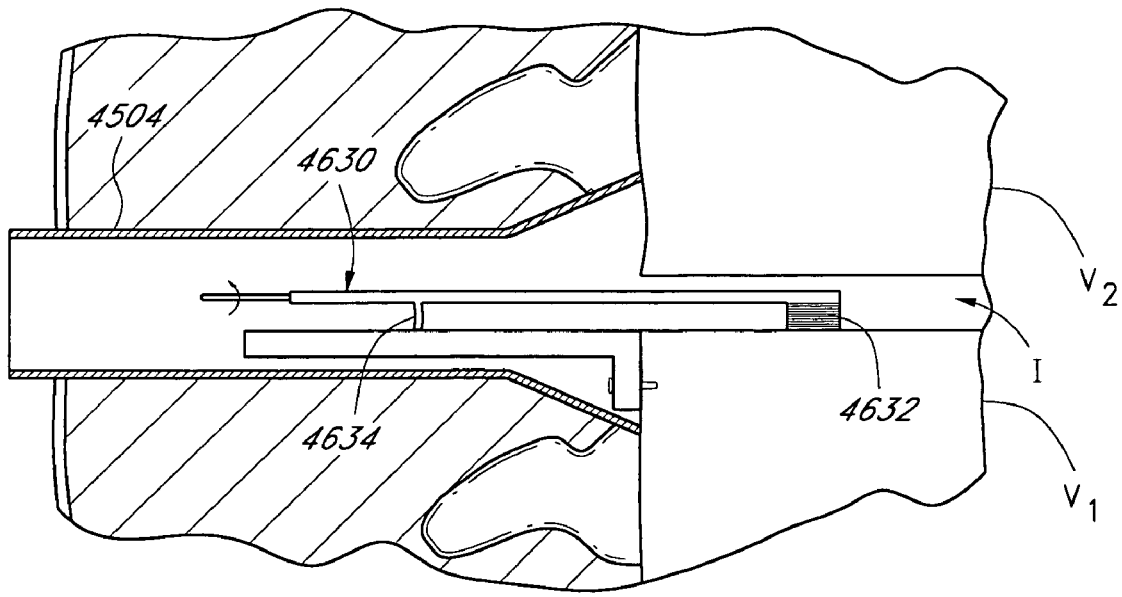
FIG. 82C is a lateral view of a portion of a spine with an access device, guide and mill applied thereto for preparing an interbody space for a spinal implant.

FIGS. 82A, 82B and 82C show an embodiment of the guide 4605 facilitating the production of milled patterns on the vertebrae in order to facilitate the introduction of a spinal implant. In the illustrated embodiment, the implant to be inserted has an H-formation that faces the vertebral body. If the vertebral body were to have an H-formation 4628 milled from its bone, then the implant would seat better within the disc space and heal more quickly. (See FIGS. 82A and 82B.)

In the illustrated embodiment, the method of performing this preparatory operation is to have a template 4629 milled in the guide 4605. A mill 4630 is provided that has a cutting edge 4632 at its distal end and a protrusion 4634 near its distal end. The distance chosen between the protrusion 4634 and cutting edge 4632 is chosen to correspond to the distance between the template 4629 in the guide 4605, and a corresponding milled location 4628 in the intervertebral space. Thus, as illustrated in FIG. 82C, the cutting edge 4632 and the protrusion 4634 of the mill 4630 are inserted through the access device 4504. Before cutting, the protrusion 4634 is located within the template 4629 of the guide 4605. The surgeon then follows the template with the mill 4630 in order to make a similar set of milled grooves 4628 within the vertebral body. This process makes the surgical procedure faster and more efficient.

Of course, other uses may also be found for the guide 4605. In one embodiment, not shown, the guide may facilitate the insertion of the implant 4500, by providing the necessary orientation and location information. In another embodiment, the guide 4605 may be used to facilitate the removal or adjustment of an implant that has been previously inserted. In other embodiments, the guide 4605 may be used for a number of other procedures that require knowledge of location and orientation near the spinal column. For example, pedicle screws may be inserted more accurately using the guide 4605, and spinal nucleus replacement may also be facilitated.

Although the forgoing procedures are described in connection with a single level lateral or postero-lateral procedure, other procedures are possible. For example, multiple level disc replacement could be performed with the expandable conduit 20 or other suitable access device. As discussed above, other applications are also possible in which the access device 4504 is not expanded prior to delivery of the implant 4500. In such applications, the access device 4504 remains in the first configuration while the steps described above are performed, or a non-expandable access device may be provided. Also, other approaches could be adopted, e.g., anterior, posterior, transforaminal, or any other suitable approach. In one application, the implant 4500 is inserted at the L5-S1 vertebrae or at the L5-L4 vertebrae anteriorly through the access device 4504. Also, a motion preserving disc replacement procedure could be combined with a fusion procedure in two different interbody spaces, e.g., two adjacent interbody spaces.

Although the methods discussed above are particularly directed to the insertion of an implant 4500, the access device 4504 may also be used advantageously to remove the implant 4500. It may be desirable to remove the implant 4500 if the patient's spine condition changes or if the performance of the implant 4500 is compromised, e.g., through wear or subsidence (reduction in the height of the implant). In one application, the tab 4600 disposed on the implant 4500 may be further configured to facilitate subsequent removal. The gripping apparatus 4580 may also be further configured to facilitate removal as well as insertion. By providing minimally invasive access to the interbody space I, the access device 4504 may be used analogously as described above with reference to the removal of the natural disc material, to remove a previously inserted implant 4500. Upon removal of the implant 4500, various subsequent procedures may be performed in the interbody space I. For example, a new implant 4500 may be inserted through the access device 4504 into the interbody space I. Other procedures that could be performed after removing the previously inserted implant 4500 include the insertion of a fusion device, such as the spinal implant 2010, where it is determined that fusion is a more suitable treatment than disc replacement. Such a determination may arise from a change in the condition of the spine, e.g., due to the onset of osteoporosis, that makes disc replacement inappropriate.

Another procedure that may be performed through the access device 4504 involves replacement of two or more joints. Some patients who are suffering from degenerative disc disease also suffer from degenerative facet joint disease. While replacement of both a disc and a facet joint in such a patient is possible during the same operation using other methods, such an operation would be very complicated because it would likely require that the spine be approached both anteriorly and posteriorly. In contrast, in some approaches described hereinabove, the access device 4504 would provide sufficient access to both the interbody space I to facilitate replacement of a disc with the implant 4500 and to one or more facet joints to facilitate replacement of one or more facet joints. For example, the postero-lateral approaches indicated by the arrows 4544, 4552 could provide access to a disc in the interbody space I and an adjacent facet joint. In another method, first and second access devices could be applied in any combination of the lateral and postero-lateral approaches indicated by the arrows 4540, 4548, 4544, and 4552, or other approach, to provide access to a disc in the interbody space I and an adjacent facet joint. In one method three or more joints are replaced, e.g., a disc in the interbody space I and the two corresponding, adjacent facet joints by way of one or more access device applied along any combination of the approaches 4540, 4544, 4548, and 4552, or other approach.

The foregoing methods and apparatuses advantageously provide minimally invasive treatment of disc conditions in a manner that preserves some degree of motion between the vertebrae on either side of a replaced disc. Accordingly, trauma to the patient may be reduced thereby, and recovery time shortened. As discussed above, many of the implants provide a more normal post-recovery range of motion of the spine, which can reduce the need for additional procedures.

It will be understood that the foregoing is only illustrative of the principles of the invention, and that various modifications, alterations, and combinations can be made by those skilled in the art without departing from the scope and spirit of the invention.

What is claimed is:

1. A method of replacing an intervertebral disc in an intervertebral space of a spine of a patient, comprising:
   inserting an access device through an incision in a skin of the patient;
   expanding said access device from a first configuration to a second configuration, the second configuration having an enlarged cross-sectional area at a distal portion of said access device such that the distal portion extends across at least a portion of the intervertebral space;
   fastening a guide to the cortical wall of a vertebra adjacent the intervertebral space such that the guide does not extend into the intervertebral space;
   preparing the intervertebral space to receive the implant wherein said preparing step is performed through the access device;
   and delivering a prosthetic spinal disc implant through the access device.

2. The method of claim 1, wherein inserting further comprises inserting the access device along a lateral approach.

3. The method of claim 1, wherein inserting further comprises inserting the access device along a posterolateral approach.

4. The method of claim 1, wherein the prosthetic spinal disc implant mimics functionality of a natural intervertebral disc.

5. The method of claim 1, wherein said access device is a first access device, and further comprising inserting a second access device through an incision in a skin of the patient, and delivering an additional prosthetic spinal disc implant through the second access device.

6. The method of claim 1, wherein the step of preparing the intervertebral space further comprises locating the intervertebral space by inserting a registration paddle through said access device at least partially into said intervertebral space.

7. The method of claim 1, wherein the guide comprises a dovetail with which instruments may engage.

8. The method of claim 1, wherein the step of preparing further comprises milling a path in the intervertebral space using a template in the guide.

9. The method of claim 1, further comprising providing visualization into at least a portion of the access device.

10. The method of claim 1, wherein the fastening step includes screwing the guide into the vertebra.

11. A method of preparing an intervertebral space for the insertion of an implant delivered through an access device, comprising:
    inserting an access device through an incision in the skin of a patient; wherein the access device has a proximal end and a distal end and a path therethrough;
    wherein the access device is inserted such that an opening at its distal end overlaps with an intervertebral space; wherein the intervertebral space is the surgical site;
    registering the location and orientation of the intervertebral disc that needs to be at least partially replaced; wherein registering includes inserting a registration paddle through the access device and at least partially into the intervertebral space;
    placing a guide over the registration paddle such that the guide slides down the registration paddle to a position proximal a vertebra adjacent the intervertebral space surgical site; and
    fastening the guide to a cortical wall of the vertebra adjacent the intervertebral space surgical site.

12. The method of claim 11, wherein the guide has a shaped surface, wherein the method further comprises inserting a surgical instrument and engaging the shaped surface with the surgical instrument to guide the surgical instrument to the intervertebral space surgical site in a predetermined orientation.

13. The method of claim 12, wherein the guide has a shaped edge wherein engaging the shaped edge with the surgical instrument causes the surgical instrument to follow a pattern at the surgical site.

14. The method of claim 11, wherein the guide includes a template on a surface substantially perpendicular to the cortical wall.

15. The method of claim 14, wherein the template has a milled pattern.

16. The method of claim 15, further comprising:
    inserting a tool into the access device; wherein the tool has a pattern forming member at its distal end; wherein the tool has a marker proximal its distal end;
    engaging the marker on the tool with the milled template on the guide;
    moving the marker along the milled pattern of the template, thereby forming the same pattern of the template on the surface of the vertebra.

17. The method of claim 16, wherein the tool is a cutting device.

18. The method of claim 17, wherein the cutting device is a mill.

19. The method of claim 16, wherein the marker is a protrusion.

20. The method of claim 16, further comprising:
    inserting an intervertebral disc implant through the access device; wherein the disc implant has a pattern complementary to that formed on the vertebral surface.

21. The method of claim 11, wherein the registration paddle has an elongate body extending between a proximal end and a distal end;
    wherein the length of the elongate body is selected such that when inserted through the access device the proximal end of the elongate body extends proximally of the proximal end of the access device and the distal end of the elongate body extends distally of the distal end of the access device.

22. The method claim 21, wherein the shape and size of the distal end of the registration paddle approximates the shape and size of the intervertebral space.

23. The method of claim 11, wherein after inserting the access device, the access device is expanded from a first configuration to a second configuration;
    wherein the second configuration has an enlarged cross-sectional area at a distal portion.

24. The method of claim 11, wherein the fastening step includes screwing the guide into the vertebra.

25. A method of preparing an intervertebral space for the insertion of an implant delivered through an access device, comprising:
- inserting an access device through an incision in the skin of a patient; wherein the access device has a proximal end and a distal end and a path therethrough;
- wherein the access device is inserted such that an opening at its distal end overlaps with an intervertebral space; wherein the intervertebral space is the surgical site;
- inserting a guide through the access device and fastening the guide in a desired orientation in a specific position to the cortical wall of a vertebra adjacent the intervertebral space surgical site;
- wherein the guide has a pattern;
- inserting a surgical instrument through the access device, the surgical instrument having a pattern forming member at its distal end; and
- engaging the pattern of the guide with the surgical instrument and moving the surgical instrument such that the surgical instrument follows the pattern and forms a pattern on the surface of the vertebra that is the same as the pattern on the guide.

26. The method of claim 25, wherein the pattern forming member is a cutting edge.

* * * * *

UNITED STATES PATENT AND TRADEMARK OFFICE
CERTIFICATE OF CORRECTION

PATENT NO.      : 7,655,012 B2                         Page 1 of 1
APPLICATION NO. : 10/842651
DATED           : February 2, 2010
INVENTOR(S)     : DiPoto et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1052 days.

Signed and Sealed this

Twenty-third Day of November, 2010

David J. Kappos
*Director of the United States Patent and Trademark Office*